(12) United States Patent
Webster et al.

(10) Patent No.: US 6,680,429 B1
(45) Date of Patent: *Jan. 20, 2004

(54) **STARCHLESS VARIETY OF *PISUM SATIVUM* HAVING ELEVATED LEVELS OF SUCROSE**

(75) Inventors: David Webster, Buhl, ID (US); Diane Burgess, Berkeley, CA (US)

(73) Assignee: Seminis Vegetable Seeds, Inc., Oxnard, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/555,820
(22) PCT Filed: Dec. 7, 1998
(86) PCT No.: PCT/US98/25912

§ 371 (c)(1),
(2), (4) Date: Aug. 29, 2000

(87) PCT Pub. No.: WO99/29161

PCT Pub. Date: Jun. 17, 1999

Related U.S. Application Data

(63) Continuation of application No. 09/015,711, filed on Jan. 29, 1998, now Pat. No. 6,127,605, which is a continuation-in-part of application No. 08/986,616, filed on Dec. 8, 1997, now abandoned.

(51) Int. Cl.[7] .......................... A01H 5/00; A01H 5/10; A01H 4/00; A01H 1/00
(52) U.S. Cl. .............. 800/298; 800/295; 800/265; 800/263; 800/260; 800/270
(58) Field of Search ................... 800/298, 295, 800/265, 263, 260, 270

(56) References Cited

U.S. PATENT DOCUMENTS

| 5,286,635 A | 2/1994 | Hanson et al. |
| 5,498,831 A | 3/1996 | Burgess et al. |
| 5,646,023 A | 7/1997 | Secor et al. |
| 5,705,375 A | 1/1998 | Van Ooyen et al. |
| 6,127,605 A | * 10/2000 | Webster ............... 800/298 |

FOREIGN PATENT DOCUMENTS

| EP | 0654 541 A1 | 5/1995 |
| WO | WO 98/01574 | 1/1998 |

OTHER PUBLICATIONS

Seminis Vegetable Seeds Inc. Standard Seed Contact To Grow Seeds (Oct. 1997).
Wang, T.L., t al., IPSR & JIC Annual Report (1992).
Peas: Genetics, Molecular Biology Biotechnology 5. Genetic and Developmental Analysis of the Seed; Edited by Casey R. Davis D.R., pp. 83–120 (1993) ISBN–0–85198–863–6.
Wang, T.L., et al., *Seed Science Research*, 1:3–14 (1991).
Wang., T.L., et al. *Plant Breeding*, 105:311–320 (1990).
Harrison, C.J. et al. *The Plant Journal*, 13(6):753–762 (1998).
International Search Report for PCT/US98/25912.
Gaze R. R., et al. *Journal of Food Technology*, vol. 21(3):319–330 (1986).
Basterrechea et al., *Scientia Horticulturae* 48(1–2):1–8 (1991).
International Preliminary Examination Report for PCT/US98/25912.

* cited by examiner

*Primary Examiner*—David T. Fox
*Assistant Examiner*—Russell Kallis
(74) *Attorney, Agent, or Firm*—Wood, Phillips, Katz, Clark & Mortimer

(57) ABSTRACT

The present invention relates to a *Pisum sativum* variety that contains a recessive gene called the bsg gene and produces peas that exhibit an elevated level of sucrose and a decreased level of alcohol insoluble solids when compared to peas produced from a *Pisum sativum* variety that does not contain the bsg gene within its genome.

3 Claims, 14 Drawing Sheets

Figure 6

```
     HindIII (1)
   1 AAGCTTCAGTGTGGAAGTAATAGACCCAGTTTCTGATTACCTGGAGTTATTGGAGGTCAAAATAATCTTTTT
  73 TCTTCATTATAATCCAGTAGAATGATTCATGCAAGCTCGATCTCTGTGTTGAGAGTTTTATTTCATTTCATTTCGTCTAAGT
 155 TTATTTGTTATTATTTTTTGTGCAGACAGTGTTCGATTTTCAGCTAATCAAAAGTCTTATTTCACGGCCAGAT
                                                       XbaI (281)
 228 TTTAGGTACAACCTTAACATTTATTCCACCATAATCCAAATCTTGGCACATTGTCTAGAATCTGATTGTGTTAAATTTTTT
                   SphI (335)
 309 TATTTTAGGTTTACATTTGATGCCATGCATGCAGTTGCCGGTGCTTATGCAACACCCATTTTCGTTGATAA
 380 ACTTGGTGCTAGTCCGGTATAGTTCTTCCCCTTTTACTCTTGTACATAGCGGGTACAAGTTTATACGGTATTGTTGATT
 459 TTGGGTGTTAAGTATGCAATGTAGGATTCAATTTCAAATGGAATACCTTTGGAAGATTTTGGACATGGTCATC
 532 CTGATCCTAATCTAACGTGAGTTTAGTTTTATATTTTCGACATTGTGTTTTCAATCATTAGTAAATTGTTTTTGATTCT
 611 AATGTTTATTGAACAGATACGCAAAGGATCTTGTCAATATTTATGTATGCTGAAAACGGACCTGATTTTGGTG
 683 CCGCTAGTGATGGTATGCGAGATTTTAGTTATTTTTGAAATTTAACTTGTTTCCGTTGATAAATCCTTGTGCAACAATGT
                                                    BglII (801)
 763 TTTGTCTGAACCCAAGAGCAATTGGATGAGATGGTAAGAGATCTCTTTCAGCTTAACCTGAGGTCCTGAGTTTGAACTCAGT
                                                                   XhoI (912)
 845 CCTGGGCACGCAACAGTGCTAAATTCTCTTGAGAGAGAACTTTGCCGTCCATTGCGGTCCTCCCCAGCTCGAGGGATTAGTC
         PstI (928)
 927 TCTGCAGTTGCACGCAGAGGATACCCGATTTTTACTGTAAAAAAACAATGTTTTTTGTCTGCATTTGTTTACTTGATAATGT
1009 TTATGTATTTTAACTTTCGTTTAGGTGATGGTGATAGAAATATGATTTTGGGAACAAGTTTCTTCGTAACTCC
1082 TTCAGACTCTGTAGCCGTTATTGCAGCCAATGCAAAAGAAGCGATTCCGTACTTTAAGGACAGTATCAAG
1152 GTAGAAAGTTTGTGCATATCATATTATTCACAAGTATTCGTTGTTGTAAAACAGAAGTGTCATTGTTCTGTATTGTAATTGC
                                                 XbaI (1268)
1234 AGGGTCTTGCACGATCAATGCCGACAAGCGGTGCTCTAGANNNNNNNNNNNNNNNNNNNNNNNNNNNNNNNNNN
                                                 XbaI (1351)
1304 NNNNNNNNNNNNNNNNNNNNNNNNNNNNNNNNNNNNNNNNNNNNNNNNNTCTAGATTATGGTTCTCGAATGACAGACGGACC
1384 TCGGGTGCAGGTTCCCACTGGTTGGAAATTCTTTGGTAATCTTATGGATGCTGGAAATCTGTCGATTTGCG
1455 GGGAAGAGAGTTTTGGAACAGGTTCTGACCACATTCGTGAGAAAGACGGAATCTGGTAACTTTCTTATTTTT
1527 GTATTGAGAATAGCGGGTCGAGCATTTATCAAACATTATCTAAGTTTCTCCGACTTATTAATATTATTGGGCTGTATTAG
                                                                                *
1607 CTTGGCTTTCGATTATTGCTCACCGCAACAAAGACACGAAACCAGGGGAGAAATTGGTCTCTGTGTCTGA
                                                 XbaI (1720)
1677 TGTTGTGAAGGAGCATTGGGCAACCTATGGTAGAAATTTCTTTTCTAGATACGATTACGAGGTTGGTTTTG
1748 ATGCTGCAATTGAAGTTTTATTTGTTGTATCACACACTTTGAAGTTTTATTTTTCTTTTGAGTTTTGACAAATATAAATATA
1830 GGAATGTGAATCCGAAGGCGCAAATAAGATGATAGAGTACCTACGAGAGCTTTTGTCGAAGAGCAAGCCT
1900 GGTGATAAGTATGGTAAGTTACTCACAACCACTTTCTTATCACAGACACGGAGACACGGACACCAAACACGACATTGAC
1979 ATTGGCACGTAATCATTAGCATACACTTTCCCTGAGTATATTTAAAGTGTGATGAGTTTTCTTGTACAGGAAGTTACGTC
2059 CTCCAGTTTGCCGATGATTATACATACACTGATCCTGTAAGTTCTTACAACTTCACATTCTCATCATGTTGATTTT
2135 TGTTTCTTCAACTTACGGTAAATCAACCATAGTTCAAATTCTGATTGAATAAAAACATGCAGGTAGATGGAAGTGTAGT
2214 ATCAAAACAAGGGGTTCGGTTTGTTTTCACCGATGGTTCAAGAATTATTTACCGTTTATCAGTAAGTAACG
2285 TCTGTTTAATTACTTACCCGAAAAATTTATGAAATGAAATATTAAGTGATTACTTACGGTGTTTTGTTTACAGGAACG
2365 GGTTCTGCTGGTGCAACTGTTAGAGTG
     ◄
```

Figure 7

```
       HindIII (1)
   1   AAGCTTCAGTGTGGAAGTAATAGACCCAGTTTCTGATTACCTGGAGTTATTGGAGGTCAAAATAATCTTTTT
  73   TCTTCATTATAATCCAGTAGAATGATTCATGCAAGCTCGATCTCTGTGTTGAGAGTTTTATTTCATTTCATTTCGTCTAAGT
 155   TTATTTGTTATTATTTTTTGTGCAGACAGTGTTCGATTTTCAGCTAATCAAAAGTCTTATTTCACGGCCAGAT
                                                  XbaI (281)
 228   TTTAGGTACAACCTTAACATTTATTCCACCATAATCCAAATCTTGGCACATTGTCTAGAATCTGATTGTGTTAAATTTTTT
                        SphI (335)
 309   TATTTTAGGTTTACATTTGATGCCATGCATGCAGTTGCCGGTGCTTATGCAACACCCATTTTCGTTGATAA
 380   ACTTGGTGCTAGTCCGGTATAGTTCTTCCCCTTTTACTCTTGTACATAGCGGGTACAAGTTTATACGGTATTGTTGATT
 459   TTGGGTGTTAAGTATGCAATGTAGGATTCAATTTCAAATGGAATACCTTTGGAAGATTTTGGACATGGTCATC
 532   CTGATCCTAATCTAACGTGAGTTTAGTTTTATATTTTCGACATTGTGTTTTCAATCATTAGTAAATTGTTTTTGATTCT
 611   AATGTTTATTGAACAGATACGCAAAGGATCTTGTCAATATTATGTATGCTGAAAACGGACCTGATTTTGGTG
 683   CCGCTAGTGATGGTATGCGAGATTTTAGTTATTTTTGAAATTTAACTTGTTTCCGTTGATAAATCCTTGTGCAACAATGT
                                                              BglII (801)
 763   TTTGTCTGAACCCAAGAGCAATTGGATGAGATGGTAAGAGATCTCTTTCAGCTTAACCTGAGGTCCTGAGTTTGAACTCAGT
                                                                      XhoI (912)
 845   CCTGGGCACGCAACAGTGCTAAATTCTCTTGAGAGAGAACTTTGCCGTCCATTGCGGTCCTCCCCAGCTCGAGGGATTAGTC
             PstI (928)
 927   TCTGCAGTTGCACGCAGAGGATACCCGATTTTTACTGTAAAAAAACAATGTTTTTTGTCTGCATTTGTTTACTTGATAATGT
1009   TTATGTATTTTAACTTTCGTTTAGGTGATGGTGATAGAAATATGATTTTGGGAACAAGTTTCTTCGTAACTCC
1082   TTCAGACTCTGTAGCCGTTATTGCAGCCAATGCAAAAGAAGCGATTCCGTACTTTAAGGACAGTATCAAG
1152   GTAGAAAGTTTGTGCATATCATATTATTCACAAGTATTCGTTGTTGTAAAACAGAAGTGTCATTGTTCTGTATTGTAATTGC
                                                           XbaI (1268)
1234   AGGGTCTTGCACGATCAATGCCGACAAGCGGTGCTCTAGATAGAGTTGCTGAAAAGTTGAACCTCCCTTT
                                                    XbaI (1351)
1304   TTTTGAGGTATAGTATGATTTTACATTGTTGTTGCGTTTAGAATTATTCTAGATTATGGTTCTCGAATGACAGACGGACC
1384   TCGGGTGCAGGTTCCCACTGGTTGGAAATTCTTTGGTAATCTTATGGATGCTGGAAATCTGTCGATTTGCG
1455   GGGAAGAGAGTTTTGGAACAGGTTCTGACCACATTCGTGAGAAAGACGGAATCTGGTAACTTTCTTATTTTT
                                                                           *
1527   GTATTGAGAATAGCGGGTCGAGCATTTATCAAACATTATCTAAGTTTCTCCGACTTATTAATATTATAGGGCTGTATTAG
1607   CTTGGCTTTCGATTATTGCTCACCGCAACAAAGACACGAAACCAGGGGAGAAATTGGTCTCTGTGTCTGA
                                                                     XbaI (1720)
1677   TGTTGTGAAGGAGCATTGGGCAACCTATGGTAGAAATTTCTTTTCTAGATACGATTACGAGGTTGGTTTTG
1748   ATGCTGCAATTGAAGTTTTATTTGTTGTATCACACACTTTGAAGTTTTATTTTTCTTTTGAGTTTTGACAAATATAAATATA
1830   GGAATGTGAATCCGAAGGCGCAAATAAGATGATAGAGTACCTACGAGAGCTTTTGTCGAAGAGCAAGCCT
1900   GGTGATAAGTATGGTAAGTTACTCACAACCACTTTCTTATCACAGACACGGAGACACGGACACCAAACACGACATTGAC
1979   ATTGGCACGTAATCATTAGCATACACTTTCCCTGAGTATATTTAAAGTGTGATGAGTTTCTTGTACAGGAAGTTACGTC
2059   CTCCAGTTTGCCGATGATTATACATACACTGATCCTGTAAGTTCTTACAACTTCACATTCTCATCATGTTGATTTT
2135   TGTTTCTTCAACTTACGGTAAATCA CCATAGTTCAAATTCTGATTGAATAAAAACATGCAGGTAGATGGAAGTGTAGT
2214   ATCAAAACAAGGGGTTCGGTTTGTTTTCACCGATGGTTCAAGAATTATTTACCGTTTATCAGTAAGTAACG
2285   TCTGTTTAATTACTTACCCGAAAAATTTATGAAATGAAATATTAAGTGATTACTTACGGTGTTTTGTTTACAGGGAACG
2365   GGTTCTGCTGGTGCAACTGTTAGAGTG
```

```
   1 CACTGTTACAGACTCGATCAATGGCTTTCTGTTACAGACTCGACAACTTCATCATCTCTGCGTTTAAACCCAAACACTCA
     1▶ MetAlaPheCysTyrArgLeuAspAsnPheIleIleSerAlaPheLysProLysHisSer

81 AATGTCCCACTTTCAATTCATCATTCATCATCCAATTTTCCTTCTTTCAAAGTTCAAAACTTTCCTTTCAGGGTTCGCTA
    21▶ AsnValProLeuSerIleHisHisSerSerSerAsnPheProSerPheLysValGlnAsnPheProPheArgValArgTy
                                                   A
 161 TAATTCAGCTATTAGAGCCACTTCGTCTTCCTCTTCTACTCCCACAACCATTGCAGAACCTAATGACATTAAGATTAACT
    47▶ rAsnSerAlaIleArgAlaThrSerSerSerSerThrProThrThrIleAlaGluProAsnAspIleLysIleAsnS
                                                   A             KpnI (276)    T
 241 CTATTCCTACTAAACCTATTGAAGGACAAAAAACTGGTACCAGTGGCCTAAGAAAAAAGGTGAAAGTGTTTAAGCAAGAA
    74▶ erIleProThrLysProIleGluGlyGlnLysThrGlyThrSerGlyLeuArgLysLysValLysValPheLysGlnGlu

321 AATTACCTTGCAAATTGGATTCAGGCACTGTTTAATTCGTTGCCGCCGGAGGATTACAAGAATGGATTGTTGGTTTTGGG
   101▶ AsnTyrLeuAlaAsnTrpIleGlnAlaLeuPheAsnSerLeuProProGluAspTyrLysAsnGlyLeuLeuValLeuGl

401 AGGCGATGGTCGATACTTCAATAAAGAAGCTGCACAGATAATAATCAAGATTGCTGCTGGAAATGGTGTTGGAAAAATTC
   127▶ yGlyAspGlyArgTyrPheAsnLysGluAlaAlaGlnIleIleIleLysIleAlaAlaGlyAsnGlyValGlyLysIleL

481 TGGTTGGGAAGGAAGGGATATTGTCAACGCCAGCCGTTTCTGCTGTGATAAGGAAGAGAGGCAAATGGTGGGTTTATC
   154▶ euValGlyLysGluGlyIleLeuSerThrProAlaValSerAlaValIleArgLysArgGluAlaAsnGlyPheIle

561 ATGAGTGCGAGCCATAACCCTGGTGGACCTGAATATGATTGGGTATTAAGTTTAATTACAGTAGCGGACAACCTGCACC
   181▶ MetSerAlaSerHisAsnProGlyGlyProGluTyrAspTrpGlyIleLysPheAsnTyrSerSerGlyGlnProAlaPr
                                                         ClaI (677)
 641 AGAATCCATCACCGACAAGATTTACGGAAACACCCTATCGATTTCTGAGATAAAGATTGCTGATATTCCCGATGTTGACT
   207▶ oGluSerIleThrAspLysIleTyrGlyAsnThrLeuSerIleSerGluIleLysIleAlaAspIleProAspValAspL
                         HindIII (749)
 721 TATCAAATGTTGGAGTTACGAAATTCGGAAGCTTCAGTGTGTGGAAGTAATAGACCCAGTTTCTGATTACCTGGAGTTATTG
   234▶ euSerAsnValGlyValThrLysPheGlySerPheSerValGluValIleAspProValSerAspTyrLeuGluLeuLeu
                                                                              SphI (875)
 801 GAGACAGTGTTCGATTTTCAGCTAATCAAAAGTCTTATTTCACGGCCAGATTTTAGGTTTACATTTGATGCCATGCATGC
   261▶ GluThrValPheAspPheGlnLeuIleLysSerLeuIleSerArgProAspPheArgPheThrPheAspAlaMetHisAl 881 AGTTGCCGGTGCTTATGCAACACCCATTTTCGTTGATAAACTTGGTGCTAGTCCGGATTCAATTTCAAATGGAATACCTT
   287▶ aValAlaGlyAlaTyrAlaThrProIlePheValAspLysLeuGlyAlaSerProAspSerIleSerAsnGlyIleProL 961 TGGAAGATTTTGGACATGGTCATCCTGATCCTAATCTAACATACGCAAAGGATCTTGTCAATATTATGTATGCTGAAAAC
   314▶ euGluAspPheGlyHisGlyHisProAspProAsnLeuThrTyrAlaLysAspLeuValAsnIleMetTyrAlaGluAsn 1041 GGACCTGATTTTGGTGCCGCTAGTGATGGTGATGGTGATAGAAATATGATTTTGGGAACAAGTTTCTTCGTAACTCCTTC
   341▶ GlyProAspPheGlyAlaAlaSerAspGlyAspGlyAspArgAsnMetIleLeuGlyThrSerPhePheValThrProSe 1121 AGACTCTGTAGCCGTTATTGCAGCCAATGCAAAAGAAGCGATTCCGTACTTTAAGGACAGTATCAAGGGTCTTGCACGAT
   367▶ rAspSerValAlaValIleAlaAlaAsnAlaLysGluAlaIleProTyrPheLysAspSerIleLysGlyLeuAlaArgS
                                                   XbaI (1220)
1201 CAATGCCGACAAGCGGTGCTCTAGATAGAGTTGCTGAAAAGTTGAACCTCCCTTTTTTTGAGGTTCCCACTGGTTGGAAA
   394▶ erMetProThrSerGlyAlaLeuAspArgValAlaGluLysLeuAsnLeuProPhePheGluValProThrGlyTrpLys 1281 TTCTTTGGTAATCTTATGGATGCTGGAAATCTGTCGATTTGCGGGGAAGAGAGTTTTGGAACAGGTTCTGACCACATTCG
   421▶ PhePheGlyAsnLeuMetAspAlaGlyAsnLeuSerIleCysGlyGluGluSerPheGlyThrGlySerAspHisIleAr 1361 TGAGAAAGACGGAATCTGGGCTGTATTAGCTTGGCTTTCGATTATTGCTCACCGCAACAAAGACACGAAACCAGGGGAGA
   447▶ gGluLysAspGlyIleTrpAlaValLeuAlaTrpLeuSerIleIleAlaHisArgAsnLysAspThrLysProGlyGluL
                                                                       XbaI (1503)
1441 AATTGGTCTCTGTGTCTGATGTTGTGAAGGAGCATTGGGCAACCTATGGTAGAAATTTCTTTTCTAGATACGATTACGAG
   474▶ ysLeuValSerValSerAspValValLysGluHisTrpAlaThrTyrGlyArgAsnPhePheSerArgTyrAspTyrGlu 1521 GAATGTGAATCCGAAGGCGCAAATAAGATGATAGAGTACCTACGAGAGCTTTTGTCGAAGAGCAAGCCTGGTGATAAGTA
   501▶ GluCysGluSerGluGlyAlaAsnLysMetIleGluTyrLeuArgGluLeuLeuSerLysSerLysProGlyAspLysTy 1601 TGGAAGTTACGTCCTCCAGTTTGCCGATGATTATACATACACTGATCCTGTAGATGGAAGTGTAGTATCAAAACAAGGGG
   527▶ rGlySerTyrValLeuGlnPheAlaAspAspTyrThrTyrThrAspProValAspGlySerValValSerLysGlnGlyV 1681 TTCCGTTTGTTTTCACCGATGGTTCAAGAATTATTTACCGTTTATCAGGAACGGGTTCTGCTGGTGCAACTGTTAGAGTG
   554▶ alArgPheValPheThrAspGlySerArgIleIleTyrArgLeuSerGlyThrGlySerAlaGlyAlaThrValArgVal 1761 TATATCGAACAGTTTGAACCAGATGTTTCTAAACACGACGTCGATGCTCAAATTGCCTTGAAACCATTAATAGATTTAGC
   581▶ TyrIleGluGlnPheGluProAspValSerLysHisAspValAspAlaGlnIleAlaLeuLysProLeuIleAspLeuAl 1841 ATTATCTGTTTCAAAGCTCAAAGACTTCACAGGGA
   607▶ aLeuSerValSerLysLeuLysAspPheThrGly
```

```
                                                           HindIII (55)
   1  GATTGCTGATATTCCCGATGTTGACTTATCAAATGTTGGAGTTACGAAATTCGGAAGCTTCAGTGTGGAAGTAATAGAC
   1▶ IleAlaAspIleProAspValAspLeuSerAsnValGlyValThrLysPheGlySerPheSerValGluValIleAsp 80  CCAGTTTCTGATTACCTGGAGTTATTGGAGACAGTGTTCGATTTTCAGCTAATCAAAAGTCTTATTTCACGGCCAGATT
  27▶ ProValSerAspTyrLeuGluLeuLeuGluThrValPheAspPheGlnLeuIleLysSerLeuIleSerArgProAspP
                  SphI (181)
 159  TTAGGTTTACATTTGATGCCATGCATGCAGTTGCCGGTGCTTATGCAACACCCATTTTCGTTGATAAACTTGGTGCTAG
  53▶ heArgPheThrPheAspAlaMetHisAlaValAlaGlyAlaTyrAlaThrProIlePheValAspLysLeuGlyAlaSe 238  TCCGGATTCAATTTCAAATGGAATACCTTTGGAAGATTTTGGACATGGTCATCCTGATCCTAATCTAACATACGCAAAG
  79▶ rProAspSerIleSerAsnGlyIleProLeuGluAspPheGlyHisGlyHisProAspProAsnLeuThrTyrAlaLys 317  GATCTTGTCAATATTATGTATGCTGAAAACGGACCTGATTTTGGTGCCGCTAGTGATGGTGATGGTGATAGAAATATGA
 106▶ AspLeuValAsnIleMetTyrAlaGluAsnGlyProAspPheGlyAlaAlaSerAspGlyAspGlyAspArgAsnMetI 396  TTTTGGGAACAAGTTTCTTCGTAACTCCTTCAGACTCTGTAGCCGTTATTGCAGCCAATGCAAAAGAAGCGATTCCGTA
 132▶ leLeuGlyThrSerPhePheValThrProSerAspSerValAlaValIleAlaAlaAsnAlaLysGluAlaIleProTy
                                                                   XbaI (526)
 475  CTTTAAGGACAGTATCAAGGGTCTTGCACGATCAATGCCGACAAGCGGTGCTCTAGATAGAGTTGCTGAAAAGTTGAAC
 158▶ rPheLysAspSerIleLysGlyLeuAlaArgSerMetProThrSerGlyAlaLeuAspArgValAlaGluLysLeuAsn 554  CTCCCTTTTTTTGAGGTTCCCACTGGTTGGAAATTCTTTGGTAATCTTATGGATGCTGGAAATCTGTCGATTTGCGGGG
 185▶ LeuProPhePheGluValProThrGlyTrpLysPhePheGlyAsnLeuMetAspAlaGlyAsnLeuSerIleCysGlyG
                                                     ▲
 633  AAGAGAGTTTTGGAACAGGTTCTGACCACATTCGTGAGAAAGACGGAATCTGCTTGGCTTTCGATTATTGCTCACCGCA
 211▶ luGluSerPheGlyThrGlySerAspHisIleArgGluLysAspGlyIleCysLeuAlaPheAspTyrCysSerProGl 712  ACAAAGACACGAAACCAGGGGAGAAATTGGTCTCTGTGTCTGATGTTGTGAAGGAGCATTGGGCAACCTATGGTAGAAA
 237▶ nGlnArgHisGluThrArgGlyGluIleGlyLeuCysVal
              XbaI (798)
 791  TTTCTTTTCTAGATACGATTACGAGGAATGTGAATCCGAAGGCGCAAATAAGATGATAGAGTACCTACGAGAGCTTTTG 870  TCGAAGAGCAAGCCTGGTGATAAGTATGGAAGTTACGTCCTCCAGTTTGCCGATGATTATACATACACTGATCCTGTAG 949  ATGGAAGTGTAGTATCAAAACAAGGGGTTCGGTTTGTTTTCACCGATGGTTCAAGAATTATTTACCGTTTATCAGGAAC

1028  GGGTTCTGCTGGTGCAACTGTTAGAGTG
      ◀
```

Figure 14

```
   1 CACTGTTACAGACTCGATCAATGGCTTTCTGTTACAGACTCGACAACTTCATCATCTCTGCGTTTAAACCCAAACACTCA
     1▶MetAlaPheCysTyrArgLeuAspAsnPheIleIleSerAlaPheLysProLysHisSer
  81 AATGTCCCACTTTCAATTCATCATTCATCATCCAATTTTCCTTCTTTCAAAGTTCAAAACTTTCCTTTCAGGGTTCGCTA
    21▶AsnValProLeuSerIleHisHisSerSerSerAsnPheProSerPheLysValGlnAsnPheProPheArgValArgTy
 161 TAATTCAGCTATTAGAGCCACTTCGTCTTCCTCTTCTACTCCCACAACCATTGCAGAACCTAATGACATTAAGATTAACT
    47▶rAsnSerAlaIleArgAlaThrSerSerSerSerSerThrProThrThrIleAlaGluProAsnAspIleLysIleAsnS
                                                                                      KpnI (276)
 241 CTATTCCTACTAAACCTATTGAAGGACAAAAAACTGGTACCAGTGGCCTAAGAAAAAAGGTGAAAGTGTTTAAGCAAGAA
    74▶erIleProThrLysProIleGluGlyGlnLysThrGlyThrSerGlyLeuArgLysLysValLysValPheLysGlnGlu
 321 AATTACCTTGCAAATTGGATTCAGGCACTGTTTAATTCGTTGCCGCCGGAGGATTACAAGAATGGATTGTTGGTTTTGGG
   101▶AsnTyrLeuAlaAsnTrpIleGlnAlaLeuPheAsnSerLeuProProGluAspTyrLysAsnGlyLeuLeuValLeuGl
 401 AGGCGATGGTCGATACTTCAATAAAGAAGCTGCACAGATAATAATCAAGATTGCTGCTGGAAATGGTGTTGGAAAAATTC
   127▶yGlyAspGlyArgTyrPheAsnLysGluAlaAlaGlnIleIleIleLysIleAlaAlaGlyAsnGlyValGlyLysIleL
 481 TGGGTTGGGAAGGAAGGGATATTGTCAACGCCAGCCGTTTCTGCTGTGATAAGGAAGAGAGAGGCAAATGGTGGGTTTATC
   154▶euValGlyLysGluGlyIleLeuSerThrProAlaValSerAlaValIleArgLysArgGluAlaAsnGlyGlyPheIle
 561 ATGAGTGCGAGCCATAACCCTGGTGGACCTGAATATGATTGGGGTATTAAGTTTAATTACAGTAGCGGACAACCTGCACC
   181▶MetSerAlaSerHisAsnProGlyGlyProGluTyrAspTrpGlyIleLysPheAsnTyrSerSerGlyGlnProAlaPr
                                                                                      ClaI (677)
 641 AGAATCCATCACCGACAAGATTTACGGAAACACCCTATCGATTTCTGAGATAAAGATTGCTGATATTCCCGATGTTGACT
   207▶oGluSerIleThrAspLysIleTyrGlyAsnThrLeuSerIleSerGluIleLysIleAlaAspIleProAspValAspL
                                                                                      HindIII (749)
 721 TATCAAATGTTGGAGTTACGAAATTCGGAAGCTTCAGTGTGGAAGTAATAGACCCAGTTTCTGATTACCTGGAGTTATTG
   234▶euSerAsnValGlyValThrLysPheGlySerPheSerValGluValIleAspProValSerAspTyrLeuGluLeuLeu
                                                                                      SphI (875)
 801 GAGACAGTGTTCGATTTTCAGCTAATCAAAAGTCTTATTTCACGGCCAGATTTTAGGTTTACATTTGATGCCATGCATGC
   261▶GluThrValPheAspPheGlnLeuIleLysSerLeuIleSerArgProAspPheArgPheThrPheAspAlaMetHisAl
 881 AGTTGCCGGTGCTTATGCAACACCCATTTTCGTTGATAAACTTGGTGCTAGTCCGGATTCAATTTCAAATGGAATACCTT
   287▶aValAlaGlyAlaTyrAlaThrProIlePheValAspLysLeuGlyAlaSerProAspSerIleSerAsnGlyIleProL
 961 TGGAAGATTTTGGACATGGTCATCCTGATCCTAATCTAACATACGCAAAGGATCTTGTCAATATTATGTATGCTGAAAAC
   314▶euGluAspPheGlyHisGlyHisProAspProAsnLeuThrTyrAlaLysAspLeuValAsnIleMetTyrAlaGluAsn
1041 GGACCTGATTTTGGTGCCGCTAGTGATGGTGATGGTGATAGAAATATGATTTTGGGAACAAGTTTCTTCGTAACTCCTTC
   341▶GlyProAspPheGlyAlaAlaSerAspGlyAspGlyAspArgAsnMetIleLeuGlyThrSerPhePheValThrProSe
1121 AGACTCTGTAGCCGTTATTGCAGCCAATGCAAAAGAAGCGATTCCGTACTTTAAGGACAGTATCAAGGGTCTTGCACGAT
   367▶rAspSerValAlaValIleAlaAlaAsnAlaLysGluAlaIleProTyrPheLysAspSerIleLysGlyLeuAlaArgS
                                                                                      XbaI (1220)
1201 CAATGCCGACAAGCGGTGCTCTAGATAGAGTTGCTGAAAAGTTGAACCTCCCTTTTTTTGAGGTTCCCACTGGTTGGAAA
   394▶erMetProThrSerGlyAlaLeuAspArgValAlaGluLysLeuAsnLeuProPhePheGluValProThrGlyTrpLys
1281 TTCTTTGGTAATCTTATGGATGCTGGAAATCTGTCGATTTGCGGGGAAGAGAGTTTTGGAACAGGTTCTGACCACATTCG
   421▶PhePheGlyAsnLeuMetAspAlaGlyAsnLeuSerIleCysGlyGluGluSerPheGlyThrGlySerAspHisIleAr
1361 TGAGAAAGACGGAATCTGGAATGTGAATCCGAAGGCGCAAATAAGATGATAGAGTACCTACGAGAGCTTTTGTCGAAGA
   447▶gGluLysAspGlyIleTrpAsnValAsnProLysAlaGlnIleArg
1440 GCAAGCCTGGTGATAAGTATGGAAGTTACGTCCTCCAGTTTGCCGATGATTATACATACACTGATCCTGTAGATGGAAGT
1520 GTAGTATCAAAACAAGGGGTTCGGTTTGTTTTCACCGATGGTTCAAGAATTATTTACCGTTTATCAGGAACGGGTTCTGC
1600 TGGTGCAACTGTTAGAGTGTATATCGAACAGTTTGAACCAGATGTTTCTAAACACGACGTCGATGCTCAAATTGCCTTGA
1680 AACCATTAATAGATTTAGCATTATCTGTTTCAAAGCTCAAAGACTTCACAGGGA
```

STARCHLESS VARIETY OF *PISUM SATIVUM* HAVING ELEVATED LEVELS OF SUCROSE

RELATED APPLICATION INFORMATION

This application is a 371 of PCT/US98/25912 filed on Dec. 7, 1998, which claims priority from U.S. Ser. No. 09/015,711 filed on Jan. 29, 1998, now U.S. Pat. No. 6,127,605, which is a continuation-in-part of U.S. Ser. No. 08/986,616 filed on Dec. 8, 1997, now abandoned.

TECHNICAL FIELD OF THE INVENTION

The present invention relates to a *Pisum sativum* variety that contains a recessive gene that produces highly wrinkled seed having a low starch content. Additionally, the present invention relates to nucleotide sequences for said recessive gene and methods for using said nucleotide sequences in site-specific recombination.

BACKGROUND OF THE INVENTION

The garden pea (*Pisum sativum* L.) is a commercially important food crop and the immature seed of the garden pea ("peas") are widely consumed. There are a large number of genes that affect starch or carbohydrate synthesis in peas. The first reported and best described gene is the r gene (see White, O. E., *Proceedings of the American Philosophical Society*, 56: 487–588). The r mutant is believed to have occurred spontaneously at the beginning of the seventeenth century (see Lamprecht, H., *Agri. Hortique Genetica* 14: 1–4 (1956)) and its mature, dry seed has a wrinkled appearance (hence "r", derived from the Latin, rugosus meaning "wrinkled or shriveled"). Wrinkling of mature seed was one of the characteristics used by Mendel in experiments which led him to formulate his laws of inheritance. (see Mendel, G., *Verhandlungen des Naturforschenden Vereinds in Brünn* 4: 3–47 (1865)).

Recessive alleles at the r locus not only have a profound effect on the shape of the seed, but also have numerous effects at all levels of seed development. Wang, T. L., et al., *Seed Science Research* 1:3–14 (1991). Specifically, seeds of the r mutant contain a lower proportion of starch than the wildtype (about 30% dry weight as opposed to about 50%) with the starch composition being altered to contain a higher proportion of amylose and a small proportion of amylopectin (with about 70% of dry weight of the starch of mutant seeds being amylose as opposed to 38% of the wildtype starch). For a long period of time, the molecular basis of the mutation was not clear. The difference in the level and composition of starch in the seed led several investigators to examine the various enzymes of starch biosynthesis. Id. Early studies indicated that the mutation was likely to be in the starch branching enzyme and this was confirmed when it was shown, using a pair of lines near-isogenic except for genes at the r locus that rr embryos lacked one form of the starch-branching enzyme, which is frequently referred to as "SBE1". Subsequently, it was shown that the mutant was caused by a transposon-like insertion in the gene encoding SBE1. Id.

A second recessive rugosus locus termed "rb" is also known. Mutants homozygous recessive at this locus exhibit a wrinkled seed phenotype similar to that of rr plants. However, the amount of starch and its composition in the rb mutant are different than that of the r mutant. Specifically, seed of the r mutant contains about 30% dry weight of starch, of which about 70% is amylose. Seed of the rb mutant contains about 36% dry weight of starch, of which about 23% is amylose. The rb mutation has been found to result in reduced activity in the enzyme ADP glucose pyrophosphorylase. Purification of the enzyme and western blot experiments have revealed the absence of one of the four polypeptide subunits present in the wildtype enzyme.

WO 98/01574 describes *Pisum sativum* varieties which contain a mutation referred to as "rug3". Plants containing the rug-3 mutation produce wrinkled seeds having low levels of starch, high levels of sucrose, as well as a high protein and lipid content. The rug-3 mutation has been found to be associated with a reduction in the activity of the enzyme plastid phosphoglucomutase (hereinafter "PGM"). According to WO 98/01574, pea seeds containing the rug-3 mutation have a sucrose content of greater than 6% by weight of the total weight of the seed as harvested at a tenderometer reading exceeding 120 tenderometer units.

The rug-3 mutation described in WO 98/01574 was induced via a mutagenesis program. Twenty thousand phenotypically round genetically wildtype (RR) seeds (referred to as "M1" seed) were treated with ethyl methanesulphonate or N-methyl-N-nitrosourea, which are known mutagens. M1 seed gave rise to M1 plants bearing M2 seed. M2 seed gave rise to M2 plants bearing M3 seed. M3 seeds were analyzed for storage product content. Seeds which exhibited a wrinkled appearance were selected from the M3 generation. These seeds were found to contain a wide range of starch, from 0–60% as a proportion of the dry weight of the mature seed. Within the starch of these seeds, the amylose content ranged from 0–80%. Also, the lipid content of the peas ranged from about 1 to about 8% of the dry weight and protein ranged from about 24 to about 48%. WO 98/01574 does not contain any information characterizing the rug-3 mutant except to describe how this mutation was induced via a mutagen program. Additionally, WO 98/01574 does not contain any information that distinguishes the DNA sequence of the rug-3 mutant from that of the wildtype and contains no information on effects on alcohol insoluble solids content.

WO 98/01574 also describes the isolation and characterization of the nucleotide sequence for wildtype pea plastid phosphoglucomutase. According to WO 98/01574, this nucleotide sequence can be introduced into a plant via recombinant DNA technology to produce transgenic plants in which the plastid PGM gene expression is down regulated or inactivated in developing seeds.

Sweetness in peas, associated with increased sugar content, is generally prized by consumers, who perceive that sweeter peas have a better flavor. Thereupon, because peas are such an important food crop, there is a need in the art for peas having an increased sweetness.

SUMMARY OF THE INVENTION

The present invention relates to a new variety of *Pisum sativum*, which is resistant to Fusarium Wilt Fungus and Powdery Mildew Fungus and which contains within its genome, a homozygous recessive gene, referred to as the bsg gene. It has been determined that the bsg gene contains a mutation in an intron in a 3' splice site of the gene. More specifically, the bsg gene has the genomic nucleotide sequence shown in Sequence ID NO:1 and contains a mutation at nucleotide 1548 at the 3' splice site dinucleotide AG, where nucleotide A is replaced with nucleotide T.

A *Pisum sativum* variety that contains the bsg gene within its genome produces peas (known in the art as immature seeds) which exhibit a lower level of starch, an elevated level of sucrose and a decreased level of alcohol insoluble solids when compared with peas produced from a *Pisum sativum* variety that does not contain the bsg gene homozygous within its genome.

Additionally, the present invention contemplates a *Pisum sativum* variety which contains a homozygous bsg gene within its genome. The bsg gene has the nucleotide sequence shown in SEQ ID NO:1 and contains a mutation in an intron at nucleotide 1548 at the 3' splice site dinucleotide AG, where nucleotide A is replaced with nucleotide T.

The peas of the present invention contain from about 6.0 to about 7.5 percent fresh weight of sucrose when measured at a tenderometer value of from about 90 to about 110 and from about 6.5 to about 8.0 percent by weight of alcohol insoluble solids when measured at a tenderometer value of about 105. Moreover, the peas of the present invention contain from about 5 to about 30 percent fresh weight more sucrose than peas produced from a *Pisum sativum* variety that does not contain the bsg gene homozygous within its genome. Additionally, the peas of the present invention exhibit twenty (20) percent less alcohol insoluble solids when compared with peas from a *Pisum sativum* that does not contain the bsg gene homozygous within its genome.

Additionally, the present invention relates to a process for producing peas of a *Pisum sativum* variety that contain higher levels of sucrose and lower levels of alcohol insoluble solids than peas from a *Pisum sativum* variety that does not contain the bsg gene homozygous within its genome. The said process involves crossing a *Pisum sativum* variety or line that contains the bsg gene homozygous within its genome with a second *Pisum sativum* variety or line that contains the bsg gene homozygous within its genome, collecting the resulting mature seeds, planting the mature seeds, growing the mature seeds into *Pisum sativum* plants, selecting *Pisum sativum* plants with desirable phenotypic traits; allowing the plants to self-pollinate until a uniform line is produced, allowing the *Pisum sativum* line to self-pollinate, selecting plants with desirable phenotypes and collecting the resulting peas (which are also referred to as "mature seeds").

In another embodiment, the process involves crossing a *Pisum sativum* variety or line that contains the bsg gene homozygous within its genome with a second *Pisum sativum* variety or line which does not contain the bsg gene within its genome, collecting dry, mature seeds, planting the collected dry, mature seeds, growing the mature seeds into *Pisum sativum* plants, allowing the plants to self-pollinate, collecting the resulting dry, mature seeds, selecting highly wrinkled mature seeds that do not contain organized starch grains and which do not stain purple when treated with a solution of iodine and potassium iodide, planting said highly wrinkled mature seeds, growing the mature seeds into *Pisum sativum* plants, selecting plants with desirable phenotypic traits, allowing the plants to self-pollinate until a uniform *Pisum sativum* line is produced, allowing the *Pisum sativum* line selected to self-pollinate, and collecting the resulting peas. The *Pisum sativum* variety or line that does not contain the bsg gene within its genome can contain any combination of the genes such as the r, rb, R or Rb homozygous within its genome. The peas produced by the process of the present invention contain from about 6.0 to about 7.5 percent fresh weight of sucrose when measured at a tenderometer value of from about 90 to about 110 and from about 6.5 to about 8.0 percent by weight of alcohol insoluble solids when measured at a tenderometer value of about 105.

The present invention also contemplates a process of producing highly wrinkled mature seed of a *Pisum sativum* variety that contains the bsg gene within its genome. In one embodiment the process involves crossing a *Pisum sativum* variety or line that contains the bsg gene within its genome with a second *Pisum sativum* variety or line that contains the bsg gene within its genome and collecting the resulting mature seeds.

In another embodiment, the process involves crossing a *Pisum sativum* variety or line that contains the bsg gene within its genome with a *Pisum sativum* variety or line that does not contain the bsg gene within its genome, collecting mature seeds, planting the collected mature seeds, growing the mature seeds into *Pisum sativum* plants, allowing the plants to self-pollinate, collecting mature seeds, selecting highly wrinkled seeds that do not contain organized starch grains, planting said mature seeds and growing the seeds into *Pisum sativum* plants, selecting plants with desirable phenotypic traits, allowing the plants to self-pollinate until a uniform *Pisum sativum* line is produced, allowing the *Pisum sativum* line to self-pollinate and collecting the mature seeds.

The present invention also contemplates *Pisum sativum* varieties grown from the mature seed described above and peas harvested from said varieties.

In another embodiment, the present invention contemplates a DNA molecule containing a nucleotide sequence which encodes plastid phosphoglucomutase, where the nucleotide sequence contains at least one mutation in an intron. The mutation in the intron prevents the excision of the intron from a primary transcript during post-transcriptional modification of the transcript and produces at least one aberrant mRNA for translation. Preferably, the mutation is a mutation in a 3' splice site in the intron. Most preferably, the mutation is in a dinucleotide AG, where the nucleotide A is replaced by nucleotide T. This DNA molecule can be isolated and purified and inserted into an expression vector containing the DNA molecule, a promoter and a polyadenylation signal. In this vector, the promoter is operably linked to the DNA molecule and the DNA molecule is operably linked to the polyadenylation signal. The promoter may be the cauliflower mosaic virus 35S promoter and the polyadenylation signal may be the polyadenylation signal of the cauliflower mosaic 35S gene. Bacterial cells, such as *Agrobacterium tumefaciens* and *Agrobacterium rhizogenes* cells, and plant cells may be transformed with this vector.

In yet another embodiment, the present invention relates to a plant which contains a gene encoding plastid phosphoglucomutase within its genome, where the gene contains at least one mutation in an intron. The mutation in the intron prevents the excision of the intron from a primary transcript during post-transcriptional modification of the transcript and produces at least one aberrant mRNA for translation. The plant containing such a mutated gene may be a monocot or a dicot. Preferably, the mutation is a mutation in a 3' splice site in the intron. Most preferably, the mutation is in a dinucleotide AG, where the nucleotide A is replaced by nucleotide T.

In yet another embodiment, the present invention contemplates an isolated and purified DNA molecule having the nucleotide sequence shown in SEQ ID NO:1 as well as an expression vector containing this DNA molecule, a promoter and a polyadenylation signal. In this vector, the promoter is operably linked to the DNA molecule and the DNA molecule is operably linked to the polyadenylation signal. The promoter may be the cauliflower mosaic virus 35S promoter and the polyadenylation signal may be the polyadenylation signal of the cauliflower mosaic 35S gene. Bacterial cells, such as *Agrobacterium tumefaciens* and *Agrobacterium rhizogenes* cells, and plant cells may be transformed with this vector.

Finally, in yet another embodiment, the present invention contemplates a method of altering the level of plastid phosphoglucomutase expressed in a plant. The method involves transforming plant cells with a vector. The vector contains a promoter, a polyadenylation signal and DNA molecule having either (1) the nucleotide sequence of SEQ ID NO:1; or (2) a nucleotide sequence encoding plastid phosphoglucomutase where the nucleotide sequence contains at least one nucleotide which prevents the excision of at least one intron from a primary transcript during post-transcriptional modification of the transcript and which produces at least one aberrant mRNA for translation. The promoter is operably linked to the DNA molecule and the DNA molecule is operably linked to the polyadenylation signal.

The second step of the method involves regenerating plant cells to provide a differentiated plant. The final step of the method involves identifying a transformed plant having an altered level of plastid phosphoglucomutase expressed in that plant.

BRIEF DESCRIPTION OF THE DRAWINGS

FIG. 1 shows starch granules from three different types of dry, mature *Pisum sativum* seeds.

FIG. 6 shows part of the genomic sequence of plastid PGM from a Frimousse introgressed-bsg variety (hereinafter referred to as the "mutant") (SEQ ID NO:1). Exons are shown in bold.

FIG. 7 shows part of the genomic sequence of the smooth-seed *Pisum sativum* variety called "Frimousse" (hereinafter referred to as the "wildtype") (SEQ ID NO:2). Exons are shown in bold.

FIG. 9 shows the nucleotide sequence of wildtype plastid phosphoglucomutase (reported in WO 98/01574) the primers PGM-Fp (CACTGTTACA GACTCGATCA ATGG-SEQ ID NO:3), PGM-F91 (CAGACTCGAC AACTTCATCA TCTC-SEQ ID NO:4), PGM-Fb (GATTGCTGAT ATTC-CCGATG TTGA-SEQ ID NO:5), PGM-F827 (GACCCAGTTT CTGATTACCT GGAG-SEQ ID NO:6), PGM-Rg (CATGCATGGCATCAAATGTA AACC-SEQ ID NO:7), PGM-R1262 (GCATTGATCG TGCAAGA-CCCTTGA-SEQ ID NO:8), PGM-R1816 (CACTCTAACA GTTGCACCAG CAGA-SEQ ID NO:9) AND PGM-RF (TCCCTGTGAA GTCTTTGAGC TTTG-SEQ ID NO:10) which were used in PCR to amplify PGM cDNA from the wildtype and mutant poly(A)+seed.

FIG. 11 shows the nucleotide and corresponding amino acid sequence of plastid PGM cDNA from the wildtype (SEQ ID NOS:13 and 14).

FIG. 12 shows the nucleotide and corresponding amino acid sequence of plastid PGM cDNA1 from the mutant (SEQ ID NOS:15 and 16).

FIG. 13 shows the nucleotide and corresponding amino acid sequence of plastid PGM cDNA2 from the mutant (SEQ ID NOS:17 and 18).

FIG. 14 shows the nucleotide and corresponding amino acid sequence of plastid PGM cDNA3 from the mutant (SEQ ID NOS:19 and 20).

DETAILED DESCRIPTION OF THE INVENTION

Sequence Listing

The present application also contains a sequence listing that contains 21 sequences. The sequence listing contains nucleotide sequences and amino acid sequences. For the nucleotide sequences, the base pairs are represented by the following base codes:

| Symbol | Meaning |
|--------|---------|
| A | A; adenine |
| C | C; cytosine |
| G | G; guanine |
| T | T; thymine |
| U | U; uracil |
| M | A or C |
| R | A or G |
| W | A or T/U |
| S | C or G |
| Y | C or T/U |
| K | G or T/U |
| V | A or C or G; not T/U |
| H | A or C or T/U; not G |
| D | A or G or T/U; not C |
| B | C or G or T/U; not A |
| N | (A or C or G or T/U) |

The amino acids shown in the application are in the L-form and are represented by the following amino acid-three letter abbreviations:

| Abbreviation | Amino acid name |
|---|---|
| Ala | L-Alanine |
| Arg | L-Arginine |
| Asn | L-Asparagine |
| Asp | L-Aspartic Acid |
| Asx | L-Aspartic Acid or Asparagine |
| Cys | L-Cysteine |
| Glu | L-Glutamic Acid |
| Gln | L-Glutamine |
| Glx | L-Glutamine or Glutamic Acid |
| Gly | L-Glycine |
| His | L-Histidine |
| Ile | L-Isoleucine |
| Leu | L-Leucine |
| Lys | L-Lysine |
| Met | L-Methionine |
| Phe | L-Phenylalanine |
| Pro | L-Proline |
| Ser | L-Serine |
| Thr | L-Threonine |
| Trp | L-Tryptophan |
| Tyr | L-Tyrosine |
| Val | L-Valine |
| Xaa | L-Unknown or other |

Description of the Pea Varieties Containing the bsg Gene

The present invention relates to a novel garden variety of pea, *Pisum sativum*, that contains within its genome, a homozygous recessive gene, referred to as "bsg" (bsg referring to "blown starch grain"). As used herein, the term "genome" refers to the entire hereditary material (DNA) in a cell which is composed of one or more chromosomes.

It is well known in the art that peas are the immature seeds of a *Pisum sativum* variety. Peas or immature seeds typically do not exhibit a wrinkled appearance, but rather a smooth, round appearance. These peas contain the R gene as the dominant allele. Peas or immature seeds are consumed by individuals as food. Mature seeds of a *Pisum sativum* variety are dry seeds. Mature seed exhibits a wrinkled appearance if it contains the r or rb genes or bsg gene within its genome. Mature seeds are used for planting and produce *Pisum sativum* varieties.

The *Pisum sativum* variety of the present invention contains a homozygous bsg gene within its genome and produces mature seeds which are highly wrinkled, have a very low starch content and high levels of sucrose. The mature seeds of the present invention also contain a homozygous bsg gene within their genome and contain few, if any, organized starch granules when examined under a microscope. Instead of containing starch granules, mature seeds of the present invention contain granular material of unknown composition.

Figure 1A:
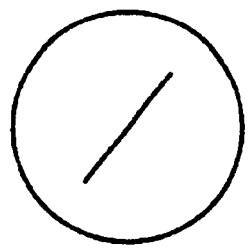
FIG. 1*a* shows the starch granules from a smooth seed which contain the R gene homozygous within its genome.
Figure 1B:
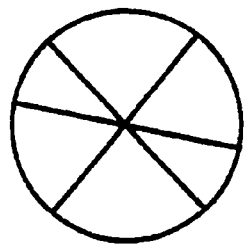
FIG. 1*b* shows the starch granules from a wrinkled seed which contains a r gene homozygous within its genome.
Figure 1C:
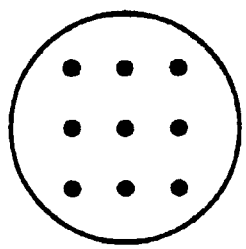
FIG. 1*c* shows the near absence of starch granules and the presence of granular material of unknown composition in mature seed containing a homozygous bsg gene.
Figure 2:
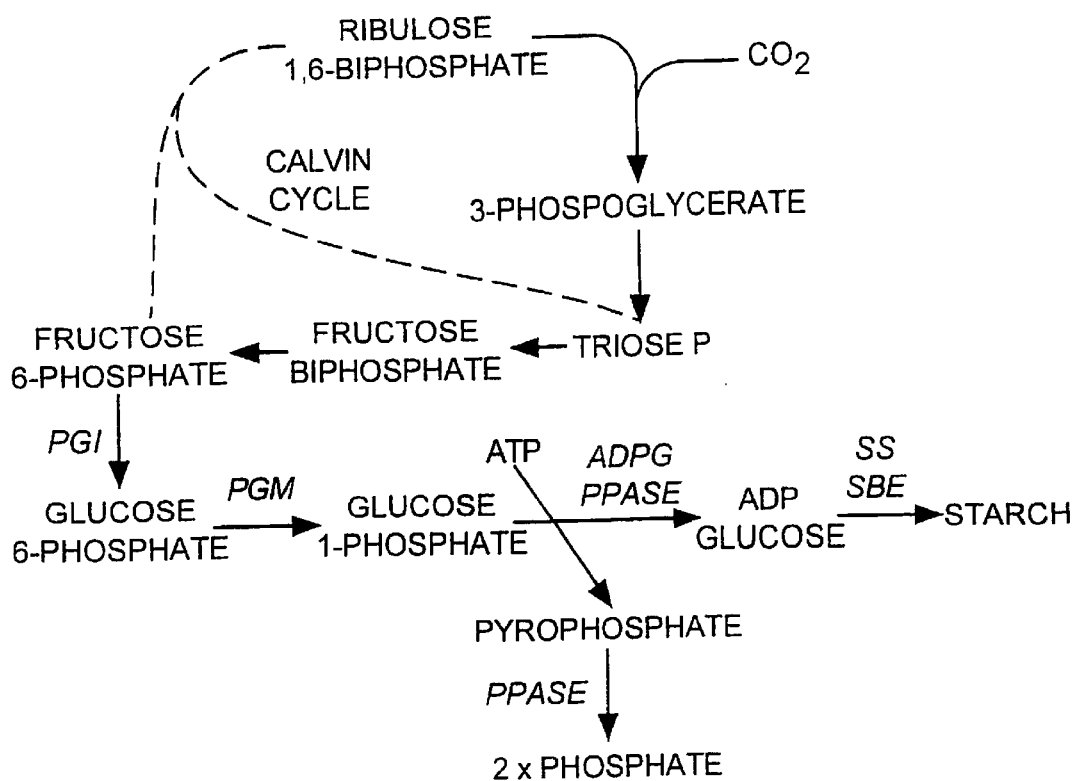
FIG. 2 shows starch biosynthesis in a chloroplast.
Figure 3:
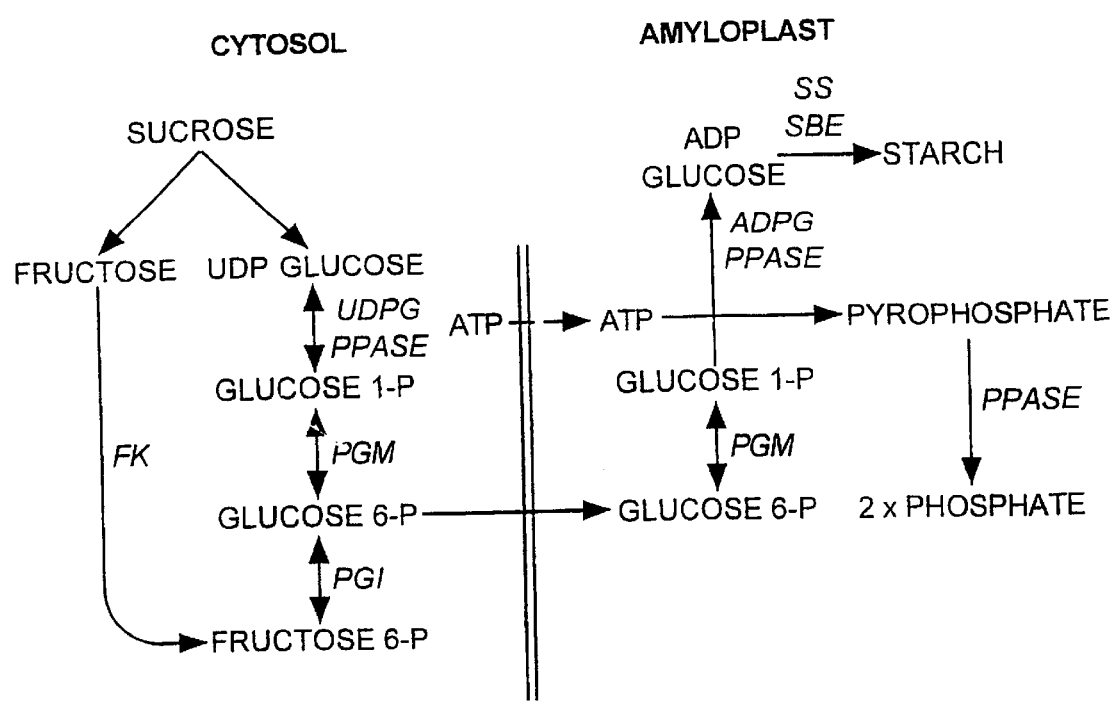
FIG. 3 shows starch biosynthesis in an amyloplast.

FIG. 1 demonstrates the appearance under a microscope of starch granules in various types of mature *Pisum sativum* seeds. FIG. 1a shows the appearance of starch granules in smooth mature seeds that contain the R gene homozygous or heterozygous with their genome. These mature seeds have entire starch granules and do not contain the r or bsg genes homozygous within their genome. When the mature seeds shown in FIG. 1a are treated with a solution of iodine and potassium iodide, the mature seeds stain purple indicating the presence of starch. FIG. 1b shows the appearance of the starch granules in a wrinkled mature seed that contains the r gene homozygous within its genome. The starch granules in the wrinkled mature seed containing the r gene homozygous exhibit a star shaped fracture pattern similar to that of a pie that has been scored into 5 or 6 pieces. FIG. 1c shows mature seed of the present invention that contains the bsg gene homozygous within its genome. As shown in FIG. 1c, mature seeds of the present invention contain few, if any, organized starch granules but instead contain granular material. When the mature seeds shown in FIG. 1c are treated with a solution of iodine and potassium iodide, the mature seeds fail to stain purple due to the near absence of starch.

The bsg mutation of the present invention was not induced by a mutagen program like the rug-3 mutation described in WO 98/01574. Instead, the bsg-mutation of the present invention is a natural mutation which was observed in a crop of smooth seed of a *Pisum sativum* variety containing the R gene as the dominant allele.

Due to the absence of starch, the *Pisum sativum* variety of the present invention also produces the peas or immature seeds that contain elevated levels of sucrose. As used herein, the term "sucrose" refers to the disaccharide composed of glucose and fructose.

The peas of the present invention contain the bsg gene homozygous within their genome and further contain from about 6.0 to about 7.5, preferably from about 6.2 to about 7.1 percent fresh weight of sucrose when measured at a tenderometer value of from about 90 to about 110. A tenderometer is a device that is used to measure the tenderness of peas, beans and broad beans. As used herein, the term "tenderometer value" refers to a measure of the force required to crush about 200 grams of peas using a tenderometer. Higher tenderometer values indicates more advanced maturity of the peas. Processed green peas are typically harvested at tenderometer values of from 90 to 120.

The peas of the present invention contain from about 5 to about 30 percent fresh weight, preferably from about 10 to about 20 percent fresh weight, more sucrose than peas produced from a *Pisum sativum* variety that does not contain the bsg gene homozygous within its genome, particularly wrinkled varieties of peas. As used herein, the term "wrinkled varieties of peas" refers to *Pisum sativum* that contain a homozygous r (rugosus) or homozygous rb gene within their genome, so that the appearance of the mature seed is wrinkled. Quantum is the sweetest variety of pea that is known by the inventor that contains the r gene homozygous within its genome. Quantum is commercially available under the Asgrow Brand, from Seminis Vegetable Seeds, Inc., the assignee of the present invention. Quantum peas contain from about 5.0 to about 6.2 percent fresh weight of sucrose.

Additionally, the peas of the present invention exhibit a depressed level of alcohol insoluble solids (AIS). Low AIS correlates with high product quality. The peas of the present invention contain from about 6.5 to about 8.0, preferably from about 7.0 to about 7.5 percent by weight of alcohol insoluble solids when measured at a tenderometer value of about 105. Moreover, the peas of the present invention exhibit about twenty (20) percent less AIS than peas from a *Pisum sativum* variety that does not contain the bsg gene homozygous within its genome (such as wrinkled varieties of peas). For example, peas of the present invention contain about twenty (20) percent less AIS than the peas produced by the variety Quantum.

Furthermore, the mature seeds of the present invention contain very little starch. More specifically, the seeds of the present invention contain from about 0.01 to 3.0 percent dry weight, preferably, from about 0.5 to 2.0 percent dry weight of starch.

Breeding History

The *Pisum sativum* variety of the present invention containing a homozygous bsg gene within its genome was developed as follows. In 1990, a wrinkled-seed mutant was discovered in a crop of Frimousse, which is a smooth-seed *Pisum sativum* variety that has no block in the conversion of sugar to starch (this mutant is designated "Frimousse introgressed-bsg"). This crop had been grown at a breeding station in Twin Falls, Id. This single mutant was discovered when the crop was undergoing seed-uniformity tests. Frimousse is commercially available under the Asgrow Brand, from Seminis Vegetable Seeds, Inc. A plant of this wrinkle-seed mutant was then crossed with the *Pisum sativum* variety Encore in a greenhouse in Twin Falls, Id. Encore is a full season, large sieve commercial *Pisum sativum* variety with dark green (freezer) berry color, good processed quality, and resistance to Powdery Mildew Fungus and Race 1 of the Fusarium Wilt Fungus. Dry, mature seed of Encore is available under the Asgrow Brand from Seminis Vegetable Seeds. One selection that resulted from this cross contained very little starch and was labeled M82.1.

In December 1991, seed of M82.1 and the variety Lazor were planted in a greenhouse in Twin Falls, Id. A cross was made between M82.1 and Lazor. Lazor is a late-season, large sieve *Pisum sativum* variety with dark green berry color and good processed quality and is resistant to Powdery Mildew Fungus and Race 1 of Fusarium Wilt Fungus. Dry, mature seed of Lazor is commercially available under the Asgrow brand from Seminis Vegetable Seeds, Inc., the assignee of the present invention. The resulting mature seed was collected and coded "BC0". In May 1992, seed of BC0 and Lazor were planted in the greenhouse described above and crossed. The resulting mature seed was collected and coded "BC1". In September 1992, seed of BC1 and Lazor were planted in the greenhouse described above and crossed. The resulting mature seed was collected and coded "BC2F1". In February 1993, seed of BC2F1 were planted in the same greenhouse and allowed to self-pollinate. The resulting mature seeds were collected and coded "BC2F2". In April 1993, several BC2F2 seeds that did not contain any organized starch grains were selected.

Later in 1993, the BC2F2 seeds selected above were then planted in a field in Twin Falls, Id. From the resulting population, individual lines containing the best horticultural characteristics were then selected and allowed to self-pollinate. Selection criteria included uniform emergence, short erect plant type, high productivity and uniformly of pod set. The resulting mature seeds were collected and coded "BC2F3". In April 1994, BC2F3 seed was planted in Twin Falls, Id.

From the resulting population, individual lines exhibiting the best horticultural characteristics were selected and allowed to self-pollinate. The resulting seed was collected and coded "BC2F4". In April 1995, BC2F4 seed was planted under the code name "R954593" in Twin Falls, Id. Observations made during the growing season indicated that the line was uniform and bred true. The resulting variety was allowed to self-pollinate and the resulting seed was collected and coded 8500017. In winter 1995, the 8500017 seed was planted in Guatemala and the resulting seed bulked for further trialing and increase.

Mature seeds of 8500017 developed as a result of the above breeding have been deposited under the Budapest Treaty with the American Type Culture Collection (hereinafter "ATCC"), 12301 Parklawn Drive, Rockville, Md., 20852 on Nov. 3, 1997 and have received accession number 209425. This deposit of 8500017 was made under the Budapest Treaty and will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has satisfied all the requirements of 37 C.F.R. Sections 1.801–1.809, including providing an indication of the viability of the sample. Furthermore, a Plant Variety Protection Certificate has been applied for on Feb. 19, 1998 with the United States Department of Agriculture and assigned PVP Application Number 9800121.

Processes for Developing *Pisum sativum* Varieties Containing Higher Levels of Sucrose The present invention also contemplates a process for developing *Pisum sativum* varieties that produce peas that contain higher levels of sucrose than peas produced by a *Pisum sativum* variety that does not contain the bsg gene within its genome. In one embodiment, the process involves crossing a *Pisum sativum* variety or line that contains the bsg gene homozygous within its genome with a second *Pisum sativum* variety or line that also contains the bsg gene homozygous within its genome, collecting the resulting mature seed, planting the mature seed, growing the mature seed into *Pisum sativum* plants, selecting *Pisum sativum* plants with desirable phenotypic traits, allowing the selected plants to self-pollinate until a uniform line is produced, allowing the *Pisum sativum* line to self-pollinate, and collecting the resulting peas.

In another embodiment, the process involves crossing a *Pisum sativum* variety or line that contains the bsg gene homozygous within its genome with a second *Pisum sativum* variety or line that does not contain the bsg gene within its genome and collecting the resulting mature seed. The *Pisum sativum* variety or line that does not contain the bsg gene within its genome can instead contain other genes or combination of genes within its genome. For example, the variety or line may contain the r or rb gene, or both, which produces wrinkled seed, or the R gene which produces smooth seed. The collected mature seed contains the bsg gene heterozygous within its genome. The collected mature seed are planted and allowed to grow. The *Pisum sativum* plants grown from said seed are allowed to self-pollinate. As a result of the self-pollination, the plants produce various types of dry, mature seeds that have different genes within their genomes. One type of mature seed that is produced is highly wrinkled. This seed contains virtually no organized starch grains and does not stain purple when treated with a solution of iodine and potassium iodine solution. This mature seed contains the bsg gene homozygous within its genome. The mature seed containing the bsg gene is selected, collected and planted. *Pisum sativum* plants having desirable phenotypic traits are selected and allowed to self-pollinate until a uniform *Pisum sativum* line is produced. The uniform line is allowed to self-pollinate and the resulting peas collected.

As used herein, the term "line" means a population of genetically and phenotypically similar seeds or plants.

As used herein, the term "uniform *Pisum sativum* line" means a population of genetically and phenotypically similar seeds or plants that may be reproduced by bulk increase without altering the descriptive characteristics of the population. A variety is a uniform that is increased for commerce.

The present invention also contemplates peas produced by any of the hereinbefore described processes. Peas produced pursuant to the above-mentioned processes contain from about 6.0 to about 7.5, preferably from about 6.5 to about 7.0 percent fresh weight sucrose when measured at a tenderometer value of from about 90 to about 110 and from about 6.5 to about 8.0, preferably from about 7.0 to about 7.5 percent by weight alcohol insoluble solids when measured at a tenderometer value of about 105. Moreover, peas produced by the process of the present invention also contain higher levels of sucrose than peas produced from a *Pisum sativum* variety that does not contain the bsg gene homozygous within its genome. Moreover, peas produced according to the process of the present invention contain from about 5 to about 30 percent fresh weight, preferably from about 10 to about 20 percent fresh weight, more sucrose than peas produced by a *Pisum sativum* variety that does not contain the bsg gene within its genome. Additionally, peas produced according to the process of the present invention contain about twenty (20) percent less AIS than peas produced from a *Pisum sativum* variety that does not contain the bsg gene within its genome.

The present invention also contemplates a process for producing highly wrinkled mature seed of a *Pisum sativum* variety that contains the bsg gene homozygous within its genome. In one embodiment, the process involves crossing a *Pisum sativum* variety or line that contains the bsg gene homozygous within its genome with a second *Pisum sativum* variety or line that contains the bsg gene homozygous within its genome and collecting the resulting mature seeds. The present invention also contemplates *Pisum sativum* varieties grown from said dry, mature seed and peas harvested from said varieties.

In a second embodiment, the process involves crossing a *Pisum sativum* variety or line that contains the bsg gene homozygous within its genome with a second *Pisum sativum* variety or line that does not contains the bsg gene homozygous within its genome and collecting the resulting mature seeds. After the mature seed is collected, it is planted and grown into plants which are allowed to self-pollinate. The resulting mature seed is collected and highly wrinkled mature seeds that do not contain any organized starch grains are selected. These mature seeds are planted and allowed to grow into *Pisum sativum* plants. *Pisum sativum* plants having desirable phenotypic traits are selected. These selected plants are allowed to self-pollinate until a uniform *Pisum sativum* line is produced. The uniform line is allowed to self-pollinate and mature seeds collected. The present invention also contemplates *Pisum sativum* varieties grown from said dry, mature seed and peas harvested from said varieties.

Molecular Characterization of the bsg Gene

*Pisum sativum* varieties containing the bsg gene have been found to exhibit a significant reduction in the activity of the enzyme plastid phosphoglucomutase (hereinafter referred to as "PGM") in leaves and cotyledons (see FIGS. 4 and 5). The significance of this lack of plastid PGM activity is that in the plastid, the conversion of glucose-6-phosphate to glucose-1-phosphate cannot occur. The importance of this reaction in the synthesis of starch is that glucose-1-phosphate is the substrate for the committed pathway of starch synthesis. Without a supply of glucose-1-phosphate, the synthesis of starch cannot take place. Sugar and starch metabolism are known to be related in plants. It is believed that an alteration in the levels of an enzyme involved in the starch synthesis pathway results in an alteration of the level of sugar in a plant and thus higher levels of sucrose in the seed (peas).

It has been discovered that *Pisum sativum* varieties containing the bsg gene contain a mutation in a 3' splice site in an intron in a gene encoding the plastid phosphoglucomutase. More specifically, the mutation is in the 3' splice site dinucleotide AG, where nucleotide A is replaced with nucleotide T.

Transcription is the synthesis of RNA on a DNA template by complementary base pairing within the nucleus of a cell. The RNA molecule initially transcribed from the DNA template is known as the "primary transcript". The primary transcript which is transcribed from the DNA contains "introns", which are frequently referred to as "intervening sequences." Introns are absent from the mature form of the primary transcript which is referred to as "messenger RNA" or "mRNA" in short. Introns are removed during post-transcriptional modification of the primary transcript. A number of events take place during the post-transcriptional modification of the primary transcript, one of which includes the removal of the introns and the splicing together of exons during a number of reactions which occur within a spliceosome. Once the post-transcriptional modifications are completed, a mature mRNA leaves the nucleus and enters the cytoplasm.

In the present invention, the mutation in the 3' splice site in an intron in a gene encoding the plastid phosphoglucomutase prevents the excision of this intron during post-transcriptional modification of the primary transcript. Because the intron is not excised from the primary transcript, it gives rise to three aberrant mRNAs. As used herein, the term "aberrant" means different from the correctly spliced wildtype plastid PGM mRNA by containing unexcised intron sequences or incorrectly excised exons. When translated, the aberrant mRNAs produces a plastid PGM polypeptide that is truncated and hence, shorter in length than the polypeptide produced by the wildtype, which is about 627 amino acids in length (See WO 98/01574 which reports the cloning of a polynucleotide sequence encoding the pea plastidical phosphoglucomutase wildtype having an amino acid sequence of about 627 amino acids). The alteration of this plastid PGM polypeptide is believed to be responsible for the significant reduction in activity of this enzyme in *Pisum sativum* varieties containing the bsg gene. This mutation of the bsg gene shall be more fully described below.

A portion of the plastid PGM genomic nucleotide sequence of the bsg mutant has been characterized and is shown in FIG. 6 and in SEQ ID NO:1. A portion of the plastid PGM genomic nucleotide sequence from a conventional, smooth-seed *Pisum sativum* variety, called "Frimousse", which is commercially available from Seminis Vegetable Seeds, Inc., the assignee of the present invention, has been characterized and is shown in FIG. 7 and SEQ ID NO:2. This conventional, smooth-seed *Pisum sativum* variety shall hereinafter be referred to as the "wildtype". In FIGS. 6 and 7, exons are shown in bold-faced type.

A comparison of the genomic nucleotide sequence of the wildtype with the genomic nucleotide sequence of the bsg mutant revealed a single mutation in one of the introns in the nucleotide sequence of plastid PGM in the bsg mutant. Specifically, in the bsg mutant, at nucleotide 1594, an A in the 3' splice site dinucleotide AG/ is replaced with a T (See asterisk in FIGS. 6 and 7). Splice sites are regions containing a few nucleotides that reside at the end of introns and function in excision and splicing reactions during the processing of transcripts from genes. The 3' splice site dinucleotide AG/ is invariant in naturally occurring higher plant introns (Simpson and Filipowicz *Plant Mol. Biol.* 32:1–41

(1996). It is known in maize, for example, that this same mutation, AG'TG, abolishes processing (see Carle-Urioste et al. *Plant Mol. Biol.* 26:1785–1795 (1994)).

This mutation in the 3' splice site results in three aberrant transcripts being produced during transcription. The largest transcript contains not only the intron with the mutated 3' splice site but a downstream intron as well. It is not clear why this downstream intron is retained. The retention of these two introns in this transcript results in a plastid PGM polypeptide which is immediately truncated by a termination codon near the 5' end of the first retained intron. This results in the loss of about 173 amino acids from the carboxyl terminal of the plastid PGM polypeptide. Northern analysis suggests that this first transcript is the major transcript which accumulates in the bsg mutant (see FIG. 8).

The second transcript is approximately the same size as the wildtype transcript, but is missing about the first 11 nucleotides of the exon directly downstream from the mutated intron. This results from the utilization of a cryptic AG 3' splice site dinucleotide in the downstream exon. As a result, a frame shift mutation is created and 23 amino acids are substituted from the wrong reading frame for the C-terminal 174 amino acid of plastid PGM.

The third transcript is smaller than the wildtype transcript due to a deletion of the 142 base pair exon immediately downstream from the mutated intron. This results from the substitution of the 3' splice site in the downstream intron for the mutated 3' spice site. As a result, a frameshift mutation is created and 9 amino acids are substituted for the C-terminal 173 amino acids of plastid PGM.

The modified plastid PGM polypeptide encoded by the nucleotide sequence of SEQ ID NO:1 and shown in FIG. 6 is believed to be responsible for the significant reduction in the activity of this enzyme in varieties containing this mutation.

It should be recognized that *Pisum sativum* varieties containing mutations in the plastid PGM gene in addition to the mutation described above in at the 3' splice site in the intron of the plastid PGM gene, as well as mutations in genes other than the plastid PGM gene, are also encompassed by this invention.

Moreover, it should further be recognized that the present invention encompasses any plant which contains one or more mutations in a gene encoding plastid phosphoglucomutase. Specifically, the gene must contain at least one mutation in one or more introns. The mutation must prevent the excision of one or more introns from a primary transcript during post-transcriptional modification of the transcript which results in the production of one or more aberrant mRNA molecules for translation. During translation, this aberrant mRNA produces a plastid PGM polypeptide which is either truncated or larger than the wildtype plastid PGM polypeptide. The types of plants encompassed by the present invention include "monocotyledonous" (often referred to as "monocots") or "dicotyledonous" (often referred to as "dicots") plants. A "monocotyledonous plant" refers to a plant whose seeds have only one cotyledon, or organ of the embryo that stores and absorbs food. A "dicotyledonous plant" refers to a plant whose seeds have two cotyledons.

DNA Molecules of the Present Invention

In another embodiment, the present invention relates to a DNA molecule. It is believed that the introduction into a plant of an expression vector containing an isolated and purified DNA molecule of the present invention (as defined hereinafter) inserted in either the sense or antisense direction will result in an alteration, specifically, a reduction, in the levels of expression of the native plastid PGM gene. For example, it is well known that gene expression in transgenic plants can be inhibited through the use of sense RNA transcribed from an exogenous template to downregulate the expression of specific plant genes (see Jorgensen, Keystone Symposium "Improved Crop and Plant Products through Biotechnology", Abstract X1-022 (1994)). The use of sense suppression is well known in the art and is described in Waterhouse, P M., et al., *Proc. Natl. Acad. Sci. U.S.A.*, 95(23):13959–64 (1998), Oue Q, et al., *Plant J.* 13(3):401–9 (1998) and Tsai C J., et al, *Plant Physiol.* 117(1):101–12 (1998), all incorporated herein by reference. It is well known, a cell manufactures protein by transcribing the DNA of the gene encoding that protein to produce RNA, which is then processed to messenger RNA (hereinafter referred to as "mRNA") and finally translated by ribosomes into protein. This process may be inhibited in the cell by the presence of antisense RNA. The term "antisense RNA" means an RNA sequence which is complementary to a sequence of bases in the mRNA in question in the sense that each base or them majority of bases in the antisense sequence (read in the 3' to 5' sense) is capable of pairing with the corresponding base (G with C, A with U) in the mRNA sequence read in the 5' to 3' sense. It is believed that this inhibition takes place by formation of a complex between the two complementary strands of RNA, thus preventing the formation of protein. How this works is uncertain: the complex may interfere with further transcription, processing, transport or translation, or degrade the mRNA, or have more than one of these effects. This antisense RNA may be produced in the cell by transformation of the cell with an appropriate DNA construct arranged to transcribe the non-template strand (as opposed to the template strand) of the relevant gene (or of a DNA sequence showing substantial homology therewith).

The use of antisense RNA to downregulate the expression of specific plant genes is well known. Reduction of gene expression has led to a change in the phenotype of the plant: either at the level of gross visible phenotypic difference, e.g., lack of anthocyanin production in flower petals of petunia leading to colorless instead of colored petals (see van der Krol et al., *Nature*, 333:866–869 (1988)); or at a more subtle biochemical level, for example, a change in the amount of polygalacturonase and reduction in depolymerization of pectin during tomato fruit ripening (see Smith et al., *Nature*, 334:724–726 (1988)).

Additionally, the DNA molecule of the present invention can be used in site-specific (also known as "homologous" and "gene targeting") recombination. It is known for example, that the presence of isogenic genomic sequences on an introduced DNA can be targeted to its own chromosomal locus and thus facilitate integration by site-specific recombination (Schaefer, D. G., et al., *Plant J.*, 11(6):1195–1206 (1997), herein incorporated by reference). Initially observed in *Saccharomyces cerevisiae*, this event is a prerequisite to application on the most sophisticated tools of reverse genetics, i.e. gene disruption and allele replaced. Id. With such approaches, virtually any cloned gene, even of unknown function, can be specifically mutagenized in vitro and re-introduced to its own chromosomal location in order to study its function. Id. The successful application of allele replacement depends on the ratio of homologous to illegitimate recombination events during integrative transformation. Id.

The DNA molecule of the present invention can be used in site-specific recombination to replace the wildtype nucleotide sequence to give rise to non-functional plastid PGM activity. Preferably, the nucleotide sequence of the DNA molecule used in such site-specific recombination exhibits a high homology with the target wildtype nucleotide sequence being replaced and contains about 50 to about 10,000 nucleotides, most preferably about 5,000 nucleotides. The techniques for site-specific recombination described in Risseeuw et al., *Plant J.*, 7(1):109–19 (1995), Offringa R., et al., *Proc. Natl. Acad. Sci. U.S.A.* 90(15):7346–50 (1993), Offringa R., et al., *EMBO J.*, 9(10):3077–84 (1990), Miao, Z H *Plant J.*, 7(2):359–65 (1995), all herein incorporated by reference, can be used to effect the site-specific recombination in the present invention.

The DNA molecule of the present invention comprises: (1) a nucleotide sequence comprising the nucleotide sequence shown in SEQ ID NO:1 which contains a mutation in an intron at nucleotide 1594 at the 3' splice site where an A is replaced by a T and sequences which are complementary to the sequence shown in SEQ ID NO:1; and (2) a nucleotide sequence encoding plastid phosphoglucomutase, where the nucleotide sequence contains at least one nucleotide which prevents the excision of at least one intron from a primary transcript during post-transcriptional modification of the transcript and which produces at least one aberrant mRNA for translation. The nucleotide sequences described herein can be isolated and purified from a natural substance such as a plant or can be artificially synthesized and then purified using techniques which are well known in the art. Additionally, the present invention also relates to an expression vector containing this DNA molecule, plant cells transformed with these vectors, and a process of reducing or suppressing plant plastid PGM expression by sense or antisense suppression in plants transformed with these vectors.

In another aspect, the present invention also contemplates naturally occurring allelic variations and mutations of the nucleotide sequences set forth above so long as the DNA molecule contains the hereinbefore described mutation.

In yet another aspect, the present invention also includes nucleotide sequences which hybridize under stringent hybridization conditions to the nucleotide sequences set forth above. Stringent hybridization conditions are well known in the art and define a degree of sequence identity greater than 70% to 80%.

The present invention also contemplates oligonucleotides from about 15 to about 50 nucleotides in length, which serve as primers and hybridization probes for the screening of DNA libraries and the identification of DNA or RNA molecules containing the mutation described hereinbefore and related sequences. Such primers and probes are characterized in that they will hybridize to the DNA molecule containing the hereinbefore described mutation contained within said DNA molecule. An oligonucleotide probe or primer contains a nucleotide sequence of at least 15 nucleotides that is identical to, nearly identical to or complementary to a contiguous sequence the DNA molecule shown in SEQ ID NO:1. Thus, where an oligonucleotide probe is 25 nucleotides in length, at least 15 of those nucleotides are identical or complementary to a sequence of the DNA molecule of the present invention.

In yet another aspect, the present invention also provides DNA constructs comprising all or part of the DNA molecule described above. A "construct" as used herein, is a DNA molecule comprising nucleic acid sequences not normally associated in nature, such as a prokaryotic sequence and a eukaryotic sequence. Typically, a "construct" comprises a vector, such as a plasmid, viral, and/or episomal origin, and a sequence to be transcribed.

Generally, the DNA construct will contain at least one promoter. The promoters may be heterologous, meaning that they are not naturally operably linked to a plastid PGM gene. Promoters useful for expression in plants are well known in the art and can be inducible, constitutive, tissue specific, derived from eukaryotes, procaryotes or viruses, or have various combinations of these characteristics. Examples of promoters that are suitable for use in plants include the cauliflower mosaic virus 35S promoter, the phytohemagglutinin (PHA) promoter, ribulose-1,5-bisphosphate carboxylase (rbcs) promoters and chlorophyll a/b binding protein (Cab) promoters.

Selection of an appropriate expression vector is relatively simple, as the constraints are minimal. The minimal traits of the vector are that the desired nucleotide sequence be introduced in a relatively intact state. For example, if plant cells are to be transformed with the DNA construct, any vector that will produce a plant carrying the introduced DNA sequence should be sufficient.

Thus, suitable vectors include the Ti plasmid vectors, shuttle vectors designed merely to maximally yield high numbers of copies, episomal vectors containing minimal sequences necessary for ultimate replication once transformation has occurred, transposon vectors, homologous recombination vectors, mini-chromosome vectors, and viral vectors. The selection of vectors and methods to construct them are commonly known to persons of ordinary skill in the art and are described in general technical references, such as Sambrook et al., (1989) *Molecular Cloning, A Laboratory Manual, Second Edition*, Cold Spring Harbor Laboratory Press, Vols. 1–3, which is incorporated herein by reference.

The vector may also include any additional attached nucleotide sequences which will confer resistance to the degradation of the DNA molecule to be introduced, which assists in the process of genomic integration or which provides a means to easily select for transformed cells or plants are advantageous and greatly decrease the difficulty of selecting useable transgenotes. Commonly, expression vectors will contain selection markers, such as kanamycin resistance, hygromycin resistance, to permit detection and/or selection of those cells transformed with the desired DNA sequences (see U.S. Pat. No. 4,704,362, which is herein incorporated by reference).

Useful vectors will generally contain sequences that allow replication in a prokaryotic host useful for cloning the DNA molecule of the present invention. The most commonly used prokaryotic hosts are strains of *Escherichia coli*, although other prokaryotes, such as *Bacillus subtilis* or Pseudomonas may also be used, and are well known in the art. Useful vectors may also contain other sequence elements useful for cloning (for example, restriction sites) or expression (for example, enhancer sequences).

Useful expression vectors are well known in the art and are readily available. Typically, the vector will contain a polyadenylation signal, such as the polyadenylation signal from the cauliflower mosaic 35S gene. The vector may also contain translation regulatory sequences (such as translation start sites), and may also contain introns and splice sites, enhancer sequences (which can be inducible, tissue specific or constitutive), and 5' and 3' regulatory and flanking sequences.

To achieve expression, it is necessary to introduce the appropriate construct into at least some cells of a host organism, such as by transformation. As used herein, the term "transformation" means alteration of the genotype (including episomal genes) of a target organism by the introduction of a nucleic acid sequence. The nucleic acid sequence need not necessarily originate from a different source, but it will, at some point, have been external to the cell into which it is to be introduced.

The host organism can be yeast cells, such as *Saccharomyces cerevisiae*, plant cells such as *Pisum sativum* cells, insect cells such as Tn5 cells and bacterial cells such as *E. coli* and Pseudomanas.

The transformation of plants may be carried out in essentially any of the various ways known to those skilled in the art of plant molecular biology. See, in general, *Methods in Enzymology* Vol. 153 ("Recombinant DNA Part D") 1987, Wu and Grossman Eds., Academic Press, incorporated herein by reference. As used herein, the term "plant" refers to whole plants and plant-derived tissues. As used herein, "plant-derived tissues" refers to differentiated and undifferentiated tissues of plants, including, but not limited to roots, shoots, leaves, pollen, ovules, seeds, tumor tissue, and various forms of cells in culture such as intact cells, protoplasts, embryos and callus tissue. Plant-derived tissues may be in planta or in organ, tissue or cell culture. A "monocotyledonous plant" refers to a plant whose seeds have only one cotyledon, or organ of the embryo that stores and absorbs food. A "dicotyledonous plant" refers to a plant whose seeds have two cotyledons. A "protoplast" refers to a plant cell without a cell wall or extracellular matrix.

The vector may be introduced into plant cells by microinjection, by using polyethylene glycol (Paszkowski et al. (1984) *EMBO J.* 3:2717–2722), by electroporation (Fromm et al. (1985) *Proc. Natl. Acad. Sci. USA* 82:5824–5828), by high ballistic penetration by small particles with the DNA molecule either within the matrix of small beads or particles, or on the surface (Klein et al., (1987) *Nature* 327:70–73).

A preferred method of introducing the vector into plant cells is to infect a plant cell, an explant, a meristem or a seed with a genetically engineered *Agrobacterium tumefaciens* or *Agrobacterium rhizogenes* strain carrying the segment. Within the T-DNA segment of its full-size Ti plasmid or on an abbreviated binary Ti plasmid vector containing the T-DNA boundary sequences of the *Agrobacterium tumafaciens* Ti plasmid is, if used, must be "disarmed", i.e., have its tumor-inducing activity removed, prior to use. To facilitate selection of transgenic plant cells, it is preferable that the gene segment be linked to a selectable marker, for example, kanamycin resistance. In some species, such as *Arabidopsis thaliana*, this Agrobacterium infection process is facilitated by vacuum infiltration of embryonic tissue (as in Becktold et al., (1993) *C.R. Acad. Sci. Paris* 316:1194–1199). Examples of *Agrobacterium tumefaciens* strains that can be used include LBA4404, as described by Hoekema et al., (1983) *Nature* 303:179–180, and EHA101 as described by Hoot et al., (1986) *J. Bacteriol.* 168:1297–1301. A preferred *Agrobacterium rhizogenes* strain is 15834, as described by Birot et al., (1987) *Plant Physiol. Biochem.* 25:323–325. The Ti plasmid is transmitted to plant cells upon infection by *Agrobacterium tumefaciens*, and is stably integrated into the plant genome (Horsch et al., (1984) *Science* 233:496–498; Fraley et al., (1983) *Proc. Natl. Acad. Sci. USA* 80:4803–4807). Under appropriate conditions known in the art, the transformed plant cells are placed under antibiotic selection and grown in tissue culture media to form culture shoots, roots, and eventually intact plants which can be propagated in soil.

Ti plasmids contain two regions essential for the production of transformed cells. One of these, named transfer DNA (T-DNA), induces tumor formation. The other, termed virulent region, is essential for the introduction of the T-DNA into plants. The transfer DNA region, which transfers to the plant genome, can be increased in size by the insertion of the foreign nucleic acid sequence without its transferring ability be affected. By removing the tumor-causing genes so that they no longer interfere, the modified Ti plasmid an then be used as a vector for the transfer of the gene constructs of the invention into an appropriate plant cell, such being a "disabled Ti vector".

There are presently at least three different ways to transform plant cells with Agrobacterium:

(1) co-cultivation of Agrobacterium with cultured isolated protoplasts;

(2) transformation of cells or tissues with Agrobacterium; or (3) transformation of seeds, apices, meristems or whole plants with Agrobacterium.

Method (1) requires an established culture system that allows plant regeneration from cultured protoplasts. Method (2) requires (a) that the plant cells or tissues can be transformed by Agrobacterium and (b) that the transformed cells or tissues can be induced to regenerate into whole plants. Method (3) requires regeneration or micropropagation or simply "propagation" of Arabidopsis seeds transformed with a vector.

In the binary system, to have infection, two plasmids are needed: a T-DNA containing plasmid and a vir plasmid. Any one of a number of T-DNA containing plasmids can be used, the only requirement is that one be able to select independently for each of the two plasmids.

As a result of this plant cell transformation process, a Ti plasmid segment carrying the desired DNA segment is integrated in the nuclear chromosome and transformed cells can be selected by using a selectable marker linked to the desired DNA segment. These selectable markers include, but are not limited to, antibiotic resistance, herbicide resistance or visually-assayable activities. Other selectable markers known in the art may be used in this invention.

Normally, regeneration will be involved in obtaining a complete, transgenic organism from the transformation process. For example, in plants, the term "transgenote" refers to the immediate product of the transformation process and to resultant whole transgenic plants. The term "regeneration" as used herein, means growing a whole or complete transgenic organism. For example, in plants, the term regeneration relates to growing a whole plant form a plant cell, a group of plant cells, a plant part, a plant piece (e.g., from a protoplast, callus, or tissue part), or the propagation of seeds transformed with Agrobacterium by vacuum infiltration.

In plants, regeneration from cultured protoplasts is described in Evans et al., *Protoplast Isolation and Culture in Handbook of Plant Cell Cultures* 1:124–176 (MacMillan Publishing Co. New York 1983); M. R. Kavey, "Recent Developments in the Culture and Regeneration of Plant Protoplasts," Protoplasts (1983)-Lecture Proceedings, pp. 12–29, (Birkhauser, Basal 1983); P. J. Dale, "Protoplasts Culture and Plant Regeneration of Cereals and Other Recalcitrant Crops", Protoplasts (1983)-Lecture Proceedings, pp.31–41 (Birkhauser, Basel (1983); and H. Binding, "Regeneration of Plants," Plant protoplasts pp. 21–73 (CRC Press, Boca Raton 1985).

Identification, selection or confirmation of transgenic organisms is typically based on an assay or assays. Transgenic organisms (such as transgenotes) can be screened by biochemical, molecular biological, and other assays. For example, various assays may be used to determine whether a particular plant, plant part, or transgenote cell shows an increase (i.e., overexpression) or reduction (i.e., suppression) of the plastid PGM gene. Typically the change in expression or activity of the transgenote will be compared to levels found in wildtype (e.g., untransformed) plants of the same type. Preferably, the effect of the introduced construct (transgene) on the level of expression or activity of the endogenous gene will be established from a comparison of sibling plants with and without the construct containing the desired DNA fragment. mRNA levels can be measured by Northern blotting, primer extension, ribonuclease protection, quantitative or semi-quantitative PCR (polymerase chain reaction), and other methods well known in the art (see, e.g., Sambrook et al., (1989)). Protein can be measured in a number of ways including immunological methods such as by ELISA or Western blotting.

The following Examples illustrate the preferred embodiments of the present invention and are not limiting of the specification and claims in any way.

EXAMPLE 1

Characteristics of 8500017

Pea cultivar 8500017 has the following characteristics:
Maturity:
  Number of Nodes at first bloom: 15
  The variety of the present invention blooms 5 days later than Wando. Wando is publically available from the Pisum Plant Introduction Collection, USDA ARF, Johnson Hall, Room 55, Washington State University, Pullman, Wash.
  Number of days to procuring: 77
  Host Units: 1630
Height: The variety of the present invention is about 45 cm high, and is about 5 cm shorter than Wando.
Vine:
  Habit: Indeterminate
  Branching: 1–2 Branches
  Internodes: Zig Zag
  Stockiness: Slim
  Number of Nodes: 19
Leaflets:
  Color: Dark Green
  Wax: Light
  Marbled: Yes
  Number of leaflet pairs: Two
Stipules: The variety of the present invention contains stipules that are marbled. The stipules are the same color as the leaflets, are clasping and are larger in size when compared to the leaflets.
Flower color:
  Venation: Greenish
  Standard: White
  Wing: White
  Keel: White
Pods:
  Shape: Slightly Curved
  Color: Medium Green
  Surface: Rough
  Length: 8 cm
  End: Blunt
  Width (Between Sutures): 11 mm
  Number of Seeds per Pod: 9
Peas: (95–100 Tenderometer)
  Color: Dark Green
  Sieve:
    1—5%
    2—17%
    3—35%
    4—39%
    5—4%
    Average: 3.20%
Seeds: (Dry, Mature):
  Shape: Flattened
  Surface: Wrinkled and Dull
  Color Pattern: Monocolor
  Primary Color: Cream & Green
  Hilum Floor Color: Tan
  Cotyledon Color: Green
  Number of grams per 100 Seeds: 14
Disease Resistance: The *Pisum sativum* variety of the present invention is resistant to Fusarium Wilt Fungus and Powdery Mildew Fungus The closest *Pisum sativum* varieties to the *Pisum sativum* variety of the present invention are: Lazor, Markado and Trek. Lazor has been described earlier. Markado is a full season, medium sieve, freezer with dark green (freezer) peas and with relatively fine foliage compared to other larger sieve freezer varieties. Markado is commercially available from Novartis (Boise, Id.). Trek is a mid-season, medium-sieve freezer variety with afila foliage and medium dark green berry color. Trek is commercially available under the Asgrow Brand from Seminis Vegetable Seeds.

EXAMPLE 2

Starch and Sucrose in the Leaves of the Peas Present Invention and Examination of Enzyme Activity Compared with Peas of a Wrinkled *Pisum sativum* Variety that Contains the r Gene The pea variety Lazor, which contains homozygous r gene and produces wrinkled mature seed, and a bsg-introgressed line of Lazor which produces highly wrinkled seed were studied in this example. A sample of leaves from Lazor and bsg-introgressed line of Lazor were dried to a stable weight in a lyophilizer and then pulverized to a powder using a mortar and pestle. Pre-weighed amount of the samples (~100 mg) was washed several times in 80% ethanol at 70° C. The ethanol supernatants were pooled and used for sucrose determination. The pellet was used for starch determination.
Quantification of Starch Sugar was removed from lyophilized tissue samples by several washes at 70° C. in 80% ethanol. Starch was gelatinized by autoclaving for 45 minutes and then hydrolyzed by digestion at 37° C. with α-amylase (Sigma) in 0.3 M sodium acetate, pH 5.2 followed by further digestion with *Aspergillus niger* amyloglucosidase (Sigma) in 0.1 M sodium acetate, pH 4.6 at 55° C. Samples were deproteinized by boiling and glucose was assayed enzymatically by coupling the oxidation of glucose to the reduction of NAD+ with hexokinase (Boehringer/Mannheim) and glucose-6-P dehydrogenase (Sigma).

An aliquot of the hydrolyzed starch was incubated at room temperature in 0.1 M Tris-Cl (pH 8), 1 mM ATP, 1 mM NAD+, 2 mM $MgCl_2$, 15 U/ml yeast hexokinase, and 15 U/ml *Leuconostoc mesenteroides* glucose-6-phosphate dehydrogenase. The reaction was allowed to go to completion and the absorbance was read at 340 nm and compared with a standard curve. The results are shown below in Table 1.

Quantification of Sucrose

The pooled 80% ethanol supernatants were brought to 6.5 mls with 80% ethanol. Following the addition of 3.6 ml of water and 2.15 ml of chloroform, the sample was vortexed and spun in a table top centrifuge. After the bottom phase had been back-extracted with 0.2 ml of water, the top phases were pooled, evaporated to dryness on a Savant Speed-Vac Concentrator, and resuspended in 0.2 ml of water.

Glucose and fructose were destroyed by treating the sample for 30 minutes at 90° C. in the presence of 3.7 volumes of 0.1 M NaOH. The sample was then neutralized by the addition of 0.5 volumes of 1 M sodium acetate, pH 4.6. Sucrose levels were determined using a dehydrogenase-coupled spectrophotometric assay. An aliquot of the alkali-treated sample was incubated at room temperature in 40 mM imidazole (pH 6.9), 1 mM ATP, 1 mM NAD+, 5 mM $MgCl_2$, 0.5 mM DTT, 0.02% BSA, 32 U/ml invertase, 5 U/ml yeast hexokinase, and 5 U/ml *Leuconostoc mesenteroides* glucose-6-phosphate dehydrogenase. The reaction was allowed to go to completion and the absorbance was read at 340 nm and compared with a standard curve. The results are shown below in Table 1.

TABLE 1

Starch and Sucrose Levels in Leaves from Lazor and bsg -introgressed lines of *Pisum sativum*

|      | Starch % dry wt   | Starch % fresh wt   | Sucrose % dry wt | Sucrose % fresh wt |
|------|-------------------|---------------------|------------------|--------------------|
| Lazor | 3.060 +/− 0.071 | 0.4948 +/− 0.0220   | 8.18 +/− 0.69    | 1.32 +/− 0.14      |
| bsg  | 0.015 +/− 0.002   | 0.0023 +/− 0.0004   | 10.19 +/− 0.78   | 1.58 +/− 0.12      |

Table 1 shows that leaf starch levels in the *Pisum sativum* line having the bsg gene introgressed into Lazor are at most only about 0.5% of Lazor. Also, Table 1 demonstrates that sucrose levels were increased in the leaves of the *Pisum sativum* line containing the bsg gene.

ADP-glucose Pyrophosphorylase Assays

Embryos from Lazor and a bsg gene introgressed line of Lazor frozen in liquid nitrogen were ground in a mortar in the presence of 3–4 volumes of ice-cold extraction buffer (100 mM 2-(N-morpholino) ethane sulfonic acid (MOPS) (pH 7.2), 5 mM $MgCl_2$, 1 mM EDTA, 5 mM DTT). Starch and cell debris were removed by pelleting for 10 minutes at 27,000×g. Aliquots of the supernatant were then quick-frozen in liquid nitrogen and stored at −80° C. ADPG-PPase activity was found to be stable under these storage conditions.

ADP-glucose pyrophosphorylase was assayed in the reverse direction at 25° C. by coupling production of glucose-1-P to reduction of NAD+. Standard reaction mixtures (1 ml) contained 75 mM 4-(2-hydroxyethyl)-1-piperazine-ethane sulfonic acid (HEPES) (pH 7.75), 5 mM $MgCl_2$, 1 mM 3PGA, 0.1 mg/ml bovine serum albumin, 5 µM glucose-1,6-bisphosphate; 1.5 mM ADP-glucose, 0.4 mM NAD+; 2 U each of phosphoglucomutase (Sigma) and *Leuconostoc mesenteroides* glucose 6-phosphate dehydrogenase (Sigma), and up to 100 µl of extract. After a one minute pre-incubation period reactions were initiated by addition of sodium pyrophosphate to 1.5 mM. NADH production was monitored spectrophotometrically at 340 nm against a reaction mixture which lacked sodium pyrophosphate. The rate was proportional to the amount of extract added and the reaction was linear over at least 3 minute time periods. One unit is defined as the amount of enzyme that produces 1 µ mole of glucose-1-P per minute.

Protein concentrations were determined using the dye reagent from BioRad. The results are shown below in Table 2.

TABLE 2

ADP-glucose pyrophosphorylase Activity in Embryos from Lazor and bsg-introgressed lines of *Pisum sativum*

|       | Embryo wt, g | ADPG-PPase activity, U/mg protein |
|-------|--------------|------------------------------------|
| Lazor | .28          | .0559                              |
|       | .31          | .0373                              |
| bsg   | .28          | .0388                              |
|       | .31          | .0271                              |

Table 2 shows that the activity of ADP glucose pyrophosphorylase is not greatly reduced in the cotyledons of the present invention when compared to the activity in the variety Lazor.

Analysis of Phosphoglucomutase Isozymes by Starch Gel Electrophoresis

Embryos (0.25–0.3 g) or leaves (0.5 g) frozen in liquid nitrogen were ground in an ice-cold mortar in the presence of extraction buffer (0.1 M Tris-Cl, pH 7.8; 2% reduced glutatione) plus 50 mg of polyvinylpolypyrrolidone and a small amount of acid-washed sand. Extracts were squeezed through one layer of miracloth and, in some experiments, diluted with extraction buffer to equal chlorophyll concentrations (as determined by the formula: $[(A_{645} \times 202) + (A_{663} \times 80.2)] \times 10.5 = \mu g$ chlorophyll/ml). Extracts were taken up by 5 mm×1 cm 3 MM wicks and placed 4 cm from the cathodal end in a 12% starch gel prepared in 15 mM Tris/4 mM citric acid, pH 7.8. A 3 MM wick was used to connect the starch gel to the electrode buffer (0.3 M sodium borate, pH 7.8). Electrophoresis was done in the cold room for 20 minutes at 200 V/30 mA. The wicks were then removed and electrophoresis was continued at 30 mA until the voltage reached 300 V; the voltage was then maintained at 300 V until the dye front had moved ~11 cm.

The upper portion of the starch gel was then sliced off and the bottom 1 mm section was stained for phosphoglucomutase (PGM) activity using a 0.7% agarose overlay containing 0.1 M Tris-Cl (pH 7.5), 10 mM $MgCl_2$, 1.5 mg/ml glucose-1-P, 0.15 mg/ml NADP+, 0.2 mg/ml MTT, 40 µg/ml PMS, and 0.4 U/ml glucose-6 phosphate dehydrogenase. After a 15 minute incubation in the dark at 30° C., the gel was washed for 1 minute in 1% acetic acid, rinsed several times with water, and fixed in 5:2:1:4 ethanol:acetic:acid:glycerine water.

Chloroplasts were isolated according to the method described in *Methods in Plant Molecular Biology*, 141–172, Cold Spring Harbor Press, Lamppa, J. K., et al., eds. 1995, "Section 8 In vitro Import of Proteins into Chloroplasts," 1995, herein incorporated by reference. Leaves (~20 g) were gently homogenized in 450 ml of ice-cold grinding buffer (2 mM EDTA, 1 mM $MgCl_2$, 1 mM $MnCl_2$, 50 mM HEPES-KOH (pH 7.5), 0.33 M sorbitol) with a Polytron set at 3.5 for 2 one minute bursts. The homogenate was filtered through four layers of cheesecloth and four layers of Miracloth and then pelleted in a GSA rotor at 4000 rpm for 1 minute at 4° C. The pellets were resuspended in 8 ml of grinding buffer and layered over two 40%/80% Percoll step gradients made up in grinding buffer plus 0.86 mg/ml ascorbic acid and 0.35 mg/ml reduced glutathione. The gradients were spun in an HB-4 rotor at 7500 rpm for 8 minutes at 4° C. The lower chloroplast band was resuspended in 30 ml grinding buffer and repelleted by centrifugation in an HB-4 rotor at 3500 rpm for 5 minutes. The pellets were resuspended in 30 ml of 1×HSM (10 mM HEPES-KOH, pH 8, 0.33 M sorbitol, 8.4 mM methionine) and repelleted in an HB-4 rotor at 3500 rpm for 5 minutes at 4° C. The pellets were then either lysed by being taken up in hypotonic medium (10 mM Tris-Cl, pH 7.8, 2% reduced glutathione) or resuspended in 1×HSM and lysed by freeze-thawing.

Figure 4:
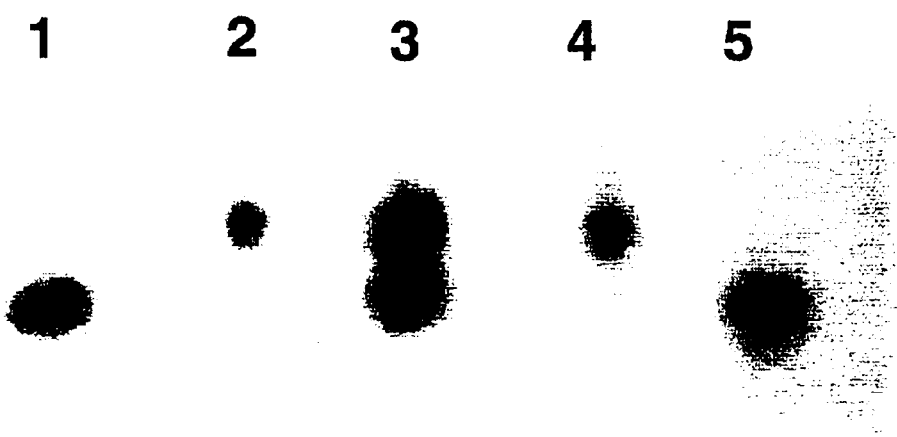
FIG. 4 shows the electrophoretic separation of phosphoglucomutase activities from a pea variety containing the r gene homozygous within its genome and from a *Pisum sativum* variety containing the bsg gene homozygous within its genome. Lane 1 shows leaf extract from a variety containing the bsg gene. Lane 2 shows chloroplasts isolated from a variety containing the r gene. Lane 3 shows leaf extract from a variety containing the r gene. Lane 4 shows chloroplasts isolated from a variety containing the r gene. Lane 5 shows leaf extract from a variety containing the bsg gene.
Figure 5:
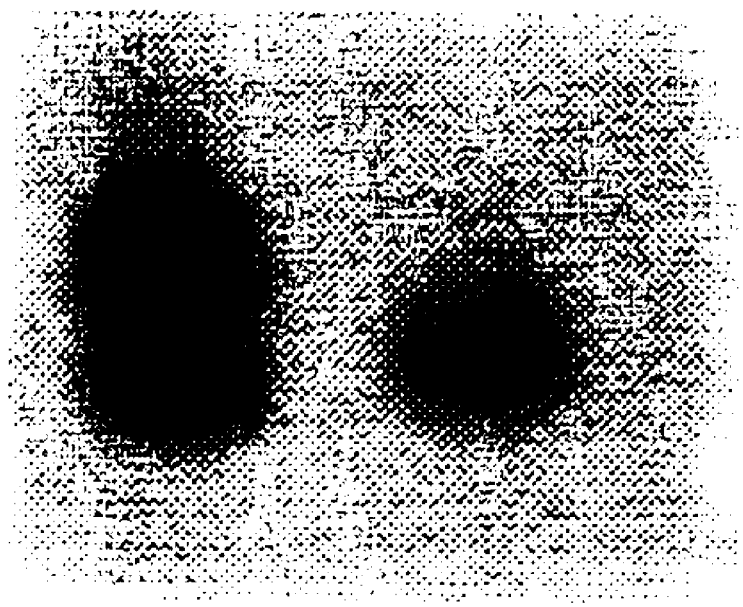
FIG. 5 shows an electrophoretic separation of phosphoglucomutase activities from peas containing the r gene and from peas containing the bsg gene. Lane 1 shows a cotyledon extract from a variety containing the r gene. Lane 2 shows a cotyledon extract from a variety containing the bsg gene.

FIG. 4 shows the electrophorectic separation of phosphoglucomutase activities in Lazor and in the *Pisum sativum* line having the bsg gene introgressed into Lazor. In Lazor, two isozymes are resolved in extracts from its leaves, whereas only one isozyme stains for phosphoglucomutase isozymes in the bsg gene introgressed *Pisum sativum* line of Lazor. In extracts from leaves from the bsg introgressed line of Lazor, the isozyme missing from the bsg-introgressed *Pisum sativum* line of Lazor, which is the less electronegative isozyme, is the isozyme found in isolated chloroplasts. The same isozyme band is also missing in embryo extracts from the bsg-introgressed *Pisum sativum* line of Lazor which is shown in FIG. 5.

EXAMPLE 3

Sugar Analysis of Frozen Peas

Peas of a bsg introgressed line, derived from crosses with Encore and referred to as Encore BSG, and peas of the *Pisum sativum* variety XPF330 were frozen for high performance liquid chromatography (HPLC). XPF330 is a proprietary variety of Seminis Vegetable Seeds, Inc. XPF330 is late season, produces wrinkled mature seed that contains the r gene and is resistant to Powdery Mildew Fungus. The frozen pea samples were stored at −20 degrees centigrade until extracted. The peas were subsampled and weighed out on a Mettler AT200 analytical balance. Absolute ethanol was added to the subsample (4:1 ratio, volume/weight). The sample was cooled and stored overnight (at −20° C.) then ground with an IKA Ultra Turrax T25 homogenizer. The homogenate was returned to the freezer. The following day, the sample was mixed, then centrifuged to clarify the extract. An aliquot was removed and sealed in an autosampler vial and stored at −20° C. until analyzed.

The sugars are separated on a Hewlett-Packard 1050 HPLC chemstation system, employing a refractive index detector. The column used was a Whatman Partsil 5PAC column (4×12.5 mm). The solvent system was composed of 85% acetonitrile at a flow rate of 0.85 ml/minute at 35° C. The injection volume was 5 microliters. A standard mixture of glucose, fructose and sucrose in 80% ethanol was used to quantitate the sugars. This standard was injected after every tenth sample. The results are shown below in Table 3.

TABLE 3

| LINE | | Fru | Glc | Suc |
|---|---|---|---|---|
| Encore BSG | Avg. | 0.058 | 0.031 | 6.773 |
| | Stds | 0.008 | 0.011 | 0.271 |
| | CV | 14.451 | 33.973 | 4.001 |
| | StdErr | 0.003 | 0.004 | 0.111 |
| | Count | 6 | | |
| XPF 330 | Avg. | 0.037 | 0.019 | 4.552 |
| | Stds | 0.003 | 0.004 | 0.125 |
| | CV | 7.884 | 22.959 | 2.757 |
| | StdErr | 0.001 | 0.002 | 0.051 |
| | Count | 6 | | |

The results shown above in Table 3 demonstrate that peas containing the bsg gene homozygous within their genome contain higher levels of fructose, glucose and sucrose than peas containing the r gene homozygous within its genes.

EXAMPLE 4

Sucrose Analysis of Frozen Peas

Frozen samples from the *Pisum sativum* varieties or lines listed below in Tables 4 and 5 were stored at −20° C. until extracted. The peas were subsampled and weighed out on a Mettler AT200 analytical balance. Absolute ethanol was added to the subsample (4:1 ratio, volume/weight). The sample was cooled and stored overnight (at −20° C.) then ground with an IKA Ultra Turrax T25 homogenizer. The homogenate was returned to the freezer. The following day, the sample was mixed, then centrifuged to clarify the extract. An aliquot was removed and sealed in an autosampler vial and sealed in an autosampler vial and stored at −20° C. until analyzed.

The sugars are separated on a Hewlett-Packard 1050 HPLC chemstation system, employing a refractive index detector. The column used was a Whatman Partsil 5PAC column (4×12.5 mm). The solvent system was composed of 85% acetonitrile at a flow rate of 0.85 ml/minute at 35° C. The injection volume was 5 microliters. A standard mixture of sucrose in 80% ethanol was used to quantitate sucrose. This standard was injected every tenth sample. The results are shown below in Tables 4 and 5.

TABLE 4

(fresh weight)

| Variety | Tenderometer | % Sucrose Average | bsg gene |
|---|---|---|---|
| Bolero | 99 | 4.75 | No |
| Bolero | 99 | 4.64 | No |
| Dual | 97 | 4.56 | No |
| Dual | 97 | 4.27 | No |
| EX 8500567 | 95 | 6.26 | Yes |
| EX 8500567 | 95 | 6.22 | Yes |
| EX 8500567 | 102 | 6.39 | Yes |
| EX 8500567 | 102 | 6.40 | Yes |
| Lazor | 93 | 4.78 | No |
| Lazor | 93 | 5.06 | No |
| Lazor | 99 | 4.82 | No |
| Lazor | 99 | 4.89 | No |
| Lazor BSG | 95 | 6.37 | Yes |
| Lazor BSG | 95 | 6.50 | Yes |
| Lazor BSG | 97 | 6.45 | Yes |
| Lazor BSG | 97 | 6.56 | Yes |
| Quantum | 98 | 4.82 | No |
| Quantum | 98 | 4.83 | No |
| Spring | 98 | 4.86 | No |
| Spring | 104 | 4.77 | No |
| Tacoma | 94 | 4.78 | No |
| Tacoma | 94 | 4.72 | No |
| Tacoma | 99 | 4.47 | No |
| Tacoma | 99 | 4.39 | No |
| XP F357 | 96 | 5.15 | No |
| XP F357 | 96 | 5.57 | No |
| XP F357 | 104 | 5.36 | No |
| XP F357 | 104 | 5.31 | No |

TABLE 5

Sucrose Analysis of Frozen Peas (fresh weight)

| Variety | % Sucrose Average | Tenderometer | bsg gene |
|---|---|---|---|
| B1R X MCRO | 4.90 | 97 | No |
| BEMAf x Alf | 4.81 | 100 | No |
| Bolero | 5.25 | 96 | No |
| Bolero x Bemol Af | 4.75 | 98 | No |
| CM279 | 5.52 | 102 | No |
| CM279 | 5.45 | 98 | No |

TABLE 5-continued

Sucrose Analysis of Frozen Peas (fresh weight)

| Variety | % Sucrose Average | Tenderometer | bsg gene |
|---|---|---|---|
| CM279 | 5.57 | 98 | No |
| CM279 | 5.02 | 100 | No |
| Dinos | 4.74 | 97 | No |
| 8500567 | 6.59 | 96 | Yes |
| 8500567 | 7.06 | 97 | Yes |
| 8500567 | 6.70 | 90 | Yes |
| 8500567 | 5.75 | 87 | Yes |
| EF680 X Tacoma | 4.83 | 104 | No |
| Encore X Tacoma | 4.79 | 98 | No |
| F226 X Darfon | 4.61 | 103 | No |
| F234 X Mrkd | 5.73 | 103 | No |
| F240 X Tacoma | 5.16 | 97 | No |
| F240 X Tacoma | 4.90 | 98 | No |
| F353 | 5.50 | 99 | No |
| F357 | 5.11 | 97 | No |
| F383 | 5.38 | 97 | No |
| Kalamo | 5.09 | 97 | No |
| Lazor | 5.61 | 100 | No |
| Lazor | 5.31 | 97 | No |
| Lazor | 5.25 | 97 | No |
| Lazor BSG | 7.10 | 92 | Yes |
| Lazor BSG | 7.07 | 95 | Yes |
| Lazor BSG | 6.74 | 93 | Yes |
| Lea X F240 | 5.86 | 97 | No |
| Lea X Tacoma | 5.18 | 103 | No |
| M153 | 4.84 | 97 | No |
| Micro PMB C1 | 4.88 | 97 | No |
| Novll X F240 | 5.06 | 101 | No |
| P1Sdin X Nvll | 5.42 | 100 | No |
| P1sDn X Nvll | 6.08 | 97 | No |
| Sknd X R86275 X | 5.13 | 102 | No |
| Sknd X R86275 X | 5.51 | 98 | No |
| Snake | 5.09 | 98 | No |
| Spr DMBC X | 5.85 | 98 | No |
| Spring | 5.34 | 95 | No |
| Spring | 5.20 | 99 | No |
| Spring | 4.78 | 96 | No |

The *Pisum sativum* varieties, Bolero, Dual, Lazor, Quantum, Spring and Tacoma listed in Table 4, produce wrinkled mature seeds and contain r gene homozygous within their genome. These varieties are commercially available from Seminis Vegetable Seeds, Inc. The *Pisum sativum* varieties 8500567 and 8500557, also shown in Table 4, produce highly wrinkled seeds and contain the bsg gene homozygous within their genome. 8500567 and 8500557 are proprietary varieties of Seminis Vegetable Seeds, Inc. The *Pisum sativum* line, Lazor BSG also shown in Table 4, produces highly wrinkled seeds and contains the bsg gene homozygous within its genome. Lazor BSG is a proprietary variety of Seminis Vegetable Seeds, Inc. XPF357, also shown in Table 4, produces wrinkled seeds and contains the r gene within its genome. XPF357 is a proprietary variety of Seminis Vegetable Seeds, Inc.

The *Pisum sativum* varieties and breeding lines shown in Table 5, with the exception of 8000567 and Lazor BSG, produce wrinkled seeds and contain the r gene homozygous within their genome. All of these varieties (with the exception of Snake) are proprietary varieties (or breeding lines) of Seminis Vegetable Seeds, Inc. The *Pisum sativum* varieties Bolero, Lazor, Dinos, Kalamo and Spring, produce wrinkled seeds and contain the r gene homozygous within their genome. These varieties are commercially available from Seminis Vegetable Seeds, Inc.

Snake, also shown in Table 6, produces wrinkled seeds and contains the r gene homozygous within its genome. Snake is commercially available from Cristes Moscow Growers, Moscow, Id.

The average sucrose produced by peas containing the bsg gene homozygous in its genome in Tables 4 and 5 was 6.54 (with values ranging from 5.75 to 7.10 when measured at tenderometer values from about 87 to about 102). The average amount of sucrose produced by peas that did not contain the bsg gene in the sucrose tests conducted in 1996–1997 was 5.08 (with values ranging from 4.27 to 6.08).

EXAMPLE 5

Alcohol Insoluble Solids Analysis in Various Peas

This Example describes the alcohol insoluble solids content on canned peas from several different *Pisum sativum* varieties or lines. The protocol for determining the alcohol insoluble solids on these canned peas is as follows:

a) open can, pour the contents over an 8 mesh sieve, rinse with two volumes of tap water, and allowed to drain for two (2) minutes;

b) weigh 90–100 grams of peas to the nearest 0.1 gram, transfer to a blender cup, add to the cup an equal volume of deionized water;

c) blend the peas for two (2) minutes on the blend setting;

d) weigh 40 grams of the blended mix to the nearest 0.01 grams and transfer quantitatively to a 1 liter boiling flask fitted with a reflux condenser. 280 ml of 86% ethanol is used to complete the transfer;

e) boil the mixture for 30 minutes;

f) place a 11 cm Whatman #1 filter paper, previously dried in a metal weighing dish and weighed to the nearest 0.01 grams, into an 8 cm Buchner filter apparatus, in a manner so that the edges of the paper extend 1 cm up the sides of the filter apparatus. Apply suction to the apparatus and filter the alcohol-solids mixture quantitatively through the paper; wash the residue from the flask with 80% ethanol until the washings are colorless. Do not overfill the cup formed by the filter paper; and g) return the filter paper to a drying oven in its original metal weighing dish and dry at 100° C. for 2 hours. Cool in a desiccator and weigh to the nearest 0.01 grams. Determine the weight of dry, alcohol insoluble solids by difference and multiply by 5 to convert to percentage alcohol insoluble solids.

The alcohol insoluble solids value at 105 tenderometer was calculated using linear regression from paired measures of alcohol insoluble solids and tenderometer for each variety. The tenderometer value at 12% alcohol insoluble solids was calculated by linear regression from the same paired data. For the pea varieties of the present invention that contain the bsg gene, it was necessary to extend the regression line beyond the range of data in order to intercept 12 percent. For example, 8500557, a pea variety containing the bsg gene, had 7.2% AIS at a tenderometer of 105, and the calculated tenderometer for 12% AIS is 199. Table 6, below shows the alcohol insoluble solids value at 105 and tenderometer value 12% AIS for several varieties of *Pisum sativum*.

TABLE 6

| Code | Tdr= | 105 | AIS= | 12.0 | bsg gene |
|---|---|---|---|---|---|
| 8500557 | AIS= | 7.2 | Tdr= | 199 | Yes |
| 8500567 | AIS= | 7.7 | Tdr= | 200 | Yes |
| Tender | AIS= | 8.9 | Tdr= | 124 | No |

TABLE 6-continued

| Code | Tdr= | 105 | AIS= | 12.0 | bsg gene |
|---|---|---|---|---|---|
| Revolution | AIS= | 9.3 | Tdr= | 135 | No |
| 10 002 | AIS= | 9.8 | Tdr= | 127 | No |
| 20 028 | AIS= | 10.1 | Tdr= | 128 | No |
| Zamira | AIS= | 10.2 | Tdr= | 123 | No |
| Pacha | AIS= | 10.3 | Tdr= | 126 | No |
| Cabro | AIS= | 10.3 | Tdr= | 124 | No |
| 20 037 | AIS= | 10.3 | Tdr= | 124 | No |
| CMG290 | AIS= | 10.4 | Tdr= | 123 | No |
| Magic | AIS= | 10.4 | Tdr= | 119 | No |
| Avola | AIS= | 10.4 | Tdr= | 125 | No |
| 20 036 | AIS= | 10.5 | Tdr= | 124 | No |
| Fresca | AIS= | 10.5 | Tdr= | 121 | No |
| 10 003 | AIS= | 10.5 | Tdr= | 122 | No |
| Bolero | AIS= | 10.5 | Tdr= | 120 | No |
| Samish | AIS= | 10.6 | Tdr= | 121 | No |
| Quad | AIS= | 10.6 | Tdr= | 119 | No |
| Titan | AIS= | 10.6 | Tdr= | 121 | No |
| 20 029 | AIS= | 10.7 | Tdr= | 114 | No |
| Renard | AIS= | 11.0 | Tdr= | 116 | No |
| 20 047 | AIS= | 11.1 | Tdr= | 115 | No |
| 20 019 | AIS= | 11.3 | Tdr= | 119 | No |
| Methow | AIS= | 11.5 | Tdr= | 110 | No |
| 20 035 | AIS= | 11.8 | Tdr= | 107 | No |
| Catalina | AIS= | 12.0 | Tdr= | 105 | No |
| Fristo | AIS= | 12.0 | Tdr= | 105 | No |
| Orlando | AIS= | 13.2 | Tdr= | 95 | No |
| Kong | AIS= | NS | Tdr= | NS | No |
| Lazor BSGBC1 | AIS= | 8.0 | Tdr= | 194 | Yes |
| Lazor BSGBC2 | AIS= | 8.4 | Tdr= | 180 | Yes |
| 20 078 | AIS= | 8.7 | Tdr= | 131 | No |
| Paso | AIS= | 9.0 | Tdr= | 133 | No |
| Mathilde | AIS= | 9.1 | Tdr= | 131 | No |
| 20 071 | AIS= | 9.3 | Tdr= | 125 | No |
| 20 089 | AIS= | 9.5 | Tdr= | 128 | No |
| Globo | AIS= | 9.5 | Tdr= | 124 | No |
| 20 091 | AIS= | 9.6 | Tdr= | 121 | No |
| Waverex | AIS= | 9.6 | Tdr= | 131 | No |
| 20 067 | AIS= | 9.7 | Tdr= | 129 | No |
| 20 100 | AIS= | 9.8 | Tdr= | 122 | No |
| 20 101 | AIS= | 9.9 | Tdr= | 123 | No |
| 20 092 | AIS= | 10.0 | Tdr= | 127 | No |
| 10 021 | AIS= | 10.0 | Tdr= | 121 | No |
| 10 025 | AIS= | 10.1 | Tdr= | 126 | No |
| 20 090 | AIS= | 10.2 | Tdr= | 125 | No |
| Nitro | AIS= | 10.2 | Tdr= | 123 | No |
| 10 016 | AIS= | 10.2 | Tdr= | 123 | No |
| 20 075 | AIS= | 10.3 | Tdr= | 124 | No |
| 10 015 | AIS= | 10.3 | Tdr= | 125 | No |
| Darfon | AIS= | 10.3 | Tdr= | 120 | No |
| Kimo | AIS= | 10.4 | Tdr= | 123 | No |
| 20 093 | AIS= | 10.4 | Tdr= | 121 | No |
| R555 | AIS= | 10.4 | Tdr= | 127 | No |
| 20 068 | AIS= | 10.4 | Tdr= | 121 | No |
| 20 030 | AIS= | 10.4 | Tdr= | 122 | No |
| Barle | AIS= | 10.5 | Tdr= | 119 | No |
| 20 069 | AIS= | 10.5 | Tdr= | 117 | No |
| 10 020 | AIS= | 10.5 | Tdr= | 121 | No |
| Brule | AIS= | 10.6 | Tdr= | 118 | No |
| 20 073 | AIS= | 10.7 | Tdr= | 119 | No |
| Curico | AIS= | 10.7 | Tdr= | 115 | No |
| Purser | AIS= | 10.7 | Tdr= | 115 | No |
| 20 094 | AIS= | 10.7 | Tdr= | 120 | No |
| 20 116 | AIS= | 10.7 | Tdr= | 117 | No |
| 20 076 | AIS= | 10.8 | Tdr= | 119 | No |
| Lynx | AIS= | 10.9 | Tdr= | 115 | No |
| 20 102 | AIS= | 10.9 | Tdr= | 118 | No |
| 20 103 | AIS= | 10.9 | Tdr= | 118 | No |
| Sigra | AIS= | 10.9 | Tdr= | 116 | No |
| Encore | AIS= | 11.0 | Tdr= | 115 | No |
| Alamado | AIS= | 12.0 | Tdr= | 115 | No |
| Markado | AIS= | 11.0 | Tdr= | 116 | No |
| 20 070 | AIS= | 11.1 | Tdr= | 115 | No |
| Bolero | AIS= | 11.1 | Tdr= | 114 | No |
| Spring | AIS= | 11.1 | Tdr= | 114 | No |
| Tyne | AIS= | 11.1 | Tdr= | 116 | No |
| Deltafon | AIS= | 11.2 | Tdr= | 111 | No |
| 10 017 | AIS= | 11.2 | Tdr= | 113 | No |
| Wolf | AIS= | 11.2 | Tdr= | 113 | No |
| 20 119 | AIS= | 11.3 | Tdr= | 111 | No |
| Lazor | AIS= | 11.4 | Tdr= | 110 | No |
| 20 063 | AIS= | 11.4 | Tdr= | 110 | No |
| 20 074 | AIS= | 11.4 | Tdr= | 113 | No |
| 20 087 | AIS= | 11.4 | Tdr= | 113 | No |
| Camina | AIS= | 11.4 | Tdr= | 112 | No |
| 20 120 | AIS= | 11.4 | Tdr= | 112 | No |
| Masterfon | AIS= | 11.5 | Tdr= | 111 | No |
| 20 118 | AIS= | 11.5 | Tdr= | 110 | No |
| Vevas | AIS= | 11.5 | Tdr= | 110 | No |
| 20 106 | AIS= | 11.6 | Tdr= | 107 | No |
| Snake | AIS= | 11.6 | Tdr= | 109 | No |
| 20 088 | AIS= | 11.7 | Tdr= | 108 | No |
| 20 117 | AIS= | 11.8 | Tdr= | 107 | No |
| 20 072 | AIS= | 11.9 | Tdr= | 106 | No |
| Prism | AIS= | 12.0 | Tdr= | 105 | No |
| Dual | AIS= | 13.0 | Tdr= | 95 | No |

The *Pisum sativum* varieties Tender, Revolution, Avola, Orlando, Markado, Barle, Sigra, Encore, Methow, Alamado, Tyne, Deltafon, Lazor, Camina, Wolf, Masterfon, Veras, Pacha, Bolero, Cabro, Fristo, Paso, Mathilde, Globe, Nitro, Darfon, Kimo, Dual, Prism, Magic, Titan, Renard, Catalina, Kong, Curico and Lynx listed in Table 6, produce wrinkled mature seeds and contain the r gene homozygous within their genome. These varieties are commercially available from Seminis Vegetable Seeds, Inc. The *Pisum sativum* varieties CMG290, Samish, Quad, Snake and Brule produce wrinkled seed and contain the r gene homozygous within their genome. These *Pisum sativum* varieties are commercially available from Crites Moscow Growers, Moscow, Id.

The *Pisum sativum* variety Zamira produces wrinkled mature seeds and contains the r gene homozygous within its genome. Zamira is commercially available from Nunhems Zaden (Haelen, Netherlands).

The *Pisum sativum* variety Fresca produces wrinkled mature seeds and contains the r gene homozygous within its genome. Fresca is commercially available from Vilmoran (Empire, Calif.).

The *Pisum sativum* variety Waverex produces wrinkled mature seeds and contains the r gene homozygous within its genome. Waverex is commercially available from Van Waveren (Gottingen, West Germany).

The *Pisum sativum* variety Purser produces wrinkled mature seeds and contains the r gene homozygous within its genome. Purser is commercially available from Novartis (Boise, Id.).

The *Pisum sativum* varieties 8500557 and 8500567 produce highly wrinkled mature seeds and contain the bsg gene homozygous within their genome. 8500557 and 8500567 are proprietary varieties of Seminis Vegetable Seeds.

All other *Pisum sativum* varieties or lines used in Table 6 produce wrinkled mature seeds and contains the r gene homozygous within their genome. All are proprietary varieties of Seminis Vegetable Seeds, Inc.

EXAMPLE 6

Analysis of Sucrose and AIS Levels 22 frozen samples of peas were tested for the percentage (%) sucrose and alcohol insoluble solids. Peas were tested from the *Pisum sativum* varieties or lines Quantum, Lazor and LazorBSGBC2. Lazor BSGBC2 was selected after 2 backcrosses of the bsg from M82.1 into Lazor (as a recurrent parent). The same procedures used in Examples 3 and 4 to determine and AIS were used in this Example. The results are shown in Table 7.

TABLE 7

| Variety | Tenderometer | % Sucrose | % AIS |
|---|---|---|---|
| Quantum | 92 | 6.01 | 8.8 |
| Quantum | 100 | 6.26 | 9.6 |
| Lazor | 95 | 5.88 | 9.5 |
| Lazor | 101 | NA | 10.7 |
| Lazor BSGBC2 | 91 | 7.01 | 7.3 |
| Lazor BSGBC2 | 99 | 7.07 | NA |

These results show that peas of the *Pisum sativum* line Lazor BSGBC2 contained a higher percentage fresh weight of sucrose and lower % of AIS than the Quantum and Lazor varieties.

EXAMPLE 7

Molecular Characterization of the bsg Gene

A. Materials and Methods

1. Preparation of Poly(A)+RNA

RNA was prepared from leaves and cotyledons as described in Dunsmuir et al. (1987) In: Gelvin, S. and Schilperoot, R., eds. Plant Molecular Biology Manual, Vol 9. Plenum, N.Y., pp. 45–59, herein incorporated by reference. Poly(A)+RNA was isolated using a Poly A Tract Kit (Promega).

2. PGM Transcript Analysis

Total and poly (A)+cotyledon RNA were separated electrophoretically on a 1.1% agarose gel containing 6% formaldehyde and prepared in a buffer consisting of 20 mM MOPS (3-[N-morpholino]propane-sulfonic acid), 5 mM sodium acetate, 1 mM EDTA, pH 8. This buffer was also used as the reservoir buffer except the pH was adjusted to 7. RNA was denatured at 55° C. in 65% formamide, 8% formaldehyde, 26 mM MOPS, 6.5 mM sodium acetate, 1.3 mM EDTA, pH 8 before being loaded on to the formaldehyde gel. Following electrophoresis at 4 V/cm, the RNA was transferred to a Duralon-UV membrane (Stratagene) and UV-cross-linked with a Stratagene Stratalinker.

For detection of plastid PGM transcripts, Northern blots were hybridized with a 1.1 kb HindIII fragment from the 3' half of the wild-type cDNA clone, which was labeled with Klenow using random primers (Feinberg, A. P. et al., *Anal. Biochem.* 132:6–13). Hybridizations were performed in 0.25 M phosphate buffer (pH 7.4), 7% SDS, 1 mM EDTA, 1% bovine serum albumin at 65° C. in a Robbins Hybridization incubator. Final washes were performed in 0.1×SSC at 65° C.

3. Preparation of First Strand cDNA

First strand cDNA was prepared using Superscript reverse transcriptase II (GibcoBRL). First strand synthesis was primed off of the $dT_{17}$ adapter primer (GGAGATCTGG TAAGCTTGTT TTTTTTTTTT $TTTTT_{17}$) (SEQ ID NO:21) according to the instructions of the manufacturer and using 200 ng of poly (A)+RNA. The final product was diluted to 0.5 ml with water.

4. Preparation of Genomic DNA

To prepare genomic DNA 2.5 g of leaves frozen in liquid nitrogen were ground in a mortar in the presence of 4 mls of urea buffer (7 M urea, 0.31 M NaCl, 50 mM Tris-Cl (pH 8), 20 mM EDTA, 1% N-lauroyl sarcosine). Following phenol-chloroform extraction, the DNA was precipitated by the addition of 0.3 mls 5 M ammonium acetate and 4.3 mls isopropanol, washed in 70% ethanol, and resuspended in 4 mls of TE (10 mM Tris-Cl (pH 8), 1 mM EDTA). The DNA was then phenol-chloroform extracted in the presence of 0.2 mls 3 M sodium acetate and precipitated by the addition of two volumes of ethanol. After the DNA was thoroughly washed in 70% ethanol, it was resuspended in 0.5 mls TE. The DNA was precipitated one more time by the addition of 125 μl 7.5 M ammonium acetate and 1 volume of isopropanol, washed in 70% ethanol, and resuspended in 0.5 mls TE.

5. PCR Amplification of cDNA and Genomic Sequences

PGM cDNA was amplified by PCR in a 100 μl volume containing 1× cloned Pfu buffer (Stratagene), 0.2 mM of each dNTP (dGTP, DATP, TTP, and dCTP), 50 pmol of each primer, and 5 μl of first strand cDNA. The reaction mixture was warmed to 94° C. before adding 5 U of Pfu DNA polymerase (Stratagene). After a 6 minute denaturation step (94° C.), the temperature was lowered to 64° C. for 45 seconds and then brought to 72° C. for 4–5 minutes. Samples were then subjected to 31 cycles of denaturation (45 sec, 94° C.), annealing (45 sec, 62° C.), and extension (72° C., 4–5 minutes), with the final extension being carried out for an additional 2 minutes. PCR amplifications were performed on a Perkin Elmer Cetus DNA Thermal Cycler.

Genomic sequences were amplified by PCR in a similar manner except that extension times were increased to six minutes. PCR reactions contained ~500 ng of genomic DNA.

6. Cloning of PCR-amplified Fragments

PCR-amplified fragments were chloroform extracted to remove the mineral oil overlaying and then ethanol precipitated in the presence of 0.3 M sodium acetate and 10 μl of tRNA.

PCR-amplified fragments being cloned into PCRII-TOPO were first incubated for 10 minutes at 72° C. with Taq polymerase in order to add a 3' dA overhang. They were then cloned into PCRII-TOPO using a TOPO TA cloning kit (Invitrogen).

Polynucleotide kinase was used to add a 5' phosphate before cloning PCR-amplified fragments into SmaI-cut Bluescript or HindIII SmaI-cut Bluescript.

7. Sequencing and Sequence Analysis

Genomic and cDNA clones were first phenol-chloroform extracted and ethanol precipitated before being digested with 20 μg/ml ribonuclease A for 10 minutes at 37° C. The ribonuclease A-treated templates were phenol-chloroform extracted and ethanol precipitated one more time before being used as a template in a thermal cycle sequencing reaction performed using a ThermoSequenase fluorescent primer cycle sequencing kit with 7-deaza-dGTP (Amersham Pharmacia). Reactions were primed off of fluorescently-labeled M13 forward and M13 reverse primers. Sequencing was performed on a Licor automated fluorescent sequencer. Sequencing data was analyzed using the program Sequencher.

B. Results

1. Isolation of bsg Plastid PGM cDNA Clones

Figure 9:
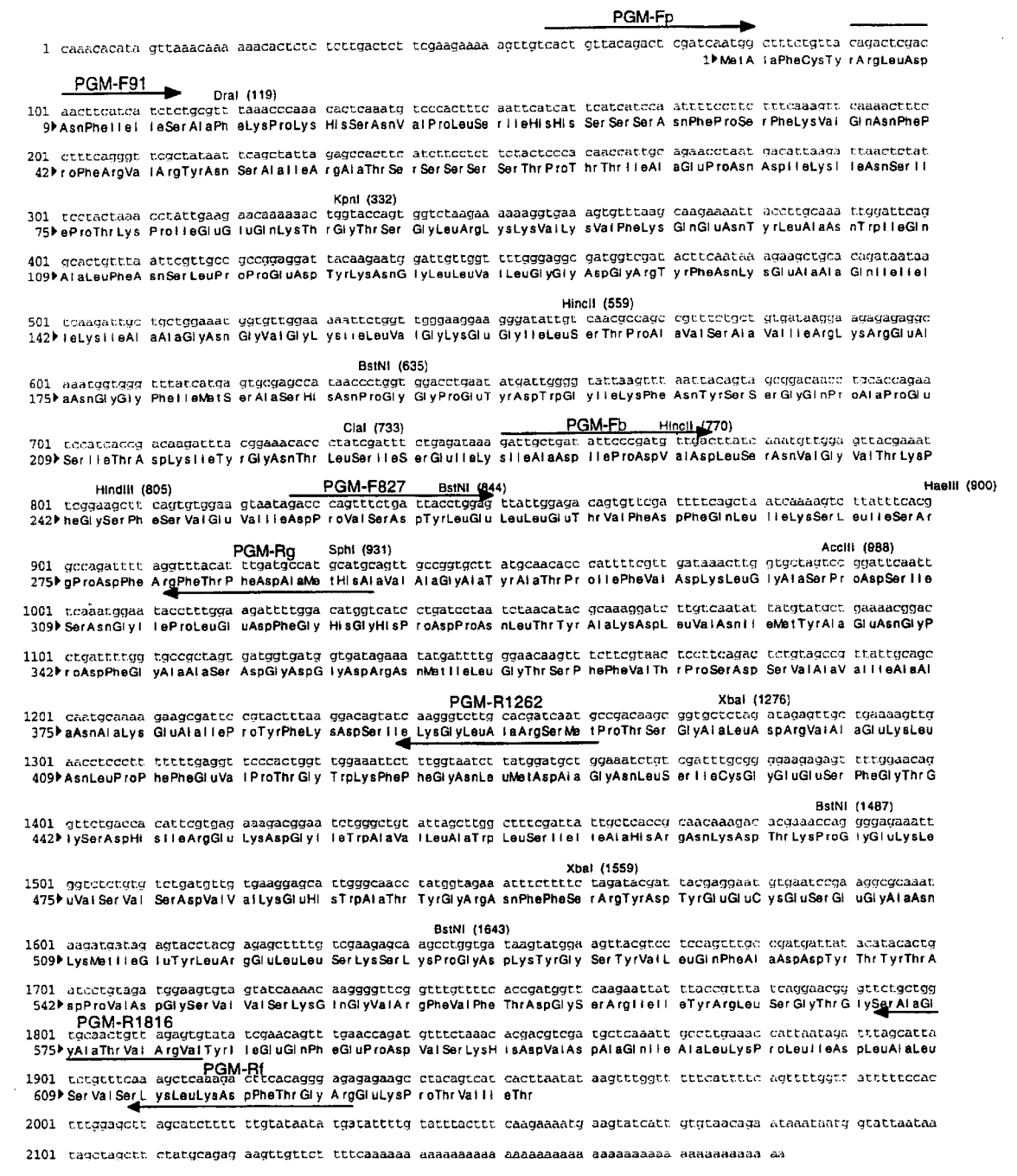
Figure 10:
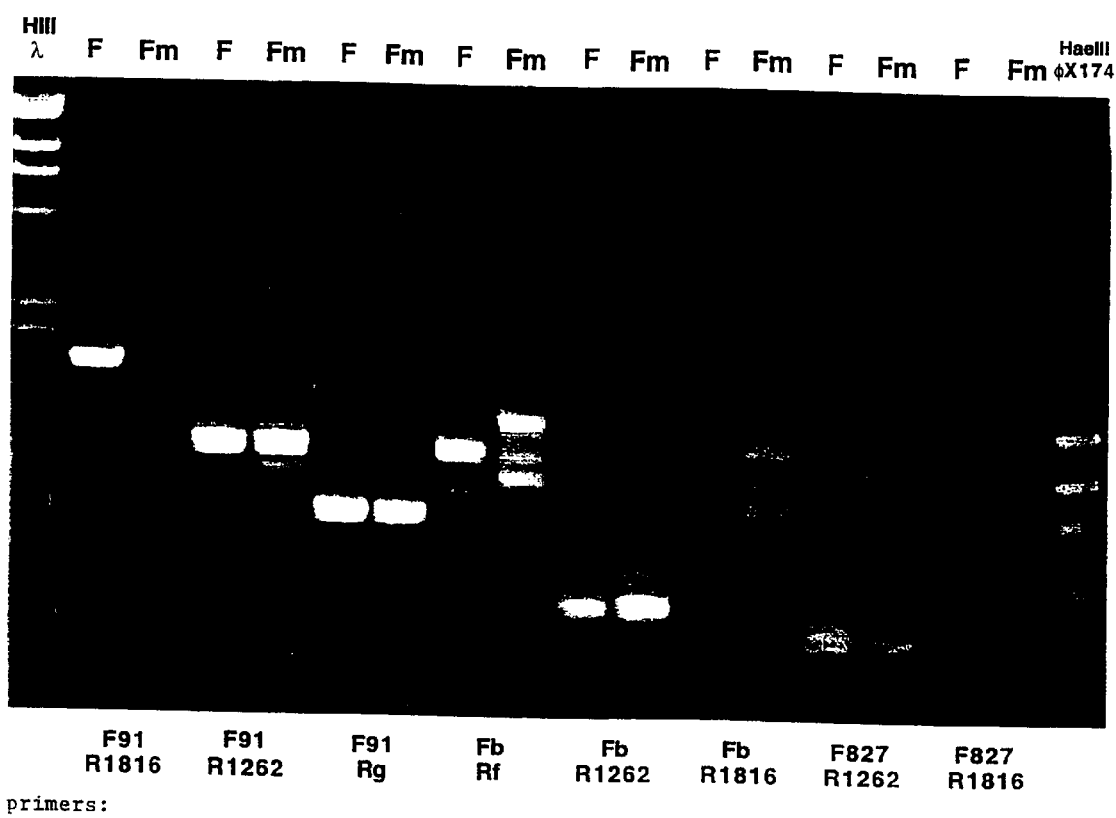
FIG. 10 shows the PCR amplification of PGM plastid cDNA from the wildtype (represented by a "F") and f (represented by a "Fm") poly(A)+seed RNA.

PCR was used to amplify plastid PGM cDNA from the smooth-seed *Pisum sativum* variety, called "Frimousse" (hereinafter referred to as "wildtype") and Frimousse introgressed-bsg (hereinafter referred to as the "mutant") Poly(A)+seed RNA using the primers PGM-Fp (SEQ ID NO:3), PGM-F91 (SEQ ID NO:4), PGM-Fb (SEQ ID NO:5), PGM-F827 (SEQ ID NO:6), PGM-Rg (SEQ ID NO:7), PGM-R1262 (SEQ ID NO:8), PGM-R1816 (SEQ ID NO:9) and PGM-Rf (SEQ ID NO:10) shown in FIG. 9 (SEQ ID NO:11). Most fragments generated by PCR were identical in size in both the mutant and wildtype tissue. However, PCR products amplified from the mutant cDNA encompassing the 555 base pair internal region between primers PGM-R1262 (SEQ ID NO:8) and PGM-R1816 (SEQ ID NO:9) electrophoresed as three bands. One band was approximately 150 base pairs larger than the wildtype band. The second band was approximately 170 base pairs smaller than the wildtype band. The third band was the same size as the wildtype band (see for instance FIG. 10, the Fb/Rf and Fb/R1816 amplifications). PCR products not spanning this 555 base pair internal region did not differ in size between mutant and wildtype. cDNA fragments amplified with primer combinations PGM-Fb/PGM-R1816 (SEQ ID NOS:5 and 9) and PGM-Fp/PGM-Rf (SEQ ID NOS:3 and 10) were then cloned into PCRII-TOPO (Invitrogen) or SmaI-cut Bluescript (Stratagene) for further examination.

PCR was also used to amplify the plastid PGM genomic sequences from the wildtype and mutant. No difference was seen in the size of the amplified bands. Genomic sequences were amplified using the primers PGM-F827 (SEQ ID NO:6) and PGM-R1816 (SEQ ID NO:9). Genomic sequences amplified with these primers were first digested with HindIII and then cloned into HindIII EcoRV-digested Bluescript.

2. Sequence Analysis of PGM cDNA and Genomic Clones

Wildtype Plastid PGM cDNA Sequence

The sequence of the wildtype plastid PGM cDNA is shown in FIG. 11. The region between primers PGM-Fp (SEQ ID NO:3) and PGM-Rf (SEQ ID NO:10) was sequenced in both directions except for a 132 base pair region which was sequenced in only one direction. The region sequenced includes the entire coding region except for the C-terminal 8 amino acid residues. Two independent clones were sequenced throughout this region and no differences were found between these clones.

Wildtype Plastid PGM Genomic Sequence

A partial sequence of the wildtype plastid PGM gene is shown FIG. 7. This gene was sequenced from the HindIII site encoding amino acid residue 244 to primer PGM-R1816 (SEQ ID NO:9), which encodes amino acid residues 573–580. Sequence was conducted in both directions except for a 77 basepair region between nucleotides 1274–1350. More than one independent clone was sequenced except in the region between nucleotides 1016–1350. Within the sequenced region 12 introns were found ranging in size from 79–337 nucleotides.

Mutant PGM Genomic Sequence

The mutant variant of the plastid PGM gene was sequenced in the same region as the wildtype gene except for a 77 base pair gap between nucleotides 1274 and 1350 which was not sequenced at all (FIG. 6). With the exception of the region between nucleotides 959 and 1430, both strands and more than one independent clone were sequenced. Only one difference was found between the wildtype and mutant sequences in the region sequenced, and that was at nucleotide 1594 where A in the 3' splice site dinucleotide AG/ was replaced by T (asterisked 6 and 7).

Mutant Plastid PGM cDNA1 Sequence

Figure 12:
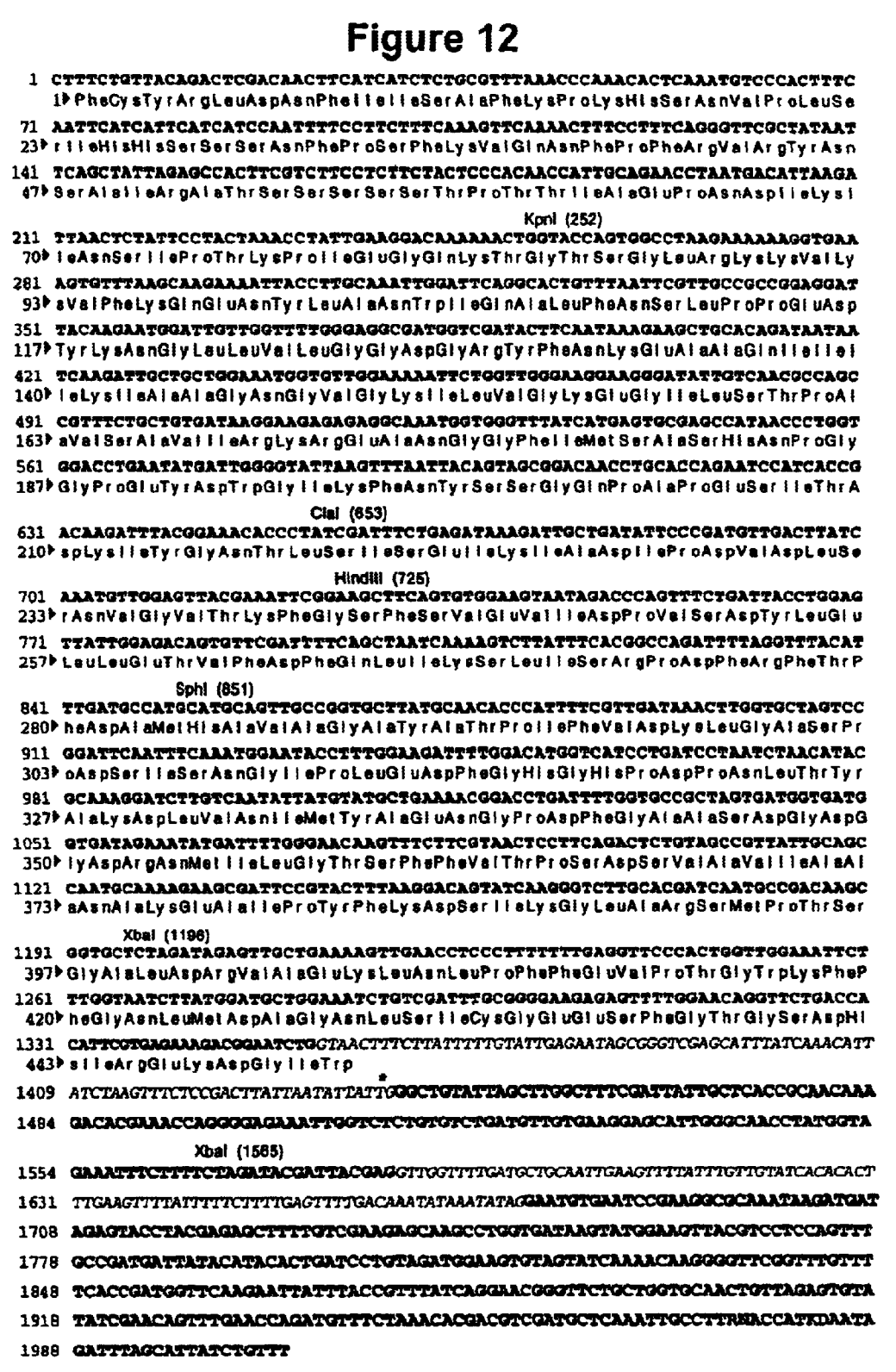

The largest plastid PGM cDNA amplified in the mutant (hereinafter referred to as "cDNA1") is shown in FIG. 12. cDNA1 was sequenced between primers PGM-Fp (SEQ ID NO:3) and PGM-Rf (SEQ ID NO:10). Between nucleotides 888 and 1788 it was sequenced in both directions and between nucleotides 694 and 1915 more than one independently-derived clone was sequenced. cDNA1 retains not only the intron with the mutated 3' splice site (asterisked), but the downstream intron as well (both introns are shown in FIG. 12 in italicized typeface). It is not clear why the downstream intron should be retained. It may be that the mutated intron is normally removed before the downstream intron can be processed or perhaps secondary structure resulting from the retention of the mutated intron prevents processing of the downstream intron.

The retention of the two intron sequences in cDNA1 results in a plastid PGM polypeptide that is immediately truncated by a termination codon near the 5' end of the first retained intron. This results in the C-terminal 173 amino acids being lost from plastid PGM.

Figure 8:
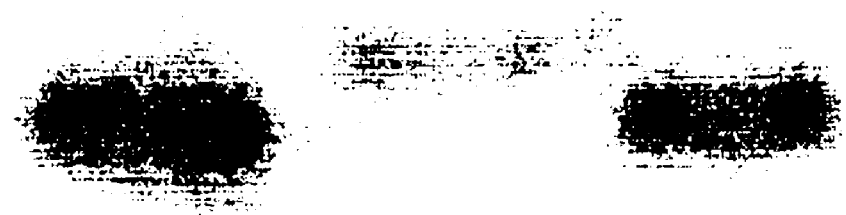
FIG. 8 shows a Northern blot analysis of RNA from wildtype and mutant plants hybridized with a plastid PGM probe. Lane 1 shows the total RNA from a wildtype cotyledon. Lane 2 shows total RNA from a mutant cotyledon. Lane 3 shows total RNA from a wildtype cotyledon.

In the Northern blot shown in FIG. 8, the only transcript seen to accumulate in bsg cotyledons is larger than the wildtype transcript. Since cDNA1 was the only plastid PGM cDNA amplified that is substantially larger than the wildtype transcript, it is believe to correspond to the major transcript accumulating in the bsg mutant.

Mutant Plastid PGM cDNA2 Sequence

The next largest plastid PGM cDNA amplified in the bsg mutant (hereinafter "cDNA2") is shown in FIG. 13. cDNA2 was sequenced in both directions from two independent clones in the region between primers PGM-Fb (SEQ ID NO:5) and PGM-R1816 (SEQ ID NO:9). cDNA2 is roughly the same size as the wildtype sequence but is missing the first 11 nucleotides of the exon directly downstream from the mutated intron. This results from the utilization of a cryptic AG 3' splice site dinucleotide in the downstream exon. As a result, a frameshift mutation is created and 23 amino acids are substituted from the wrong reading frame for the C-terminal 174 amino acids of plastid PGM. In FIG. 13, the two nucleotides flanking the 11 base pair deletion are shown in bold.

Mutant Plastid PGM cDNA3 Sequence

The smallest plastid PGM cDNA amplified in the bsg mutant (hereinafter "cDNA3") is shown in FIG. 14. Two independent cDNA3 clones were sequenced between primers PGM-Fp (SEQ ID NO:3) and PGM-Rf (SEQ ID NO:10). Both strands were sequenced in the region between nucleotides 716 and 1565. Plastic PGM cDNA3 is smaller than the wildtype transcript due to a deletion of the 142 base pair exon immediately downstream from the mutated intron. This results from the substitution of the 3' splice site in the downstream intron for the mutated 3' splice site. As a result, a frameshift mutation is created and 9 amino acids are substituted for the C-terminal 173 amino acids of plastid PGM. In FIG. 14, the two nucleotides flanking this deleted exon are shown in bold.

What is claimed is:

1. A *Pisum sativum* variety which contains a homozygous bsg gene within its genome, wherein said bsg gene contains a mutation in an intron in a 3' splice site of said gene.

2. The *Pisum sativum* variety of claim 1 wherein the mutation is in a dinucleotide AG, wherein the nucleotide A is replaced by nucleotide T.

3. A *Pisum sativum* variety which contains a homozygous bsg gene within its genome, wherein said bsg gene has the nucleotide sequence of SEQ ID NO:1 and said nucleotide sequence contains a mutation in an intron at nucleotide 1594 at the 3' splice site dinucleotide AG, wherein nucleotide A is replaced with nucleotide T.

* * * * *

SEQUENCE LISTING

<160> NUMBER OF SEQ ID NOS: 21

<210> SEQ ID NO 1
<211> LENGTH: 2391

<212> TYPE: DNA
<213> ORGANISM: Pisum sativum
<220> FEATURE:
<221> NAME/KEY: misc_feature
<222> LOCATION: (1274)..(1350)
<223> OTHER INFORMATION: N=A or C or G or T/U

<400> SEQUENCE: 1

| | | | | | |
|---|---|---|---|---|---|
| aagcttcagt | gtggaagtaa | tagacccagt | ttctgattac | ctggagttat | tggaggtcaa | 60 |
| aataatcttt | tttcttcatt | ataatccagt | agaatgattc | atgcaagctc | gatctctgtg | 120 |
| ttgagagttt | tatttcattt | catttcgtct | aagtttattt | gttattattt | tttgtgcaga | 180 |
| cagtgttcga | ttttcagcta | atcaaaagtc | ttatttcacg | ccagattttt | aggtacaacc | 240 |
| ttaacattta | ttccaccata | atccaaatct | tggcacattg | tctagaatct | gattgtgtta | 300 |
| aattttttta | ttttaggttt | acatttgatg | ccatgcatgc | agttgccggt | gcttatgcaa | 360 |
| cacccatttt | cgttgataaa | cttggtgcta | gtccggtata | gttcttcccc | ttttactctt | 420 |
| gtacatagcg | ggtacaagtt | tatacggtat | tgttgatttt | gggtgttaag | tatgcaatgt | 480 |
| aggattcaat | ttcaaatgga | atacctttgg | aagattttgg | acatggtcat | cctgatccta | 540 |
| atctaacgtg | agtttagttt | tatattttcg | acattgtgtt | ttcaatcatt | agtaaattgt | 600 |
| ttttgattct | aatgtttatt | gaacagatac | gcaaaggatc | ttgtcaatat | tatgtatgct | 660 |
| gaaaacggac | ctgattttgg | tgccgctagt | gatggtatgc | gagattttag | ttattttga | 720 |
| aatttaactt | gtttccgttg | ataaatcctt | gtgcaacaat | gttttgtctg | aacccaagag | 780 |
| caattggatg | agatggtaag | agatctcttt | cagcttaacc | tgaggtcctg | agtttgaact | 840 |
| cagtcctggg | cacgcaacag | tgctaaattc | tcttgagaga | gaactttgcc | gtccattgcg | 900 |
| gtcctcccca | gctcgaggga | ttagtctctg | cagttgcacg | cagaggatac | ccgattttta | 960 |
| ctgtaaaaaa | acaatgtttt | ttgtctgcat | ttgtttactt | gataatgttt | atgtatttta | 1020 |
| actttcgttt | aggtgatggt | gatagaaata | tgattttggg | aacaagtttc | ttcgtaactc | 1080 |
| cttcagactc | tgtagccgtt | attgcagcca | atgcaaaaga | agcgattccg | tactttaagg | 1140 |
| acagtatcaa | ggtagaaagt | ttgtgcatat | catattattc | acaagtattc | gttgttgtaa | 1200 |
| aacagaagtg | tcattgttct | gtattgtaat | tgcagggtct | tgcacgatca | atgccgacaa | 1260 |
| gcggtgctct | agannnnnnn | nnnnnnnnnn | nnnnnnnnnn | nnnnnnnnnn | nnnnnnnnnn | 1320 |
| nnnnnnnnnn | nnnnnnnnnn | nnnnnnnnnn | tctagattat | ggttctcgaa | tgacagacgg | 1380 |
| acctcgggtg | caggttccca | ctggttggaa | attctttggt | aatcttatgg | atgctggaaa | 1440 |
| tctgtcgatt | tgcggggaag | agagttttgg | aacaggttct | gaccacattc | gtgagaaaga | 1500 |
| cggaatctgg | taactttctt | attttgtat | tgagaatagc | gggtcgagca | tttatcaaac | 1560 |
| attatctaag | tttctccgac | ttattaatat | tattgggctg | tattagcttg | gctttcgatt | 1620 |
| attgctcacc | gcaacaaaga | cacgaaacca | ggggagaaat | tggtctctgt | gtctgatgtt | 1680 |
| gtgaaggagc | attgggcaac | ctatggtaga | aatttctttt | ctagatacga | ttacgaggtt | 1740 |
| ggttttgatg | ctgcaattga | agtttatttt | gttgtatcac | acactttgaa | gttttatttt | 1800 |
| tcttttgagt | tttgacaaat | ataaatatag | gaatgtgaat | ccgaaggcgc | aaataagatg | 1860 |
| atagagtacc | tacgagagct | tttgtcgaag | agcaagcctg | gtgataagta | tggtaagtta | 1920 |
| ctcacaacca | ctttcttatc | acagacacgg | agacacggac | accaaacacg | acattgacat | 1980 |
| tggcacgtaa | tcattagcat | acactttccc | tgagtatatt | taaagtgtga | tgagttttct | 2040 |
| tgtacaggaa | gttacgtcct | ccagtttgcc | gatgattata | catacactga | tcctgtaagt | 2100 |

-continued

| | |
|---|---|
| tcttacaact tcacattctc atcatgttga tttttgtttc ttcaacttac ggtaaatcaa | 2160 |
| ccatagttca aattctgatt gaataaaaac atgcaggtag atggaagtgt agtatcaaaa | 2220 |
| caagggttc ggtttgtttt caccgatggt tcaagaatta tttaccgttt atcagtaagt | 2280 |
| aacgtctgtt taattactta cccgaaaaat ttatgaaatg aaatattaag tgattactta | 2340 |
| cggtgttttt gtttacaggg aacgggttct gctggtgcaa ctgttagagt g | 2391 |

<210> SEQ ID NO 2
<211> LENGTH: 2391
<212> TYPE: DNA
<213> ORGANISM: Pisum sativum

<400> SEQUENCE: 2

| | |
|---|---|
| aagcttcagt gtggaagtaa tagacccagt ttctgattac ctggagttat tggaggtcaa | 60 |
| aataatcttt tttcttcatt ataatccagt agaatgattc atgcaagctc gatctctgtg | 120 |
| ttgagagttt tatttcattt catttcgtct aagtttattt gttattattt tttgtgcaga | 180 |
| cagtgttcga ttttcagcta atcaaaagtc ttatttcacg gccagatttt aggtacaacc | 240 |
| ttaacattta ttccaccata atccaaatct tggcacattg tctagaatct gattgtgtta | 300 |
| aatttttta ttttaggttt acatttgatg ccatgcatgc agttgccggt gcttatgcaa | 360 |
| cacccatttt cgttgataaa cttggtgcta gtccggtata gttcttcccc ttttactctt | 420 |
| gtacatagcg ggtacaagtt tatacggtat tgttgatttt gggtgttaag tatgcaatgt | 480 |
| aggattcaat ttcaaatgga atacctttgg aagattttgg acatggtcat cctgatccta | 540 |
| atctaacgtg agtttagttt tatattttcg acattgtgtt ttcaatcatt agtaaattgt | 600 |
| ttttgattct aatgtttatt gaacagatac gcaaaggatc ttgtcaatat tatgtatgct | 660 |
| gaaaacggac ctgattttgg tgccgctagt gatggtatgc gagattttag ttattttga | 720 |
| aatttaactt gtttccgttg ataaatcctt gtgcaacaat gttttgtctg aacccaagag | 780 |
| caattggatg agatggtaag agatctcttt cagcttaacc tgaggtcctg agtttgaact | 840 |
| cagtcctggg cacgcaacag tgctaaattc tcttgagaga gaactttgcc gtccattgcg | 900 |
| gtcctcccca gctcgaggga ttagtctctg cagttgcacg cagaggatac ccgattttta | 960 |
| ctgtaaaaaa acaatgtttt ttgtctgcat ttgtttactt gataatgttt atgtatttta | 1020 |
| actttcgttt aggtgatggt gatagaaata tgattttggg aacaagtttc ttcgtaactc | 1080 |
| cttcagactc tgtagccgtt attgcagcca atgcaaaaga agcgattccg tactttaagg | 1140 |
| acagtatcaa ggtagaaagt ttgtgcatat catattattc acaagtattc gttgttgtaa | 1200 |
| aacagaagtg tcattgttct gtattgtaat tgcagggtct tgcacgatca atgccgacaa | 1260 |
| gcggtgctct agatagagtt gctgaaaagt tgaacctccc tttttttgag gtatagtatg | 1320 |
| attttacatt gttgttgcgt ttagaattat tctagattat ggttctcgaa tgacagacgg | 1380 |
| acctcgggtg caggttccca ctggttggaa attctttggt aatcttatgg atgctggaaa | 1440 |
| tctgtcgatt tgcggggaag agagttttgg aacaggttct gaccacattc gtgagaaaga | 1500 |
| cggaatctgg taactttctt attttttgtat tgagaatagc gggtcgagca tttatcaaac | 1560 |
| attatctaag tttctccgac ttattaatat tatagggctg tattagcttg ctttcgatt | 1620 |
| attgctcacc gcaacaaaga cacgaaacca ggggagaaat tggtctctgt gtctgatgtt | 1680 |
| gtgaaggagc attgggcaac ctatggtaga aatttctttt ctagatacga ttacgaggtt | 1740 |
| ggttttgatg ctgcaattga agttttattt gttgtatcac acactttgaa gttttatttt | 1800 |
| tcttttgagt tttgacaaat ataaatatag gaatgtgaat ccgaaggcgc aaataagatg | 1860 |

-continued

```
atagagtacc tacgagagct tttgtcgaag agcaagcctg gtgataagta tggtaagtta    1920
ctcacaacca ctttcttatc acagacacgg agacacggac accaaacacg acattgacat    1980
tggcacgtaa tcattagcat acactttccc tgagtatatt taaagtgtga tgagtttttct   2040 tgtacaggaa gttacgtcct ccagtttgcc gatgattata catacactga tcctgtaagt    2100
tcttacaact tcacattctc atcatgttga tttttgtttc ttcaacttac ggtaaatcaa    2160
ccatagttca aattctgatt gaataaaaac atgcaggtag atggaagtgt agtatcaaaa    2220 caagggttc ggtttgtttt caccgatggt tcaagaatta tttaccgttt atcagtaagt    2280
aacgtctgtt taattactta cccgaaaaat ttatgaaatg aaatattaag tgattactta    2340
cggtgttttt gtttacaggg aacgggttct gctggtgcaa ctgttagagt g             2391
```

<210> SEQ ID NO 3
<211> LENGTH: 24
<212> TYPE: DNA
<213> ORGANISM: Pisum sativum

<400> SEQUENCE: 3
cactgttaca gactcgatca atgg                                            24

<210> SEQ ID NO 4
<211> LENGTH: 24
<212> TYPE: DNA
<213> ORGANISM: Pisum sativum

<400> SEQUENCE: 4
cagactcgac aacttcatca tctc                                            24

<210> SEQ ID NO 5
<211> LENGTH: 24
<212> TYPE: DNA
<213> ORGANISM: Pisum sativum

<400> SEQUENCE: 5
gattgctgat attcccgatg ttga                                            24

<210> SEQ ID NO 6
<211> LENGTH: 24
<212> TYPE: DNA
<213> ORGANISM: Pisum sativum

<400> SEQUENCE: 6
gacccagttt ctgattacct ggag                                            24

<210> SEQ ID NO 7
<211> LENGTH: 24
<212> TYPE: DNA
<213> ORGANISM: Pisum sativum

<400> SEQUENCE: 7
catgcatggc atcaaatgta aacc                                            24

<210> SEQ ID NO 8
<211> LENGTH: 24
<212> TYPE: DNA
<213> ORGANISM: Pisum sativum

<400> SEQUENCE: 8
gcattgatcg tgcaagaccc ttga                                            24

-continued

```
<210> SEQ ID NO 9
<211> LENGTH: 24
<212> TYPE: DNA
<213> ORGANISM: Pisum sativum

<400> SEQUENCE: 9
cactctaaca gttgcaccag caga                                              24

<210> SEQ ID NO 10
<211> LENGTH: 24
<212> TYPE: DNA
<213> ORGANISM: Pisum sativum

<400> SEQUENCE: 10
tccctgtgaa gtctttgagc tttg                                              24

<210> SEQ ID NO 11
<211> LENGTH: 2182
<212> TYPE: DNA
<213> ORGANISM: Pisum sativum
<220> FEATURE:
<221> NAME/KEY: CDS
<222> LOCATION: (77)..(1954)
<223> OTHER INFORMATION:

<400> SEQUENCE: 11
caaacacata gttaaacaaa aaacactctc tcttgactct tcgaagaaaa agttgtcact         60
gttacagact cgatca atg gct ttc tgt tac aga ctc gac aac ttc atc atc       112
                  Met Ala Phe Cys Tyr Arg Leu Asp Asn Phe Ile Ile
                   1               5                  10 tct gcg ttt aaa ccc aaa cac tca aat gtc cca ctt tca att cat cat         160
Ser Ala Phe Lys Pro Lys His Ser Asn Val Pro Leu Ser Ile His His
         15                  20                  25 tca tca tcc aat ttt cct tct ttc aaa gtt caa aac ttt cct ttc agg         208
Ser Ser Ser Asn Phe Pro Ser Phe Lys Val Gln Asn Phe Pro Phe Arg
     30                  35                  40 gtt cgc tat aat tca gct att aga gcc act tca tct tcc tct tct act         256
Val Arg Tyr Asn Ser Ala Ile Arg Ala Thr Ser Ser Ser Ser Ser Thr
 45                  50                  55                  60 ccc aca acc att gca gaa cct aat gac att aag att aac tct att cct         304
Pro Thr Thr Ile Ala Glu Pro Asn Asp Ile Lys Ile Asn Ser Ile Pro
                 65                  70                  75 act aaa cct att gaa gaa caa aaa act ggt acc agt ggt cta aga aaa         352
Thr Lys Pro Ile Glu Glu Gln Lys Thr Gly Thr Ser Gly Leu Arg Lys
             80                  85                  90 aag gtg aaa gtg ttt aag caa gaa aat tac ctt gca aat tgg att cag         400
Lys Val Lys Val Phe Lys Gln Glu Asn Tyr Leu Ala Asn Trp Ile Gln
         95                 100                 105 gca ctg ttt aat tcg ttg ccg ccg gag gat tac aag aat gga ttg ttg         448
Ala Leu Phe Asn Ser Leu Pro Pro Glu Asp Tyr Lys Asn Gly Leu Leu
    110                 115                 120 gtt ttg gga ggc gat ggt cga tac ttc aat aaa gaa gct gca cag ata         496
Val Leu Gly Gly Asp Gly Arg Tyr Phe Asn Lys Glu Ala Ala Gln Ile
125                 130                 135                 140 ata atc aag att gct gct gga aat ggt gtt gga aaa att ctg gtt ggg         544
Ile Ile Lys Ile Ala Ala Gly Asn Gly Val Gly Lys Ile Leu Val Gly
                145                 150                 155 aag gaa ggg ata ttg tca acg cca gcc gtt tct gct gtg ata agg aag         592
Lys Glu Gly Ile Leu Ser Thr Pro Ala Val Ser Ala Val Ile Arg Lys
            160                 165                 170 aga gag gca aat ggt ggg ttt atc atg agt gcg agc cat aac cct ggt         640
```

```
                                                                  -continued Arg Glu Ala Asn Gly Gly Phe Ile Met Ser Ala Ser His Asn Pro Gly
            175                 180                 185 gga cct gaa tat gat tgg ggt att aag ttt aat tac agt agc gga caa    688
Gly Pro Glu Tyr Asp Trp Gly Ile Lys Phe Asn Tyr Ser Ser Gly Gln
    190                 195                 200 cct gca cca gaa tcc atc acc gac aag att tac gga aac acc cta tcg    736
Pro Ala Pro Glu Ser Ile Thr Asp Lys Ile Tyr Gly Asn Thr Leu Ser
205                 210                 215                 220 att tct gag ata aag att gct gat att ccc gat gtt gac tta tca aat    784
Ile Ser Glu Ile Lys Ile Ala Asp Ile Pro Asp Val Asp Leu Ser Asn
                225                 230                 235 gtt gga gtt acg aaa ttc gga agc ttc agt gtg gaa gta ata gac cca    832
Val Gly Val Thr Lys Phe Gly Ser Phe Ser Val Glu Val Ile Asp Pro
            240                 245                 250 gtt tct gat tac ctg gag tta ttg gag aca gtg ttc gat ttt cag cta    880
Val Ser Asp Tyr Leu Glu Leu Leu Glu Thr Val Phe Asp Phe Gln Leu
        255                 260                 265 atc aaa agt ctt att tca cgg cca gat ttt agg ttt aca ttt gat gcc    928
Ile Lys Ser Leu Ile Ser Arg Pro Asp Phe Arg Phe Thr Phe Asp Ala
270                 275                 280 atg cat gca gtt gcc ggt gct tat gca aca ccc att ttc gtt gat aaa    976
Met His Ala Val Ala Gly Ala Tyr Ala Thr Pro Ile Phe Val Asp Lys
285                 290                 295                 300 ctt ggt gct agt ccg gat tca att tca aat gga ata cct ttg gaa gat    1024
Leu Gly Ala Ser Pro Asp Ser Ile Ser Asn Gly Ile Pro Leu Glu Asp
                305                 310                 315 ttt gga cat ggt cat cct gat cct aat cta aca tac gca aag gat ctt    1072
Phe Gly His Gly His Pro Asp Pro Asn Leu Thr Tyr Ala Lys Asp Leu
            320                 325                 330 gtc aat att atg tat gct gaa aac gga cct gat ttt ggt gcc gct agt    1120
Val Asn Ile Met Tyr Ala Glu Asn Gly Pro Asp Phe Gly Ala Ala Ser
        335                 340                 345 gat ggt gat ggt gat aga aat atg att ttg gga aca agt ttc ttc gta    1168
Asp Gly Asp Gly Asp Arg Asn Met Ile Leu Gly Thr Ser Phe Phe Val
350                 355                 360 act cct tca gac tct gta gcc gtt att gca gcc aat gca aaa gaa gcg    1216
Thr Pro Ser Asp Ser Val Ala Val Ile Ala Ala Asn Ala Lys Glu Ala
365                 370                 375                 380 att ccg tac ttt aag gac agt atc aag ggt ctt gca cga tca atg ccg    1264
Ile Pro Tyr Phe Lys Asp Ser Ile Lys Gly Leu Ala Arg Ser Met Pro
                385                 390                 395 aca agc ggt gct cta gat aga gtt gct gaa aag ttg aac ctc cct ttt    1312
Thr Ser Gly Ala Leu Asp Arg Val Ala Glu Lys Leu Asn Leu Pro Phe
            400                 405                 410 ttt gag gtt ccc act ggt tgg aaa ttc ttt ggt aat ctt atg gat gct    1360
Phe Glu Val Pro Thr Gly Trp Lys Phe Phe Gly Asn Leu Met Asp Ala
        415                 420                 425 gga aat ctg tcg att tgc ggg gaa gag agt ttt gga aca ggt tct gac    1408
Gly Asn Leu Ser Ile Cys Gly Glu Glu Ser Phe Gly Thr Gly Ser Asp
430                 435                 440 cac att cgt gag aaa gac gga atc tgg gct gta tta gct tgg ctt tcg    1456
His Ile Arg Glu Lys Asp Gly Ile Trp Ala Val Leu Ala Trp Leu Ser
445                 450                 455                 460 att att gct cac cgc aac aaa gac acg aaa cca ggg gag aaa ttg gtc    1504
Ile Ile Ala His Arg Asn Lys Asp Thr Lys Pro Gly Glu Lys Leu Val
                465                 470                 475 tct gtg tct gat gtt gtg aag gag cat tgg gca acc tat ggt aga aat    1552
Ser Val Ser Asp Val Val Lys Glu His Trp Ala Thr Tyr Gly Arg Asn
            480                 485                 490
```

```
ttc ttt tct aga tac gat tac gag gaa tgt gaa tcc gaa ggc gca aat    1600
Phe Phe Ser Arg Tyr Asp Tyr Glu Glu Cys Glu Ser Glu Gly Ala Asn
            495                 500                 505 aag atg ata gag tac cta cga gag ctt ttg tcg aag agc aag cct ggt    1648
Lys Met Ile Glu Tyr Leu Arg Glu Leu Leu Ser Lys Ser Lys Pro Gly
    510                 515                 520 gat aag tat gga agt tac gtc ctc cag ttt gcc gat gat tat aca tac    1696
Asp Lys Tyr Gly Ser Tyr Val Leu Gln Phe Ala Asp Asp Tyr Thr Tyr
525                 530                 535                 540 act gat cct gta gat gga agt gta gta tca aaa caa ggg gtt cgg ttt    1744
Thr Asp Pro Val Asp Gly Ser Val Val Ser Lys Gln Gly Val Arg Phe
                545                 550                 555 gtt ttc acc gat ggt tca aga att att tac cgt tta tca gga acg ggt    1792
Val Phe Thr Asp Gly Ser Arg Ile Ile Tyr Arg Leu Ser Gly Thr Gly
            560                 565                 570 tct gct ggt gca act gtt aga gtg tat atc gaa cag ttt gaa cca gat    1840
Ser Ala Gly Ala Thr Val Arg Val Tyr Ile Glu Gln Phe Glu Pro Asp
        575                 580                 585 gtt tct aaa cac gac gtc gat gct caa att gcc ttg aaa cca tta ata    1888
Val Ser Lys His Asp Val Asp Ala Gln Ile Ala Leu Lys Pro Leu Ile
    590                 595                 600 gat tta gca tta tct gtt tca aag ctc aaa gac ttc aca ggg aga gag    1936
Asp Leu Ala Leu Ser Val Ser Lys Leu Lys Asp Phe Thr Gly Arg Glu
605                 610                 615                 620 aag cct aca gtc atc act taatataagt ttggttttc attttcagtt            1984
Lys Pro Thr Val Ile Thr
                625 ttggttattt ttccactttg gagcttagca tcttttttgt ataatatgat attttgtatt  2044 tactttcaag aaaatgaagt atcattgtgt aacagaataa ataatggtat taataatagc  2104 tagcttctat gcagagaagt tgttctttc aaaaaaaaaa aaaaaaaaaa aaaaaaaaaa   2164 aaaaaaaaaa aaaaaaaa                                                2182

<210> SEQ ID NO 12
<211> LENGTH: 626
<212> TYPE: PRT
<213> ORGANISM: Pisum sativum

<400> SEQUENCE: 12

Met Ala Phe Cys Tyr Arg Leu Asp Asn Phe Ile Ile Ser Ala Phe Lys
1               5                   10                  15

Pro Lys His Ser Asn Val Pro Leu Ser Ile His His Ser Ser Ser Asn
            20                  25                  30

Phe Pro Ser Phe Lys Val Gln Asn Phe Pro Phe Arg Val Arg Tyr Asn
        35                  40                  45

Ser Ala Ile Arg Ala Thr Ser Ser Ser Ser Thr Pro Thr Thr Ile
    50                  55                  60

Ala Glu Pro Asn Asp Ile Lys Ile Asn Ser Ile Pro Thr Lys Pro Ile
65                  70                  75                  80

Glu Glu Gln Lys Thr Gly Thr Ser Gly Leu Arg Lys Lys Val Lys Val
                85                  90                  95

Phe Lys Gln Glu Asn Tyr Leu Ala Asn Trp Ile Gln Ala Leu Phe Asn
            100                 105                 110

Ser Leu Pro Pro Glu Asp Tyr Lys Asn Gly Leu Leu Val Leu Gly Gly
        115                 120                 125

Asp Gly Arg Tyr Phe Asn Lys Glu Ala Ala Gln Ile Ile Ile Lys Ile
    130                 135                 140
```

-continued

```
Ala Ala Gly Asn Gly Val Gly Lys Ile Leu Val Gly Lys Glu Gly Ile
145                 150                 155                 160

Leu Ser Thr Pro Ala Val Ser Ala Val Ile Arg Lys Arg Glu Ala Asn
                165                 170                 175

Gly Gly Phe Ile Met Ser Ala Ser His Asn Pro Gly Gly Pro Glu Tyr
                180                 185                 190

Asp Trp Gly Ile Lys Phe Asn Tyr Ser Ser Gly Gln Pro Ala Pro Glu
            195                 200                 205

Ser Ile Thr Asp Lys Ile Tyr Gly Asn Thr Leu Ser Ile Ser Glu Ile
        210                 215                 220

Lys Ile Ala Asp Ile Pro Asp Val Asp Leu Ser Asn Val Gly Val Thr
225                 230                 235                 240

Lys Phe Gly Ser Phe Ser Val Glu Val Ile Asp Pro Val Ser Asp Tyr
                245                 250                 255

Leu Glu Leu Leu Glu Thr Val Phe Asp Phe Gln Leu Ile Lys Ser Leu
                260                 265                 270

Ile Ser Arg Pro Asp Phe Arg Phe Thr Phe Asp Ala Met His Ala Val
            275                 280                 285

Ala Gly Ala Tyr Ala Thr Pro Ile Phe Val Asp Lys Leu Gly Ala Ser
290                 295                 300

Pro Asp Ser Ile Ser Asn Gly Ile Pro Leu Glu Asp Phe Gly His Gly
305                 310                 315                 320

His Pro Asp Pro Asn Leu Thr Tyr Ala Lys Asp Leu Val Asn Ile Met
                325                 330                 335

Tyr Ala Glu Asn Gly Pro Asp Phe Gly Ala Ala Ser Asp Gly Asp Gly
            340                 345                 350

Asp Arg Asn Met Ile Leu Gly Thr Ser Phe Phe Val Thr Pro Ser Asp
            355                 360                 365

Ser Val Ala Val Ile Ala Ala Asn Ala Lys Glu Ala Ile Pro Tyr Phe
370                 375                 380

Lys Asp Ser Ile Lys Gly Leu Ala Arg Ser Met Pro Thr Ser Gly Ala
385                 390                 395                 400

Leu Asp Arg Val Ala Glu Lys Leu Asn Leu Pro Phe Phe Glu Val Pro
                405                 410                 415

Thr Gly Trp Lys Phe Phe Gly Asn Leu Met Asp Ala Gly Asn Leu Ser
            420                 425                 430

Ile Cys Gly Glu Glu Ser Phe Gly Thr Gly Ser Asp His Ile Arg Glu
        435                 440                 445

Lys Asp Gly Ile Trp Ala Val Leu Ala Trp Leu Ser Ile Ile Ala His
450                 455                 460

Arg Asn Lys Asp Thr Lys Pro Gly Glu Lys Leu Val Ser Val Ser Asp
465                 470                 475                 480

Val Val Lys Glu His Trp Ala Thr Tyr Gly Arg Asn Phe Phe Ser Arg
                485                 490                 495

Tyr Asp Tyr Glu Glu Cys Glu Ser Glu Gly Ala Asn Lys Met Ile Glu
            500                 505                 510

Tyr Leu Arg Glu Leu Leu Ser Lys Ser Lys Pro Gly Asp Lys Tyr Gly
        515                 520                 525

Ser Tyr Val Leu Gln Phe Ala Asp Asp Tyr Thr Tyr Thr Asp Pro Val
530                 535                 540

Asp Gly Ser Val Val Ser Lys Gln Gly Val Arg Phe Val Phe Thr Asp
545                 550                 555                 560

Gly Ser Arg Ile Ile Tyr Arg Leu Ser Gly Thr Gly Ser Ala Gly Ala
```

```
                         565                 570                 575
Thr Val Arg Val Tyr Ile Glu Gln Phe Glu Pro Asp Val Ser Lys His
            580                 585                 590
Asp Val Asp Ala Gln Ile Ala Leu Lys Pro Leu Ile Asp Leu Ala Leu
            595                 600                 605
Ser Val Ser Lys Leu Lys Asp Phe Thr Gly Arg Glu Lys Pro Thr Val
    610                 615                 620
Ile Thr
625

<210> SEQ ID NO 13
<211> LENGTH: 1875
<212> TYPE: DNA
<213> ORGANISM: Pisum sativum
<220> FEATURE:
<221> NAME/KEY: CDS
<222> LOCATION: (21)..(1874)
<223> OTHER INFORMATION:

<400> SEQUENCE: 13
cactgttaca gactcgatca atg gct ttc tgt tac aga ctc gac aac ttc atc       53
                      Met Ala Phe Cys Tyr Arg Leu Asp Asn Phe Ile
                       1               5                  10 atc tct gcg ttt aaa ccc aaa cac tca aat gtc cca ctt tca att cat       101
Ile Ser Ala Phe Lys Pro Lys His Ser Asn Val Pro Leu Ser Ile His
             15                  20                  25 cat tca tca tcc aat ttt cct tct ttc aaa gtt caa aac ttt cct ttc       149
His Ser Ser Ser Asn Phe Pro Ser Phe Lys Val Gln Asn Phe Pro Phe
         30                  35                  40 agg gtt cgc tat aat tca gct att aga gcc act tcg tct tcc tct tct       197
Arg Val Arg Tyr Asn Ser Ala Ile Arg Ala Thr Ser Ser Ser Ser Ser
     45                  50                  55 act ccc aca acc att gca gaa cct aat gac att aag att aac tct att       245
Thr Pro Thr Thr Ile Ala Glu Pro Asn Asp Ile Lys Ile Asn Ser Ile
 60                  65                  70                  75 cct act aaa cct att gaa gga caa aaa act ggt acc agt ggc cta aga       293
Pro Thr Lys Pro Ile Glu Gly Gln Lys Thr Gly Thr Ser Gly Leu Arg
                 80                  85                  90 aaa aag gtg aaa gtg ttt aag caa gaa aat tac ctt gca aat tgg att       341
Lys Lys Val Lys Val Phe Lys Gln Glu Asn Tyr Leu Ala Asn Trp Ile
             95                 100                 105 cag gca ctg ttt aat tcg ttg ccg ccg gag gat tac aag aat gga ttg       389
Gln Ala Leu Phe Asn Ser Leu Pro Pro Glu Asp Tyr Lys Asn Gly Leu
        110                 115                 120 ttg gtt ttg gga ggc gat ggt cga tac ttc aat aaa gaa gct gca cag       437
Leu Val Leu Gly Gly Asp Gly Arg Tyr Phe Asn Lys Glu Ala Ala Gln
    125                 130                 135 ata ata atc aag att gct gct gga aat ggt gtt gga aaa att ctg gtt       485
Ile Ile Ile Lys Ile Ala Ala Gly Asn Gly Val Gly Lys Ile Leu Val
140                 145                 150                 155 ggg aag gaa ggg ata ttg tca acg cca gcc gtt tct gct gtg ata agg       533
Gly Lys Glu Gly Ile Leu Ser Thr Pro Ala Val Ser Ala Val Ile Arg
                160                 165                 170 aag aga gag gca aat ggt ggg ttt atc atg agt gcg agc cat aac cct       581
Lys Arg Glu Ala Asn Gly Gly Phe Ile Met Ser Ala Ser His Asn Pro
            175                 180                 185 ggt gga cct gaa tat gat tgg ggt att aag ttt aat tac agt agc gga       629
Gly Gly Pro Glu Tyr Asp Trp Gly Ile Lys Phe Asn Tyr Ser Ser Gly
        190                 195                 200 caa cct gca cca gaa tcc atc acc gac aag att tac gga aac acc cta       677
```

```
Gln Pro Ala Pro Glu Ser Ile Thr Asp Lys Ile Tyr Gly Asn Thr Leu
    205                 210                 215 tcg att tct gag ata aag att gct gat att ccc gat gtt gac tta tca      725
Ser Ile Ser Glu Ile Lys Ile Ala Asp Ile Pro Asp Val Asp Leu Ser
220                 225                 230                 235 aat gtt gga gtt acg aaa ttc gga agc ttc agt gtg gaa gta ata gac      773
Asn Val Gly Val Thr Lys Phe Gly Ser Phe Ser Val Glu Val Ile Asp
                240                 245                 250 cca gtt tct gat tac ctg gag tta ttg gag aca gtg ttc gat ttt cag      821
Pro Val Ser Asp Tyr Leu Glu Leu Leu Glu Thr Val Phe Asp Phe Gln
            255                 260                 265 cta atc aaa agt ctt att tca cgg cca gat ttt agg ttt aca ttt gat      869
Leu Ile Lys Ser Leu Ile Ser Arg Pro Asp Phe Arg Phe Thr Phe Asp
        270                 275                 280 gcc atg cat gca gtt gcc ggt gct tat gca aca ccc att ttc gtt gat      917
Ala Met His Ala Val Ala Gly Ala Tyr Ala Thr Pro Ile Phe Val Asp
    285                 290                 295 aaa ctt ggt gct agt ccg gat tca att tca aat gga ata cct ttg gaa      965
Lys Leu Gly Ala Ser Pro Asp Ser Ile Ser Asn Gly Ile Pro Leu Glu
300                 305                 310                 315 gat ttt gga cat ggt cat cct gat cct aat cta aca tac gca aag gat     1013
Asp Phe Gly His Gly His Pro Asp Pro Asn Leu Thr Tyr Ala Lys Asp
                320                 325                 330 ctt gtc aat att atg tat gct gaa aac gga cct gat ttt ggt gcc gct     1061
Leu Val Asn Ile Met Tyr Ala Glu Asn Gly Pro Asp Phe Gly Ala Ala
            335                 340                 345 agt gat ggt gat ggt gat aga aat atg att ttg gga aca agt ttc ttc     1109
Ser Asp Gly Asp Gly Asp Arg Asn Met Ile Leu Gly Thr Ser Phe Phe
        350                 355                 360 gta act cct tca gac tct gta gcc gtt att gca gcc aat gca aaa gaa     1157
Val Thr Pro Ser Asp Ser Val Ala Val Ile Ala Ala Asn Ala Lys Glu
    365                 370                 375 gcg att ccg tac ttt aag gac agt atc aag ggt ctt gca cga tca atg     1205
Ala Ile Pro Tyr Phe Lys Asp Ser Ile Lys Gly Leu Ala Arg Ser Met
380                 385                 390                 395 ccg aca agc ggt gct cta gat aga gtt gct gaa aag ttg aac ctc cct     1253
Pro Thr Ser Gly Ala Leu Asp Arg Val Ala Glu Lys Leu Asn Leu Pro
                400                 405                 410 ttt ttt gag gtt ccc act ggt tgg aaa ttc ttt ggt aat ctt atg gat     1301
Phe Phe Glu Val Pro Thr Gly Trp Lys Phe Phe Gly Asn Leu Met Asp
            415                 420                 425 gct gga aat ctg tcg att tgc ggg gaa gag agt ttt gga aca ggt tct     1349
Ala Gly Asn Leu Ser Ile Cys Gly Glu Glu Ser Phe Gly Thr Gly Ser
        430                 435                 440 gac cac att cgt gag aaa gac gga atc tgg gct gta tta gct tgg ctt     1397
Asp His Ile Arg Glu Lys Asp Gly Ile Trp Ala Val Leu Ala Trp Leu
    445                 450                 455 tcg att att gct cac cgc aac aaa gac acg aaa cca ggg gag aaa ttg     1445
Ser Ile Ile Ala His Arg Asn Lys Asp Thr Lys Pro Gly Glu Lys Leu
460                 465                 470                 475 gtc tct gtg tct gat gtt gtg aag gag cat tgg gca acc tat ggt aga     1493
Val Ser Val Ser Asp Val Val Lys Glu His Trp Ala Thr Tyr Gly Arg
                480                 485                 490 aat ttc ttt tct aga tac gat tac gag gaa tgt gaa tcc gaa ggc gca     1541
Asn Phe Phe Ser Arg Tyr Asp Tyr Glu Glu Cys Glu Ser Glu Gly Ala
            495                 500                 505 aat aag atg ata gag tac cta cga gag ctt ttg tcg aag agc aag cct     1589
Asn Lys Met Ile Glu Tyr Leu Arg Glu Leu Leu Ser Lys Ser Lys Pro
        510                 515                 520
```

```
ggt gat aag tat gga agt tac gtc ctc cag ttt gcc gat gat tat aca   1637
Gly Asp Lys Tyr Gly Ser Tyr Val Leu Gln Phe Ala Asp Asp Tyr Thr
525                 530                 535 tac act gat cct gta gat gga agt gta gta tca aaa caa ggg gtt cgg   1685
Tyr Thr Asp Pro Val Asp Gly Ser Val Val Ser Lys Gln Gly Val Arg
540                 545                 550                 555 ttt gtt ttc acc gat ggt tca aga att att tac cgt tta tca gga acg   1733
Phe Val Phe Thr Asp Gly Ser Arg Ile Ile Tyr Arg Leu Ser Gly Thr
                560                 565                 570 ggt tct gct ggt gca act gtt aga gtg tat atc gaa cag ttt gaa cca   1781
Gly Ser Ala Gly Ala Thr Val Arg Val Tyr Ile Glu Gln Phe Glu Pro
            575                 580                 585 gat gtt tct aaa cac gac gtc gat gct caa att gcc ttg aaa cca tta   1829
Asp Val Ser Lys His Asp Val Asp Ala Gln Ile Ala Leu Lys Pro Leu
        590                 595                 600 ata gat tta gca tta tct gtt tca aag ctc aaa gac ttc aca ggg a     1875
Ile Asp Leu Ala Leu Ser Val Ser Lys Leu Lys Asp Phe Thr Gly
    605                 610                 615

<210> SEQ ID NO 14
<211> LENGTH: 618
<212> TYPE: PRT
<213> ORGANISM: Pisum sativum

<400> SEQUENCE: 14

Met Ala Phe Cys Tyr Arg Leu Asp Asn Phe Ile Ile Ser Ala Phe Lys
1               5                   10                  15

Pro Lys His Ser Asn Val Pro Leu Ser Ile His His Ser Ser Ser Asn
                20                  25                  30

Phe Pro Ser Phe Lys Val Gln Asn Phe Pro Phe Arg Val Arg Tyr Asn
            35                  40                  45

Ser Ala Ile Arg Ala Thr Ser Ser Ser Ser Thr Pro Thr Thr Ile
        50                  55                  60

Ala Glu Pro Asn Asp Ile Lys Ile Asn Ser Ile Pro Thr Lys Pro Ile
65                  70                  75                  80

Glu Gly Gln Lys Thr Gly Thr Ser Gly Leu Arg Lys Lys Val Lys Val
                85                  90                  95

Phe Lys Gln Glu Asn Tyr Leu Ala Asn Trp Ile Gln Ala Leu Phe Asn
            100                 105                 110

Ser Leu Pro Pro Glu Asp Tyr Lys Asn Gly Leu Leu Val Leu Gly Gly
        115                 120                 125

Asp Gly Arg Tyr Phe Asn Lys Glu Ala Ala Gln Ile Ile Lys Ile
    130                 135                 140

Ala Ala Gly Asn Gly Val Gly Lys Ile Leu Val Gly Lys Glu Gly Ile
145                 150                 155                 160

Leu Ser Thr Pro Ala Val Ser Ala Ile Arg Lys Arg Glu Ala Asn
                165                 170                 175

Gly Gly Phe Ile Met Ser Ala Ser His Asn Pro Gly Gly Pro Glu Tyr
            180                 185                 190

Asp Trp Gly Ile Lys Phe Asn Tyr Ser Ser Gly Gln Pro Ala Pro Glu
        195                 200                 205

Ser Ile Thr Asp Lys Ile Tyr Gly Asn Thr Leu Ser Ile Ser Glu Ile
    210                 215                 220

Lys Ile Ala Asp Ile Pro Asp Val Asp Leu Ser Asn Val Gly Val Thr
225                 230                 235                 240

Lys Phe Gly Ser Phe Ser Val Glu Val Ile Asp Pro Val Ser Asp Tyr
                245                 250                 255
```

```
Leu Glu Leu Leu Glu Thr Val Phe Asp Phe Gln Leu Ile Lys Ser Leu
            260                 265                 270

Ile Ser Arg Pro Asp Phe Arg Phe Thr Phe Asp Ala Met His Ala Val
            275                 280                 285

Ala Gly Ala Tyr Ala Thr Pro Ile Phe Val Asp Lys Leu Gly Ala Ser
            290                 295                 300

Pro Asp Ser Ile Ser Asn Gly Ile Pro Leu Glu Asp Phe Gly His Gly
305                 310                 315                 320

His Pro Asp Pro Asn Leu Thr Tyr Ala Lys Asp Leu Val Asn Ile Met
                325                 330                 335

Tyr Ala Glu Asn Gly Pro Asp Phe Gly Ala Ala Ser Asp Gly Asp Gly
            340                 345                 350

Asp Arg Asn Met Ile Leu Gly Thr Ser Phe Phe Val Thr Pro Ser Asp
            355                 360                 365

Ser Val Ala Val Ile Ala Ala Asn Ala Lys Glu Ala Ile Pro Tyr Phe
            370                 375                 380

Lys Asp Ser Ile Lys Gly Leu Ala Arg Ser Met Pro Thr Ser Gly Ala
385                 390                 395                 400

Leu Asp Arg Val Ala Glu Lys Leu Asn Leu Pro Phe Phe Glu Val Pro
                405                 410                 415

Thr Gly Trp Lys Phe Phe Gly Asn Leu Met Asp Ala Gly Asn Leu Ser
            420                 425                 430

Ile Cys Gly Glu Glu Ser Phe Gly Thr Gly Ser Asp His Ile Arg Glu
            435                 440                 445

Lys Asp Gly Ile Trp Ala Val Leu Ala Trp Leu Ser Ile Ile Ala His
            450                 455                 460

Arg Asn Lys Asp Thr Lys Pro Gly Glu Lys Leu Val Ser Val Ser Asp
465                 470                 475                 480

Val Val Lys Glu His Trp Ala Thr Tyr Gly Arg Asn Phe Phe Ser Arg
                485                 490                 495

Tyr Asp Tyr Glu Glu Cys Glu Ser Glu Gly Ala Asn Lys Met Ile Glu
            500                 505                 510

Tyr Leu Arg Glu Leu Leu Ser Lys Ser Lys Pro Gly Asp Lys Tyr Gly
            515                 520                 525

Ser Tyr Val Leu Gln Phe Ala Asp Asp Tyr Thr Tyr Thr Asp Pro Val
            530                 535                 540

Asp Gly Ser Val Val Ser Lys Gln Gly Val Arg Phe Val Phe Thr Asp
545                 550                 555                 560

Gly Ser Arg Ile Ile Tyr Arg Leu Ser Gly Thr Gly Ser Ala Gly Ala
                565                 570                 575

Thr Val Arg Val Tyr Ile Glu Gln Phe Glu Pro Asp Val Ser Lys His
            580                 585                 590

Asp Val Asp Ala Gln Ile Ala Leu Lys Pro Leu Ile Asp Leu Ala Leu
            595                 600                 605

Ser Val Ser Lys Leu Lys Asp Phe Thr Gly
            610                 615

<210> SEQ ID NO 15
<211> LENGTH: 2006
<212> TYPE: DNA
<213> ORGANISM: Pisum sativum
<220> FEATURE:
<221> NAME/KEY: misc_feature
<222> LOCATION: (1976)..(1976)
<223> OTHER INFORMATION: N = A or C or G or T/U
```

<400> SEQUENCE: 15

```
ctttctgtta cagactcgac aacttcatca tctctgcgtt taaacccaaa cactcaaatg     60
tcccactttc aattcatcat tcatcatcca attttccttc tttcaaagtt caaaactttc    120
ctttcagggt tcgctataat tcagctatta gagccacttc gtcttcctct tctactccca    180
caaccattgc agaacctaat gacattaaga ttaactctat tcctactaaa cctattgaag    240
gacaaaaaac tggtaccagt ggcctaagaa aaaggtgaa agtgtttaag caagaaaatt     300
accttgcaaa ttggattcag gcactgttta attcgttgcc gccggaggat tacaagaatg    360
gattgttggt tttgggaggc gatggtcgat acttcaataa agaagctgca cagataataa    420
tcaagattgc tgctggaaat ggtgttggaa aaattctggt tgggaaggaa gggatattgt    480
caacgccagc cgtttctgct gtgataagga agagagaggc aaatggtggg tttatcatga    540
gtgcgagcca taaccctggt ggacctgaat atgattgggg tattaagttt aattacagta    600
gcggacaacc tgcaccagaa tccatcaccg acaagattta cggaaacacc ctatcgattt    660
ctgagataaa gattgctgat attcccgatg ttgacttatc aaatgttgga gttacgaaat    720
tcggaagctt cagtgtggaa gtaatagacc cagtttctga ttacctggag ttattgggaga  780
cagtgttcga ttttcagcta atcaaaagtc ttatttcacg ccagattttt aggtttacat    840
ttgatgccat gcatgcagtt gccggtgctt atgcaacacc cattttcgtt gataaacttg    900
gtgctagtcc ggattcaatt tcaaatggaa taccttttgga agattttgga catggtcatc    960
ctgatcctaa tctaacatac gcaaggatcc ttgtcaatat tatgtatgct gaaaacggac   1020
ctgattttgg tgccgctagt gatggtgatg gtgatagaaa tatgatttttg ggaacaagtt   1080
tcttcgtaac tccttcagac tctgtagccg ttattgcagc caatgcaaaa gaagcgattc   1140
cgtactttaa ggacagtatc aagggtcttg cacgatcaat gccgacaagc ggtgctctag   1200
atagagttgc tgaaaagttg aacctccctt tttttgaggt tcccactggt tggaaattct   1260
ttggtaatct tatggatgct ggaaatctgt cgatttgcgg ggaagagagt tttggaacag   1320
gttctgacca cattcgtgag aaagacggaa tctggtaact ttcttatttt tgtattgaga   1380
atagcgggtc gagcatttat caaacattat ctaagtttct ccgacttatt aatattattg   1440
ggctgtatta gcttggcttt cgattattgc tcaccgcaac aaagacacga aaccagggga   1500
gaaattggtc tctgtgtctg atgttgtgaa ggagcattgg gcaacctatg gtagaaattt   1560
cttttctaga tacgattacg aggttggttt tgatgctgca attgaagttt tatttgttgt   1620
atcacacact ttgaagtttt attttctttt tgagttttga caaatataaa tataggaatg   1680
tgaatccgaa ggcgcaaata agatgataga gtacctacga gagcttttgt cgaagagcaa   1740
gcctggtgat aagtatggaa gttacgtcct ccagtttgcc gatgattata catcactga    1800
tcctgtagat ggaagtgtag tatcaaaaca aggggttcgg tttgttttca ccgatggttc   1860
aagaattatt taccgtttat caggaacggg ttctgctggt gcaactgtta gagtgtatat   1920
cgaacagttt gaaccagatg tttctaaaca cgacgtcgat gctcaaattg ccttrnacca   1980
tkdaatagat ttagcattat ctgttt                                        2006
```

<210> SEQ ID NO 16
<211> LENGTH: 451
<212> TYPE: PRT
<213> ORGANISM: Pisum sativum

<400> SEQUENCE: 16

-continued

```
Phe Cys Tyr Arg Leu Asp Asn Phe Ile Ile Ser Ala Phe Lys Pro Lys
 1               5                  10                  15

His Ser Asn Val Pro Leu Ser Ile His His Ser Ser Ser Asn Phe Pro
             20                  25                  30

Ser Phe Lys Val Gln Asn Phe Pro Phe Arg Val Arg Tyr Asn Ser Ala
         35                  40                  45

Ile Arg Ala Thr Ser Ser Ser Ser Thr Pro Thr Thr Ile Ala Glu
 50                  55                  60

Pro Asn Asp Ile Lys Ile Asn Ser Ile Pro Thr Lys Pro Ile Glu Gly
 65                  70                  75                  80

Gln Lys Thr Gly Thr Ser Gly Leu Arg Lys Lys Val Lys Val Phe Lys
                 85                  90                  95

Gln Glu Asn Tyr Leu Ala Asn Trp Ile Gln Ala Leu Phe Asn Ser Leu
                100                 105                 110

Pro Pro Glu Asp Tyr Lys Asn Gly Leu Leu Val Leu Gly Gly Asp Gly
            115                 120                 125

Arg Tyr Phe Asn Lys Glu Ala Ala Gln Ile Ile Lys Ile Ala Ala
130                 135                 140

Gly Asn Gly Val Gly Lys Ile Leu Val Gly Lys Gly Ile Leu Ser
145                 150                 155                 160

Thr Pro Ala Val Ser Ala Val Ile Arg Lys Arg Glu Ala Asn Gly Gly
                165                 170                 175

Phe Ile Met Ser Ala Ser His Asn Pro Gly Gly Pro Glu Tyr Asp Trp
                180                 185                 190

Gly Ile Lys Phe Asn Tyr Ser Ser Gly Gln Pro Ala Pro Glu Ser Ile
            195                 200                 205

Thr Asp Lys Ile Tyr Gly Asn Thr Leu Ser Ile Ser Glu Ile Lys Ile
            210                 215                 220

Ala Asp Ile Pro Asp Val Asp Leu Ser Asn Val Gly Val Thr Lys Phe
225                 230                 235                 240

Gly Ser Phe Ser Val Glu Val Ile Asp Pro Val Ser Asp Tyr Leu Glu
                245                 250                 255

Leu Leu Glu Thr Val Phe Asp Phe Gln Leu Ile Lys Ser Leu Ile Ser
                260                 265                 270

Arg Pro Asp Phe Arg Phe Thr Phe Asp Ala Met His Ala Val Ala Gly
            275                 280                 285

Ala Tyr Ala Thr Pro Ile Phe Val Asp Lys Leu Gly Ala Ser Pro Asp
            290                 295                 300

Ser Ile Ser Asn Gly Ile Pro Leu Glu Asp Phe Gly His Gly His Pro
305                 310                 315                 320

Asp Pro Asn Leu Thr Tyr Ala Lys Asp Leu Val Asn Ile Met Tyr Ala
                325                 330                 335

Glu Asn Gly Pro Asp Phe Gly Ala Ala Ser Asp Gly Asp Gly Asp Arg
            340                 345                 350

Asn Met Ile Leu Gly Thr Ser Phe Phe Val Thr Pro Ser Asp Ser Val
            355                 360                 365

Ala Val Ile Ala Ala Asn Ala Lys Glu Ala Ile Pro Tyr Phe Lys Asp
            370                 375                 380

Ser Ile Lys Gly Leu Ala Arg Ser Met Pro Thr Ser Gly Ala Leu Asp
385                 390                 395                 400

Arg Val Ala Glu Lys Leu Asn Leu Pro Phe Phe Glu Val Pro Thr Gly
                405                 410                 415

Trp Lys Phe Phe Gly Asn Leu Met Asp Ala Gly Asn Leu Ser Ile Cys
```

-continued

```
                420                 425                 430
Gly Glu Glu Ser Phe Gly Thr Gly Ser Asp His Ile Arg Glu Lys Asp
            435                 440                 445
Gly Ile Trp
    450

<210> SEQ ID NO 17
<211> LENGTH: 1055
<212> TYPE: DNA
<213> ORGANISM: Pisum sativum
<220> FEATURE:
<221> NAME/KEY: CDS
<222> LOCATION: (2)..(751)
<223> OTHER INFORMATION:

<400> SEQUENCE: 17 g att gct gat att ccc gat gtt gac tta tca aat gtt gga gtt acg aaa      49
  Ile Ala Asp Ile Pro Asp Val Asp Leu Ser Asn Val Gly Val Thr Lys
  1               5                   10                  15 ttc gga agc ttc agt gtg gaa gta ata gac cca gtt tct gat tac ctg       97
Phe Gly Ser Phe Ser Val Glu Val Ile Asp Pro Val Ser Asp Tyr Leu
                20                  25                  30 gag tta ttg gag aca gtg ttc gat ttt cag cta atc aaa agt ctt att      145
Glu Leu Leu Glu Thr Val Phe Asp Phe Gln Leu Ile Lys Ser Leu Ile
            35                  40                  45 tca cgg cca gat ttt agg ttt aca ttt gat gcc atg cat gca gtt gcc      193
Ser Arg Pro Asp Phe Arg Phe Thr Phe Asp Ala Met His Ala Val Ala
 50                  55                  60 ggt gct tat gca aca ccc att ttc gtt gat aaa ctt ggt gct agt ccg      241
Gly Ala Tyr Ala Thr Pro Ile Phe Val Asp Lys Leu Gly Ala Ser Pro
 65                  70                  75                  80 gat tca att tca aat gga ata cct ttg gaa gat ttt gga cat ggt cat      289
Asp Ser Ile Ser Asn Gly Ile Pro Leu Glu Asp Phe Gly His Gly His
                85                  90                  95 cct gat cct aat cta aca tac gca aag gat ctt gtc aat att atg tat      337
Pro Asp Pro Asn Leu Thr Tyr Ala Lys Asp Leu Val Asn Ile Met Tyr
            100                 105                 110 gct gaa aac gga cct gat ttt ggt gcc gct agt gat ggt gat ggt gat      385
Ala Glu Asn Gly Pro Asp Phe Gly Ala Ala Ser Asp Gly Asp Gly Asp
        115                 120                 125 aga aat atg att ttg gga aca agt ttc ttc gta act cct tca gac tct      433
Arg Asn Met Ile Leu Gly Thr Ser Phe Phe Val Thr Pro Ser Asp Ser
    130                 135                 140 gta gcc gtt att gca gcc aat gca aaa gaa gcg att ccg tac ttt aag      481
Val Ala Val Ile Ala Ala Asn Ala Lys Glu Ala Ile Pro Tyr Phe Lys
145                 150                 155                 160 gac agt atc aag ggt ctt gca cga tca atg ccg aca agc ggt gct cta      529
Asp Ser Ile Lys Gly Leu Ala Arg Ser Met Pro Thr Ser Gly Ala Leu
                165                 170                 175 gat aga gtt gct gaa aag ttg aac ctc cct ttt ttt gag gtt ccc act      577
Asp Arg Val Ala Glu Lys Leu Asn Leu Pro Phe Phe Glu Val Pro Thr
            180                 185                 190 ggt tgg aaa ttc ttt ggt aat ctt atg gat gct gga aat ctg tcg att      625
Gly Trp Lys Phe Phe Gly Asn Leu Met Asp Ala Gly Asn Leu Ser Ile
        195                 200                 205 tgc ggg gaa gag agt ttt gga aca ggt tct gac cac att cgt gag aaa      673
Cys Gly Glu Glu Ser Phe Gly Thr Gly Ser Asp His Ile Arg Glu Lys
    210                 215                 220 gac gga atc tgc ttg gct ttc gat tat tgc tca ccg caa caa aga cac      721
Asp Gly Ile Cys Leu Ala Phe Asp Tyr Cys Ser Pro Gln Gln Arg His
225                 230                 235                 240
```

-continued

```
gaa acc agg gga gaa att ggt ctc tgt gtc tgatgttgtg aaggagcatt      771
Glu Thr Arg Gly Glu Ile Gly Leu Cys Val
            245                 250 gggcaaccta tggtagaaat ttcttttcta gatacgatta cgaggaatgt gaatccgaag   831
gcgcaaataa gatgatagag tacctacgag agcttttgtc gaagagcaag cctggtgata   891
agtatggaag ttacgtcctc cagtttgccg atgattatac atacactgat cctgtagatg   951
gaagtgtagt atcaaaacaa ggggttcggt ttgttttcac cgatggttca agaattattt  1011
accgtttatc aggaacgggt tctgctggtg caactgttag agtg                   1055
```

<210> SEQ ID NO 18
<211> LENGTH: 250
<212> TYPE: PRT
<213> ORGANISM: Pisum sativum

<400> SEQUENCE: 18

```
Ile Ala Asp Ile Pro Asp Val Asp Leu Ser Asn Val Gly Val Thr Lys
1               5                   10                  15

Phe Gly Ser Phe Ser Val Glu Val Ile Asp Pro Val Ser Asp Tyr Leu
            20                  25                  30

Glu Leu Leu Glu Thr Val Phe Asp Phe Gln Leu Ile Lys Ser Leu Ile
        35                  40                  45

Ser Arg Pro Asp Phe Arg Phe Thr Phe Asp Ala Met His Ala Val Ala
    50                  55                  60

Gly Ala Tyr Ala Thr Pro Ile Phe Val Asp Lys Leu Gly Ala Ser Pro
65                  70                  75                  80

Asp Ser Ile Ser Asn Gly Ile Pro Leu Glu Asp Phe Gly His Gly His
                85                  90                  95

Pro Asp Pro Asn Leu Thr Tyr Ala Lys Asp Leu Val Asn Ile Met Tyr
            100                 105                 110

Ala Glu Asn Gly Pro Asp Phe Gly Ala Ala Ser Asp Gly Asp Gly Asp
        115                 120                 125

Arg Asn Met Ile Leu Gly Thr Ser Phe Phe Val Thr Pro Ser Asp Ser
    130                 135                 140

Val Ala Val Ile Ala Ala Asn Ala Lys Glu Ala Ile Pro Tyr Phe Lys
145                 150                 155                 160

Asp Ser Ile Lys Gly Leu Ala Arg Ser Met Pro Thr Ser Gly Ala Leu
                165                 170                 175

Asp Arg Val Ala Glu Lys Leu Asn Leu Pro Phe Phe Glu Val Pro Thr
            180                 185                 190

Gly Trp Lys Phe Phe Gly Asn Leu Met Asp Ala Gly Asn Leu Ser Ile
        195                 200                 205

Cys Gly Glu Glu Ser Phe Gly Thr Gly Ser Asp His Ile Arg Glu Lys
    210                 215                 220

Asp Gly Ile Cys Leu Ala Phe Asp Tyr Cys Ser Pro Gln Gln Arg His
225                 230                 235                 240

Glu Thr Arg Gly Glu Ile Gly Leu Cys Val
                245                 250
```

<210> SEQ ID NO 19
<211> LENGTH: 1733
<212> TYPE: DNA
<213> ORGANISM: Pisum sativum
<220> FEATURE:
<221> NAME/KEY: CDS
<222> LOCATION: (21)..(1406)

<223> OTHER INFORMATION:

<400> SEQUENCE: 19

| | | | | | | | | | | | | | | | | |
|---|---|---|---|---|---|---|---|---|---|---|---|---|---|---|---|---|
| cactgttaca | gactcgatca | atg | gct | ttc | tgt | tac | aga | ctc | gac | aac | ttc | atc | | | | 53 |
| | | Met | Ala | Phe | Cys | Tyr | Arg | Leu | Asp | Asn | Phe | Ile | | | | |
| | | 1 | | | 5 | | | | | 10 | | | | | | |
| atc | tct | gcg | ttt | aaa | ccc | aaa | cac | tca | aat | gtc | cca | ctt | tca | att | cat | 101 |
| Ile | Ser | Ala | Phe | Lys | Pro | Lys | His | Ser | Asn | Val | Pro | Leu | Ser | Ile | His | |
| | | 15 | | | | | 20 | | | | | 25 | | | | |
| cat | tca | tca | tcc | aat | ttt | cct | tct | ttc | aaa | gtt | caa | aac | ttt | cct | ttc | 149 |
| His | Ser | Ser | Ser | Asn | Phe | Pro | Ser | Phe | Lys | Val | Gln | Asn | Phe | Pro | Phe | |
| | 30 | | | | | 35 | | | | | 40 | | | | | |
| agg | gtt | cgc | tat | aat | tca | gct | att | aga | gcc | act | tcg | tct | tcc | tct | tct | 197 |
| Arg | Val | Arg | Tyr | Asn | Ser | Ala | Ile | Arg | Ala | Thr | Ser | Ser | Ser | Ser | Ser | |
| | 45 | | | | | 50 | | | | | 55 | | | | | |
| act | ccc | aca | acc | att | gca | gaa | cct | aat | gac | att | aag | att | aac | tct | att | 245 |
| Thr | Pro | Thr | Thr | Ile | Ala | Glu | Pro | Asn | Asp | Ile | Lys | Ile | Asn | Ser | Ile | |
| 60 | | | | 65 | | | | | 70 | | | | | 75 | | |
| cct | act | aaa | cct | att | gaa | gga | caa | aaa | act | ggt | acc | agt | ggc | cta | aga | 293 |
| Pro | Thr | Lys | Pro | Ile | Glu | Gly | Gln | Lys | Thr | Gly | Thr | Ser | Gly | Leu | Arg | |
| | | | 80 | | | | | 85 | | | | | 90 | | | |
| aaa | aag | gtg | aaa | gtg | ttt | aag | caa | gaa | aat | tac | ctt | gca | aat | tgg | att | 341 |
| Lys | Lys | Val | Lys | Val | Phe | Lys | Gln | Glu | Asn | Tyr | Leu | Ala | Asn | Trp | Ile | |
| | | | 95 | | | | | 100 | | | | | 105 | | | |
| cag | gca | ctg | ttt | aat | tcg | ttg | ccg | ccg | gag | gat | tac | aag | aat | gga | ttg | 389 |
| Gln | Ala | Leu | Phe | Asn | Ser | Leu | Pro | Pro | Glu | Asp | Tyr | Lys | Asn | Gly | Leu | |
| | | 110 | | | | | 115 | | | | | 120 | | | | |
| ttg | gtt | ttg | gga | ggc | gat | ggt | cga | tac | ttc | aat | aaa | gaa | gct | gca | cag | 437 |
| Leu | Val | Leu | Gly | Gly | Asp | Gly | Arg | Tyr | Phe | Asn | Lys | Glu | Ala | Ala | Gln | |
| | 125 | | | | | 130 | | | | | 135 | | | | | |
| ata | ata | atc | aag | att | gct | gct | gga | aat | ggt | gtt | gga | aaa | att | ctg | gtt | 485 |
| Ile | Ile | Ile | Lys | Ile | Ala | Ala | Gly | Asn | Gly | Val | Gly | Lys | Ile | Leu | Val | |
| 140 | | | | 145 | | | | | 150 | | | | | 155 | | |
| ggg | aag | gaa | ggg | ata | ttg | tca | acg | cca | gcc | gtt | tct | gct | gtg | ata | agg | 533 |
| Gly | Lys | Glu | Gly | Ile | Leu | Ser | Thr | Pro | Ala | Val | Ser | Ala | Val | Ile | Arg | |
| | | | 160 | | | | | 165 | | | | | 170 | | | |
| aag | aga | gag | gca | aat | ggt | ggg | ttt | atc | atg | agt | gcg | agc | cat | aac | cct | 581 |
| Lys | Arg | Glu | Ala | Asn | Gly | Gly | Phe | Ile | Met | Ser | Ala | Ser | His | Asn | Pro | |
| | | 175 | | | | | 180 | | | | | 185 | | | | |
| ggt | gga | cct | gaa | tat | gat | tgg | ggt | att | aag | ttt | aat | tac | agt | agc | gga | 629 |
| Gly | Gly | Pro | Glu | Tyr | Asp | Trp | Gly | Ile | Lys | Phe | Asn | Tyr | Ser | Ser | Gly | |
| | 190 | | | | | 195 | | | | | 200 | | | | | |
| caa | cct | gca | cca | gaa | tcc | atc | acc | gac | aag | att | tac | gga | aac | acc | cta | 677 |
| Gln | Pro | Ala | Pro | Glu | Ser | Ile | Thr | Asp | Lys | Ile | Tyr | Gly | Asn | Thr | Leu | |
| 205 | | | | 210 | | | | | 215 | | | | | | | |
| tcg | att | tct | gag | ata | aag | att | gct | gat | att | ccc | gat | gtt | gac | tta | tca | 725 |
| Ser | Ile | Ser | Glu | Ile | Lys | Ile | Ala | Asp | Ile | Pro | Asp | Val | Asp | Leu | Ser | |
| 220 | | | | 225 | | | | | 230 | | | | | 235 | | |
| aat | gtt | gga | gtt | acg | aaa | ttc | gga | agc | ttc | agt | gtg | gaa | gta | ata | gac | 773 |
| Asn | Val | Gly | Val | Thr | Lys | Phe | Gly | Ser | Phe | Ser | Val | Glu | Val | Ile | Asp | |
| | | | 240 | | | | | 245 | | | | | 250 | | | |
| cca | gtt | tct | gat | tac | ctg | gag | tta | ttg | gag | aca | gtg | ttc | gat | ttt | cag | 821 |
| Pro | Val | Ser | Asp | Tyr | Leu | Glu | Leu | Leu | Glu | Thr | Val | Phe | Asp | Phe | Gln | |
| | | 255 | | | | | 260 | | | | | 265 | | | | |
| cta | atc | aaa | agt | ctt | att | tca | cgg | cca | gat | ttt | agg | ttt | aca | ttt | gat | 869 |
| Leu | Ile | Lys | Ser | Leu | Ile | Ser | Arg | Pro | Asp | Phe | Arg | Phe | Thr | Phe | Asp | |
| | 270 | | | | | 275 | | | | | 280 | | | | | |
| gcc | atg | cat | gca | gtt | gcc | ggt | gct | tat | gca | aca | ccc | att | ttc | gtt | gat | 917 |
| Ala | Met | His | Ala | Val | Ala | Gly | Ala | Tyr | Ala | Thr | Pro | Ile | Phe | Val | Asp | |
| 285 | | | | 290 | | | | | 295 | | | | | | | |

-continued

```
aaa ctt ggt gct agt ccg gat tca att tca aat gga ata cct ttg gaa      965
Lys Leu Gly Ala Ser Pro Asp Ser Ile Ser Asn Gly Ile Pro Leu Glu
300                 305                 310                 315 gat ttt gga cat ggt cat cct gat cct aat cta aca tac gca aag gat     1013
Asp Phe Gly His Gly His Pro Asp Pro Asn Leu Thr Tyr Ala Lys Asp
                320                 325                 330 ctt gtc aat att atg tat gct gaa aac gga cct gat ttt ggt gcc gct     1061
Leu Val Asn Ile Met Tyr Ala Glu Asn Gly Pro Asp Phe Gly Ala Ala
            335                 340                 345 agt gat ggt gat ggt gat aga aat atg att ttg gga aca agt ttc ttc     1109
Ser Asp Gly Asp Gly Asp Arg Asn Met Ile Leu Gly Thr Ser Phe Phe
        350                 355                 360 gta act cct tca gac tct gta gcc gtt att gca gcc aat gca aaa gaa     1157
Val Thr Pro Ser Asp Ser Val Ala Val Ile Ala Ala Asn Ala Lys Glu
    365                 370                 375 gcg att ccg tac ttt aag gac agt atc aag ggt ctt gca cga tca atg     1205
Ala Ile Pro Tyr Phe Lys Asp Ser Ile Lys Gly Leu Ala Arg Ser Met
380                 385                 390                 395 ccg aca agc ggt gct cta gat aga gtt gct gaa aag ttg aac ctc cct     1253
Pro Thr Ser Gly Ala Leu Asp Arg Val Ala Glu Lys Leu Asn Leu Pro
                400                 405                 410 ttt ttt gag gtt ccc act ggt tgg aaa ttc ttt ggt aat ctt atg gat     1301
Phe Phe Glu Val Pro Thr Gly Trp Lys Phe Phe Gly Asn Leu Met Asp
            415                 420                 425 gct gga aat ctg tcg att tgc ggg gaa gag agt ttt gga aca ggt tct     1349
Ala Gly Asn Leu Ser Ile Cys Gly Glu Glu Ser Phe Gly Thr Gly Ser
        430                 435                 440 gac cac att cgt gag aaa gac gga atc tgg aat gtg aat ccg aag gcg     1397
Asp His Ile Arg Glu Lys Asp Gly Ile Trp Asn Val Asn Pro Lys Ala
    445                 450                 455 caa ata aga tgatagagta cctacgagag cttttgtcga agagcaagcc             1446
Gln Ile Arg
460 tggtgataag tatggaagtt acgtcctcca gtttgccgat gattatacat acactgatcc   1506 tgtagatgga agtgtagtat caaaacaagg ggttcggttt gttttcaccg atggttcaag   1566 aattatttac cgtttatcag gaacgggttc tgctggtgca actgttagag tgtatatcga   1626 acagtttgaa ccagatgttt ctaaaacacga cgtcgatgct caaattgcct tgaaaccatt  1686 aatagattta gcattatctg tttcaaagct caaagacttc acaggga                 1733
```

<210> SEQ ID NO 20
<211> LENGTH: 462
<212> TYPE: PRT
<213> ORGANISM: Pisum sativum

<400> SEQUENCE: 20

```
Met Ala Phe Cys Tyr Arg Leu Asp Asn Phe Ile Ile Ser Ala Phe Lys
1               5                   10                  15

Pro Lys His Ser Asn Val Pro Leu Ser Ile His His Ser Ser Ser Asn
            20                  25                  30

Phe Pro Ser Phe Lys Val Gln Asn Phe Pro Phe Arg Val Arg Tyr Asn
        35                  40                  45

Ser Ala Ile Arg Ala Thr Ser Ser Ser Ser Thr Pro Thr Thr Ile
    50                  55                  60

Ala Glu Pro Asn Asp Ile Lys Ile Asn Ser Ile Pro Thr Lys Pro Ile
65                  70                  75                  80

Glu Gly Gln Lys Thr Gly Thr Ser Gly Leu Arg Lys Lys Val Lys Val
```

```
                       85                  90                  95
Phe Lys Gln Glu Asn Tyr Leu Ala Asn Trp Ile Gln Ala Leu Phe Asn
                100                 105                 110

Ser Leu Pro Pro Glu Asp Tyr Lys Asn Gly Leu Val Leu Gly Gly
                115                 120             125

Asp Gly Arg Tyr Phe Asn Lys Glu Ala Ala Gln Ile Ile Lys Ile
            130                 135                 140

Ala Ala Gly Asn Gly Val Gly Lys Ile Leu Val Gly Lys Glu Gly Ile
145                 150                 155                 160

Leu Ser Thr Pro Ala Val Ser Ala Val Ile Arg Lys Arg Glu Ala Asn
                165                 170                 175

Gly Gly Phe Ile Met Ser Ala Ser His Asn Pro Gly Gly Pro Glu Tyr
                180                 185                 190

Asp Trp Gly Ile Lys Phe Asn Tyr Ser Ser Gly Gln Pro Ala Pro Glu
            195                 200                 205

Ser Ile Thr Asp Lys Ile Tyr Gly Asn Thr Leu Ser Ile Ser Glu Ile
            210                 215                 220

Lys Ile Ala Asp Ile Pro Asp Val Asp Leu Ser Asn Val Gly Val Thr
225                 230                 235                 240

Lys Phe Gly Ser Phe Ser Val Glu Val Ile Asp Pro Val Ser Asp Tyr
                245                 250                 255

Leu Glu Leu Leu Glu Thr Val Phe Asp Phe Gln Leu Ile Lys Ser Leu
                260                 265                 270

Ile Ser Arg Pro Asp Phe Arg Phe Thr Phe Asp Ala Met His Ala Val
            275                 280                 285

Ala Gly Ala Tyr Ala Thr Pro Ile Phe Val Asp Lys Leu Gly Ala Ser
            290                 295                 300

Pro Asp Ser Ile Ser Asn Gly Ile Pro Leu Glu Asp Phe Gly His Gly
305                 310                 315                 320

His Pro Asp Pro Asn Leu Thr Tyr Ala Lys Asp Leu Val Asn Ile Met
                325                 330                 335

Tyr Ala Glu Asn Gly Pro Asp Phe Gly Ala Ala Ser Asp Gly Asp Gly
                340                 345                 350

Asp Arg Asn Met Ile Leu Gly Thr Ser Phe Phe Val Thr Pro Ser Asp
            355                 360                 365

Ser Val Ala Val Ile Ala Ala Asn Ala Lys Glu Ala Ile Pro Tyr Phe
370                 375                 380

Lys Asp Ser Ile Lys Gly Leu Ala Arg Ser Met Pro Thr Ser Gly Ala
385                 390                 395                 400

Leu Asp Arg Val Ala Glu Lys Leu Asn Leu Pro Phe Phe Glu Val Pro
                405                 410                 415

Thr Gly Trp Lys Phe Phe Gly Asn Leu Met Asp Ala Gly Asn Leu Ser
            420                 425                 430

Ile Cys Gly Glu Glu Ser Phe Gly Thr Gly Ser Asp His Ile Arg Glu
            435                 440                 445

Lys Asp Gly Ile Trp Asn Val Asn Pro Lys Ala Gln Ile Arg
450                 455                 460

<210> SEQ ID NO 21
<211> LENGTH: 35
```

-continued

```
<212> TYPE: DNA
<213> ORGANISM: Pisum sativum

<400> SEQUENCE: 21
ggagatctgg taagcttgtt tttttttttt ttttt                                35
```